United States Patent [19]
Glorioso et al.

[11] Patent Number: 6,159,464
[45] Date of Patent: *Dec. 12, 2000

[54] VIRAL VECTORS TO INHIBIT LEUKOCYTE INFILTRATION OR CARTILAGE DEGRADATION OF JOINTS

[75] Inventors: Joseph C. Glorioso, Cheswick; Christopher H. Evans; Paul D. Robbins, both of Pittsburgh; Steven C. Ghivizzani, Allison Park, all of Pa.

[73] Assignee: University of Pittsburgh of the Commonwealth System of Higher Education, Pittsburgh, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/924,376

[22] Filed: Sep. 5, 1997

Related U.S. Application Data

[63] Continuation-in-part of application No. 08/685,212, Jul. 23, 1996, which is a continuation of application No. 08/027,750, Mar. 8, 1993, abandoned, which is a continuation-in-part of application No. 07/630,981, Dec. 20, 1990, abandoned.

[51] Int. Cl.$^7$ ............................. A01N 63/00; A61K 48/00
[52] U.S. Cl. .......................... 424/93.2; 424/93.6; 514/825
[58] Field of Search .................... 514/44, 825; 424/93.2, 424/93.21, 93.6; 435/320.1

[56] References Cited

U.S. PATENT DOCUMENTS

| | | | |
|---|---|---|---|
| 4,396,601 | 8/1983 | Salser et al. | 424/94 |
| 4,766,069 | 8/1988 | Auron et al. | 435/70 |
| 4,778,806 | 10/1988 | Bender et al. | 514/336 |
| 4,780,470 | 10/1988 | Bender et al. | 514/341 |
| 4,794,114 | 12/1988 | Bender et al. | 514/333 |
| 4,816,436 | 3/1989 | Jacobs | 514/2 |
| 4,870,101 | 9/1989 | Ku et al. | 514/476 |
| 4,935,343 | 6/1990 | Allison et al. | 435/7 |
| 4,968,607 | 11/1990 | Dower et al. | 435/69.1 |
| 5,081,228 | 1/1992 | Dower et al. | 530/35.1 |
| 5,180,812 | 1/1993 | Dower et al. | 530/351 |
| 5,792,751 | 8/1998 | Ledley et al. | 514/44 |

FOREIGN PATENT DOCUMENTS 9211359 7/1992 WIPO .

OTHER PUBLICATIONS

Blau et al. (Nov. 2, 1995) New Eng. J. Med., 1204–1207.
Sawchuk et al. (1996) Human Gene Therapy 7, 499–506.
Zhang et al. (1997) J. Clin. Invest. 100, 1951–1957.
Evans, C. et al., "Pathways to gene therapy in rhumatoid arthritis," *Current Opinion in Rheumatology*, 8:230–234 (1996).
Roessler, B.J. et al., "Adenoviral–mediated Gene Transfer to Rabbit Synovium In Vivo," *J. Clin. Invest.*, 92:1085–1092 (1993).
Roessler, B.J. et al., "Inhibition of Interleukin–1–Induced Effects in Synoviocytes Transduced with the Human IL–1 Receptor Antagonist cDNA Using an Adenoviral Vector," *Human Gene Therapy*, 6:307–316 (1995).
Nicolau et al., "In Vivo Expression of Rat Insulin After Intravenous Administration of the Liposome–Entrapped Gene For Rat Insulin I", *Proc. Natl Acad. Sci. USA*, vol. 80, pp. 1068–1072 (Feb. 1983).
Aston and Bentley, "Repair of Articular Surfaces by Allografts of Articular and Growth–Plate Cartilage", *The Journal of Bone and Joint Surgery*, vol. 68 B, No. 1, pp. 29–35 (Jan. 1986).
Pettipher et al., "Interleukin 1 Induces Leukocyte Infiltration and Cartilage Proteoglycan Degradation in the Synovial Joint", *Proc. Natl. Acad. Sci. USA*, vol. 83, pp. 8749–8753 (Nov. 1986).
Price et al., "Lineage Analysis in the Vertebrate Nervous System By Retrovirus–Mediated Gene Transfer", *Proc. Natl. Acad. Sci. USA*, vol. 84, pp. 156–160 (Jan. 1987).
Korman et al., "Expression of Human Class II Major Histocompatibility Complex Antigens Using Retrovirus Vectors", *Proc. Natl. Acad. Sci. USA*, vol. 84, pp. 2150–2154 (Apr. 1987).
Banerjee et al., "Immunosuppression of Collagen–Induced Arthritis in Mice with an Anti–IL–2 Receptor Antibody", *The Journal of Immunology*, vol. 141, No. 4, pp. 1150–1154 (Aug. 1988).
Danos et al., "Safe and Efficient Generation of Recombinant Retroviruses with Amphotropic and Ecotropic Host Ranges", *Proc. Natl. Acad. Sci. USA*, vol. 85, pp. 6460–6464 (Sep. 1988).
Rosenberg et al., "Grafting Genetically Modified Cells to the Damaged Brain: Restorative Effects of NGF Expression", *Science*, vol. 242, pp. 1575–1578 (Dec. 1988).

(List continued on next page.)

*Primary Examiner*—Deborah Crouch
*Attorney, Agent, or Firm*—Townsend and Townsend and Crew LLP

[57] ABSTRACT

Methods for treating a connective tissue disorder by introducing at least one gene encoding a product into at least one target cell of a mammalian host for use in treating the mammalian host are disclosed. These methods include employing recombinant techniques to produce a vector molecule containing the DNA sequence encoding for the product and infecting the target cell of the mammalian host using the vector. The injection can be done in vivo, by directly injecting the vector into the host, or can be done in vitro by transfecting a population of cultured target cells with the vector and transplanting them each into the host. Nonviral means can also be used to introduce the DNA sequence to the host. Administration of more than one gene of interest results in an enhanced therapeutic benefit. Also disclosed is a method for treating a connective tissue disorder by introducing at least one gene encoding a product into at least one target cell of a joint of a host for use in treating multiple joints of the host. Injection of a vector molecule containing the DNA sequence encoding for a product of interest, or non-viral introduction of such a DNA sequence, to one join of a mammalian host results in a therapeutic benefit in that joint as well as other joints in the host

7 Claims, 40 Drawing Sheets

OTHER PUBLICATIONS

Grande et al., "The Repair of Experimentally Produced Defects in Rabbit Articular Cartilage by Autologous Chondrocyte Transplantation", *Journal of Orthopaedic Research*, vol. 7, No. 2, pp. 208–218 (1989).

Wakitani et al., "Repair of Rabbit Articular Surfaces with Allograft Chondrocytes Embedded in Collagen Gel", *The Journal of Bone and Joint Surgery*, vol. 71–B, No. 1, pp. 74–80 (Jan. 1989).

Chin et al., "Interleukin 1 Receptors on Rabbit Articular Chondrocytes: Relationship Between Biological Activity and Receptor Binding Kinetics", *The FASEB Journal*, vol. 4, pp. 1481–1487 (Mar. 1990).

Fanslow et al., "Regulation of Alloreactivity in Vivo by a Soluble Form of the Interleukin–1 Receptor", *Science*, vol. 248, pp. 739–742 (May 1990).

Gao et al., "A Novel Cationic Liposome Reagent for Efficient Transfection of Mammalian Cells", *Biochemical and Biophysical Research Communications*, vol. 179, No. 1, pp. 280–285 (Aug. 1991).

Bandara et al., "Intraarticular Expression of IRAP by Gene Transfer", *Arthritis Rheum.*, vol. 39 (supp), S193, C161 (1992).

Evans, "Transferring Therapeutic Genes to Joints: A Pittsburgh Idea", *The Pittsburgh Orthopaedic Journal*, vol. 3, pp. 130–131 (1992).

Evans et al., "Gene Transfer to Joints for Arthritis Therapy", *J. Cell Biochem.*, 16F:V207 (1992).

Bandara et al., "Gene Transfer to Synoviocytes: Prospects for Gene Treatment of Arthritis", *DNA and Cell Biology*, vol. 11, No. 3, pp. 227–231 (1992).

Evans et al., "Synovial Cell Transplants for Gene Transfer to Joints", *Transplantation Proceedings*, vol. 24, No. 6, p. 2966 (Dec. 1992).

Bandara et al., "Gene Transfer to Synovium", *Trans. Orthop. Res. Soc.*, 18, p. 242 (1993).

Wooley et al, "The Effect of an Interleukin–1 Receptor Antagonist Protein on Type II Collagen–Induced Arthritis and Antigen–Induced Arthritis in Mice", *Arthritis & Rheumatism*, vol. 36, pp. 1305–1314 (1993).

Bandara et al., "Intraarticular Expression of Biologically Active Interleukin 1–Receptor–Antagonist Protein By Ex Vivo Gene Transfer", *Proc. Natl. Acad. Sci. USA* vol. 90, pp. 10764–10768 (Nov. 1993).

Endo et al., "Experimental Arthritis Induced by Continuous Infusion of IL–8 Into Rabbit Knee Joints", *Clinical & Experimental Immunology*, vol. 96, pp. 31–35 (1994).

Structure Of The PLJ - ILrec Retroviral Vector And Partial Restriction Endonuclease Map LTR - Long Terminal Repeats - Regulates Viral Transcription And Expression Of IL-1 Receptor neo^r - Bacterial Gene Encoding Resistance To The Antibiotic Neomycin SV 40 - Simian Virus 40 Enhancer Promoter - Regulates Expression Of The neo^r Gene

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1770 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vii) IMMEDIATE SOURCE:
      (A) LIBRARY: Human T-cell cDNA Library
      (B) CLONE: Human Interleukin-1 Receptor (ix) FEATURE:
      (A) NAME/KEY: CDS
      (B) LOCATION: 55..1764

(xi) SEQUENCE DESCRIPTION: SEQ ID NO:1:

```
CCTCCTGAGA AGCTGGACCC CTTGGTAAAA GACAAGGCCT TCTCCAAGAA GAAT ATG         57
                                                          Met
                                                          1

AAA GTG TTA CTC AGA CTT ATT TGT TTC ATA GCT CTA CTG ATT TCT TCT       105
Lys Val Leu Leu Arg Leu Ile Cys Phe Ile Ala Leu Leu Ile Ser Ser
```

```
              5                    10                      15
CTG GAG GCT GAT AAA TGC AAG GAA CGT GAA GAA AAA ATA ATT TTA GTG        153
Leu Glu Ala Asp Lys Cys Lys Glu Arg Glu Glu Lys Ile Ile Leu Val
            20                  25                  30

TCA TCT GCA AAT GAA ATT GAT GTT CGT CCC TGT CCT CTT AAC CCA AAT        201
Ser Ser Ala Asn Glu Ile Asp Val Arg Pro Cys Pro Leu Asn Pro Asn
        35                  40                  45

GAA CAC AAA GGC ACT ATA ACT TGG TAT AAA GAT GAC AGC AAG ACA CCT        249
Glu His Lys Gly Thr Ile Thr Trp Tyr Lys Asp Asp Ser Lys Thr Pro
 50                  55                  60                  65

GTA TCT ACA GAA CAA GCC TCC AGG ATT CAT CAA CAC AAA GAG AAA CTT        297
Val Ser Thr Glu Gln Ala Ser Arg Ile His Gln His Lys Glu Lys Leu
            70                  75                  80

TGG TTT GTT CCT GCT AAG GTG GAG GAT TCA GGA CAT TAC TAT TGC GTG        345
Trp Phe Val Pro Ala Lys Val Glu Asp Ser Gly His Tyr Tyr Cys Val
        85                  90                  95

GTA AGA AAT TCA TCT TAC TGC CTC AGA ATT AAA ATA AGT GCA AAA TTT        393
Val Arg Asn Ser Ser Tyr Cys Leu Arg Ile Lys Ile Ser Ala Lys Phe
            100                 105                 110

GTG GAG AAT GAG CCT AAC TTA TGT TAT AAT GCA CAA GCC ATA TTT AAG        441
Val Glu Asn Glu Pro Asn Leu Cys Tyr Asn Ala Gln Ala Ile Phe Lys
        115                 120                 125

CAG AAA CTA CCC GTT GCA GGA GAC GGA GGA CTT GTG TGC CCT TAT ATG        489
Gln Lys Leu Pro Val Ala Gly Asp Gly Gly Leu Val Cys Pro Tyr Met
130                 135                 140                 145

GAG TTT TTT AAA AAT GAA AAT AAT GAG TTA CCT AAA TTA CAG TGG TAT        537
Glu Phe Phe Lys Asn Glu Asn Asn Glu Leu Pro Lys Leu Gln Trp Tyr
                150                 155                 160

AAG GAT TGC AAA CCT CTA CTT CTT GAC AAT ATA CAC TTT AGT GGA GTC        585
Lys Asp Cys Lys Pro Leu Leu Leu Asp Asn Ile His Phe Ser Gly Val
            165                 170                 175

AAA GAT AGG CTC ATC GTG ATG AAT GTG GCT GAA AAG CAT AGA GGG AAC        633
Lys Asp Arg Leu Ile Val Met Asn Val Ala Glu Lys His Arg Gly Asn
        180                 185                 190

TAT ACT TGT CAT GCA TCC TAC ACA TAC TTG GGC AAG CAA TAT CCT ATT        681
Tyr Thr Cys His Ala Ser Tyr Thr Tyr Leu Gly Lys Gln Tyr Pro Ile
195                 200                 205

ACC CGG GTA ATA GAA TTT ATT ACT CTA GAG GAA AAC AAA CCC ACA AGG        729
Thr Arg Val Ile Glu Phe Ile Thr Leu Glu Glu Asn Lys Pro Thr Arg
210                 215                 220                 225

CCT GTG ATT GTG AGC CCA GCT AAT GAG ACA ATG GAA GTA GAC TTG GGA        777
Pro Val Ile Val Ser Pro Ala Asn Glu Thr Met Glu Val Asp Leu Gly
                230                 235                 240

TCC CAG ATA CAA TTG ATC TGT AAT GTC ACC GGC CAG TTG AGT GAC ATT        825
Ser Gln Ile Gln Leu Ile Cys Asn Val Thr Gly Gln Leu Ser Asp Ile
            245                 250                 255

GCT TAC TGG AAG TGG AAT GGG TCA GTA ATT GAT GAA GAT GAC CCA GTG        873
Ala Tyr Trp Lys Trp Asn Gly Ser Val Ile Asp Glu Asp Asp Pro Val
        260                 265                 270

CTA GGG GAA GAC TAT TAC AGT GTG GAA AAT CCT GCA AAC AAA AGA AGG        921
Leu Gly Glu Asp Tyr Tyr Ser Val Glu Asn Pro Ala Asn Lys Arg Arg
275                 280                 285

AGT ACC CTC ATC ACA GTG CTT AAT ATA TCG GAA ATT GAA AGT AGA TTT        969
Ser Thr Leu Ile Thr Val Leu Asn Ile Ser Glu Ile Glu Ser Arg Phe
290                 295                 300                 305

TAT AAA CAT CCA TTT ACC TGT TTT GCC AAG AAT ACA CAT GGT ATA GAT        1017
Tyr Lys His Pro Phe Thr Cys Phe Ala Lys Asn Thr His Gly Ile Asp
                310                 315                 320

GCA GCA TAT ATC CAG TTA ATA TAT CCA GTC ACT AAT TTC CAG AAG CAC        1065
```

```
Ala Ala Tyr Ile Gln Leu Ile Tyr Pro Val Thr Asn Phe Gln Lys His
            325                 330                 335

ATG ATT GGT ATA TGT GTC ACG TTG ACA GTC ATA ATT GTG TGT TCT GTT              1113
Met Ile Gly Ile Cys Val Thr Leu Thr Val Ile Ile Val Cys Ser Val
        340                 345                 350

TTC ATC TAT AAA ATC TTC AAG ATT GAC ATT GTG CTT TGG TAC AGG GAT              1161
Phe Ile Tyr Lys Ile Phe Lys Ile Asp Ile Val Leu Trp Tyr Arg Asp
355                 360                 365

TCC TGC TAT GAT TTT CTC CCA ATA AAA GCT TCA GAT GGA AAG ACC TAT              1209
Ser Cys Tyr Asp Phe Leu Pro Ile Lys Ala Ser Asp Gly Lys Thr Tyr
370                 375                 380                 385

GAC GCA TAT ATA CTG TAT CCA AAG ACT GTT GGG GAA GGG TCT ACC TCT              1257
Asp Ala Tyr Ile Leu Tyr Pro Lys Thr Val Gly Glu Gly Ser Thr Ser
            390                 395                 400

GAC TGT GAT ATT TTT GTG TTT AAA GTC TTG CCT GAG GTC TTG GAA AAA              1305
Asp Cys Asp Ile Phe Val Phe Lys Val Leu Pro Glu Val Leu Glu Lys
        405                 410                 415

CAG TGT GGA TAT AAG CTG TTC ATT TAT GGA AGG GAT GAC TAC GTT GGG              1353
Gln Cys Gly Tyr Lys Leu Phe Ile Tyr Gly Arg Asp Asp Tyr Val Gly
        420                 425                 430

GAA GAC ATT GTT GAG GTC ATT AAT GAA AAC GTA AAG AAA AGC AGA AGA              1401
Glu Asp Ile Val Glu Val Ile Asn Glu Asn Val Lys Lys Ser Arg Arg
435                 440                 445

CTG ATT ATC ATT TTA GTC AGA GAA ACA TCA GGC TTC AGC TGG CTG GGT              1449
Leu Ile Ile Ile Leu Val Arg Glu Thr Ser Gly Phe Ser Trp Leu Gly
450                 455                 460                 465

GGT TCA TCT GAA GAG CAA ATA GCC ATG TAT AAT GCT CTT GTT CAG GAT              1497
Gly Ser Ser Glu Glu Gln Ile Ala Met Tyr Asn Ala Leu Val Gln Asp
            470                 475                 480

GGA ATT AAA GTT GTC CTG CTT GAG CTG GAG AAA ATC CAA GAC TAT GAG              1545
Gly Ile Lys Val Val Leu Leu Glu Leu Glu Lys Ile Gln Asp Tyr Glu
        485                 490                 495

AAA ATG CCA GAA TCG ATT AAA TTC ATT AAG CAG AAA CAT GGG GCT ATC              1593
Lys Met Pro Glu Ser Ile Lys Phe Ile Lys Gln Lys His Gly Ala Ile
500                 505                 510

CGC TGG TCA GGG GAC TTT ACA CAG GGA CCA CAG TCT GCA AAG ACA AGG              1641
Arg Trp Ser Gly Asp Phe Thr Gln Gly Pro Gln Ser Ala Lys Thr Arg
        515                 520                 525

TTC TGG AAG AAT GTC AGG TAC CAC ATG CCA GTC CAG CGA CGG TCA CCT              1689
Phe Trp Lys Asn Val Arg Tyr His Met Pro Val Gln Arg Arg Ser Pro
530                 535                 540                 545

TCA TCT AAA CAC CAG TTA CTG TCA CCA GCC ACT AAG GAG AAA CTG CAA              1737
Ser Ser Lys His Gln Leu Leu Ser Pro Ala Thr Lys Glu Lys Leu Gln
            550                 555                 560

AGA GAG GCT CAC GTG CCT CTC GGG TAGCATGGA                                    1770
Arg Glu Ala His Val Pro Leu Gly
            565                 570

(2) INFORMATION FOR SEQ ID NO:2:

(i) SEQUENCE CHARACTERISTICS:
        (A) LENGTH: 569 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Val Leu Leu Arg Leu Ile Cys Phe Ile Ala Leu Leu Ile Ser
 1               5                   10                  15

Ser Leu Glu Ala Asp Lys Cys Lys Glu Arg Glu Glu Lys Ile Ile Leu
```

```
            20                  25                  30
Val Ser Ser Ala Asn Glu Ile Asp Val Arg Pro Cys Pro Leu Asn Pro
         35                  40                  45
Asn Glu His Lys Gly Thr Ile Thr Trp Tyr Lys Asp Asp Ser Lys Thr
 50                  55                  60
Pro Val Ser Thr Glu Gln Ala Ser Arg Ile His Gln His Lys Glu Lys
 65                  70                  75                  80
Leu Trp Phe Val Pro Ala Lys Val Glu Asp Ser Gly His Tyr Tyr Cys
                 85                  90                  95
Val Val Arg Asn Ser Ser Tyr Cys Leu Arg Ile Lys Ile Ser Ala Lys
                100                 105                 110
Phe Val Glu Asn Glu Pro Asn Leu Cys Tyr Asn Ala Gln Ala Ile Phe
            115                 120                 125
Lys Gln Lys Leu Pro Val Ala Gly Asp Gly Leu Val Cys Pro Tyr
        130                 135                 140
Met Glu Phe Phe Lys Asn Glu Asn Asn Glu Leu Pro Lys Leu Gln Trp
145                 150                 155                 160
Tyr Lys Asp Cys Lys Pro Leu Leu Leu Asp Asn Ile His Phe Ser Gly
                165                 170                 175
Val Lys Asp Arg Leu Ile Val Met Asn Val Ala Glu Lys His Arg Gly
            180                 185                 190
Asn Tyr Thr Cys His Ala Ser Tyr Thr Tyr Leu Gly Lys Gln Tyr Pro
        195                 200                 205
Ile Thr Arg Val Ile Glu Phe Ile Thr Leu Glu Glu Asn Lys Pro Thr
    210                 215                 220
Arg Pro Val Ile Val Ser Pro Ala Asn Glu Thr Met Glu Val Asp Leu
225                 230                 235                 240
Gly Ser Gln Ile Gln Leu Ile Cys Asn Val Thr Gly Gln Leu Ser Asp
                245                 250                 255
Ile Ala Tyr Trp Lys Trp Asn Gly Ser Val Ile Asp Glu Asp Asp Pro
            260                 265                 270
Val Leu Gly Glu Asp Tyr Tyr Ser Val Glu Asn Pro Ala Asn Lys Arg
        275                 280                 285
Arg Ser Thr Leu Ile Thr Val Leu Asn Ile Ser Glu Ile Glu Ser Arg
    290                 295                 300
Phe Tyr Lys His Pro Phe Thr Cys Phe Ala Lys Asn Thr His Gly Ile
305                 310                 315                 320
Asp Ala Ala Tyr Ile Gln Leu Ile Tyr Pro Val Thr Asn Phe Gln Lys
                325                 330                 335
His Met Ile Gly Ile Cys Val Thr Leu Thr Val Ile Ile Val Cys Ser
            340                 345                 350
Val Phe Ile Tyr Lys Ile Phe Lys Ile Asp Ile Val Leu Trp Tyr Arg
        355                 360                 365
Asp Ser Cys Tyr Asp Phe Leu Pro Ile Lys Ala Ser Asp Gly Lys Thr
    370                 375                 380
Tyr Asp Ala Tyr Ile Leu Tyr Pro Lys Thr Val Gly Glu Gly Ser Thr
385                 390                 395                 400
Ser Asp Cys Asp Ile Phe Val Phe Lys Val Leu Pro Glu Val Leu Glu
                405                 410                 415
Lys Gln Cys Gly Tyr Lys Leu Phe Ile Tyr Gly Arg Asp Asp Tyr Val
            420                 425                 430
Gly Glu Asp Ile Val Glu Val Ile Asn Glu Asn Val Lys Lys Ser Arg
        435                 440                 445
```

```
Arg Leu Ile Ile Ile Leu Val Arg Glu Thr Ser Gly Phe Ser Trp Leu
    450                 455                 460

Gly Gly Ser Ser Glu Glu Gln Ile Ala Met Tyr Asn Ala Leu Val Gln
465                 470                 475                 480

Asp Gly Ile Lys Val Val Leu Glu Leu Glu Lys Ile Gln Asp Tyr
                485                 490                 495

Glu Lys Met Pro Glu Ser Ile Lys Phe Ile Lys Gln Lys His Gly Ala
                500                 505                 510

Ile Arg Trp Ser Gly Asp Phe Thr Gln Gly Pro Gln Ser Ala Lys Thr
            515                 520                 525

Arg Phe Trp Lys Asn Val Arg Tyr His Met Pro Val Gln Arg Arg Ser
    530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565
```

(2) INFORMATION FOR SEQ ID NO:3:

(i) SEQUENCE CHARACTERISTICS:
      (A) LENGTH: 1782 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vii) IMMEDIATE SOURCE:
      (A) LIBRARY: Mouse T-cell cDNA Library
      (B) CLONE: Mouse Interleukin-1 Receptor (ix) FEATURE:
      (A) NAME/KEY: CDS
      (B) LOCATION: 46..1776

(xi) SEQUENCE DESCRIPTION: SEQ ID NO:3:

```
GGATGTCATC AGAGTTCCCA GTGCCCCGAA CCGTGAACAA CACAA ATG GAG AAT         54
                                                  Met Glu Asn
                                                    1

ATG AAA GTG CTA CTG GGG CTC ATT TGT CTC ATG GTG CCT CTG CTG TCG     102
Met Lys Val Leu Leu Gly Leu Ile Cys Leu Met Val Pro Leu Leu Ser
      5                  10                  15

CTG GAG ATT GAC GTA TGT ACA GAA TAT CCA AAT CAG ATC GTT TTG TTT    150
Leu Glu Ile Asp Val Cys Thr Glu Tyr Pro Asn Gln Ile Val Leu Phe
 20                  25                  30                  35

TTA TCT GTA AAT GAA ATT GAT ATT CGC AAG TGT CCT CTT ACT CCA AAT    198
Leu Ser Val Asn Glu Ile Asp Ile Arg Lys Cys Pro Leu Thr Pro Asn
                 40                  45                  50

AAA ATG CAC GGC GAC ACC ATA ATT TGG TAC AAG AAT GAC AGC AAG ACC    246
Lys Met His Gly Asp Thr Ile Ile Trp Tyr Lys Asn Asp Ser Lys Thr
                     55                  60                  65

CCC ATA TCA GCG GAC CGG GAC TCC AGG ATT CAT CAG CAG AAT GAA CAT    294
Pro Ile Ser Ala Asp Arg Asp Ser Arg Ile His Gln Gln Asn Glu His
             70                  75                  80

CTT TGG TTT GTA CCT GCC AAG GTG GAG GAC TCA GGA TAT TAC TAT TGT    342
Leu Trp Phe Val Pro Ala Lys Val Glu Asp Ser Gly Tyr Tyr Tyr Cys
     85                  90                  95

ATA GTA AGA AAC TCA ACT TAC TGC CTC AAA ACT AAA GTA ACC GTA ACT    390
```

-continued

| | | | | | | | | | | | | | |
|---|---|---|---|---|---|---|---|---|---|---|---|---|---|
| Ile | Val | Arg | Asn | Ser | Thr | Tyr | Cys | Leu | Lys | Thr | Lys | Val | Thr | Val | Thr |
| 100 | | | | | 105 | | | | | 110 | | | | | 115 |

| GTG TTA GAG AAT GAC CCT GGC TTG TGT TAC AGC ACA CAG GCC ACC TTC | 438 |
|---|---|
| Val Leu Glu Asn Asp Pro Gly Leu Cys Tyr Ser Thr Gln Ala Thr Phe<br>120     125      130 | |

| CCA CAG CGG CTC CAC ATT GCC GGG GAT GGA AGT CTT GTG TGC CCT TAT | 486 |
|---|---|
| Pro Gln Arg Leu His Ile Ala Gly Asp Gly Ser Leu Val Cys Pro Tyr<br>    135      140      145 | |

| GTG AGT TAT TTT AAA GAT GAA AAT AAT GAG TTA CCC GAG GTC CAG TGG | 534 |
|---|---|
| Val Ser Tyr Phe Lys Asp Glu Asn Asn Glu Leu Pro Glu Val Gln Trp<br>  150      155      160 | |

| TAT AAG AAC TGT AAA CCT CTG CTT CTT GAC AAC GTG AGC TTC TTC GGA | 582 |
|---|---|
| Tyr Lys Asn Cys Lys Pro Leu Leu Leu Asp Asn Val Ser Phe Phe Gly<br>  165      170      175 | |

| GTA AAA GAT AAA CTG TTG GTG AGG AAT GTG GCT GAA GAG CAC AGA GGG | 630 |
|---|---|
| Val Lys Asp Lys Leu Leu Val Arg Asn Val Ala Glu Glu His Arg Gly<br>180     185      190      195 | |

| GAC TAT ATA TGC CGT ATG TCC TAT ACG TTC CGG GGG AAG CAA TAT CCG | 678 |
|---|---|
| Asp Tyr Ile Cys Arg Met Ser Tyr Thr Phe Arg Gly Lys Gln Tyr Pro<br>    200      205      210 | |

| GTC ACA CGA GTA ATA CAA TTT ATC ACA ATA GAT GAA AAC AAG AGG GAC | 726 |
|---|---|
| Val Thr Arg Val Ile Gln Phe Ile Thr Ile Asp Glu Asn Lys Arg Asp<br>    215      220      225 | |

| AGA CCT GTT ATC CTG AGC CCT CGG AAT GAG ACG ATC GAA GCT GAC CCA | 774 |
|---|---|
| Arg Pro Val Ile Leu Ser Pro Arg Asn Glu Thr Ile Glu Ala Asp Pro<br>    230      235      240 | |

| GGA TCA ATG ATA CAA CTG ATC TGC AAC GTC ACG GGC CAG TTC TCA GAC | 822 |
|---|---|
| Gly Ser Met Ile Gln Leu Ile Cys Asn Val Thr Gly Gln Phe Ser Asp<br>245     250      255 | |

| CTT GTC TAC TGG AAG TGG AAT GGA TCA GAA ATT GAA TGG AAT GAT CCA | 870 |
|---|---|
| Leu Val Tyr Trp Lys Trp Asn Gly Ser Glu Ile Glu Trp Asn Asp Pro<br>260     265      270      275 | |

| TTT CTA GCT GAA GAC TAT CAA TTT GTG GAA CAT CCT TCA ACC AAA AGA | 918 |
|---|---|
| Phe Leu Ala Glu Asp Tyr Gln Phe Val Glu His Pro Ser Thr Lys Arg<br>    280      285      290 | |

| AAA TAC ACA CTC ATT ACA ACA CTT AAC ATT TCA GAA GTT AAA AGC CAG | 966 |
|---|---|
| Lys Tyr Thr Leu Ile Thr Thr Leu Asn Ile Ser Glu Val Lys Ser Gln<br>    295      300      305 | |

| TTT TAT CGC TAT CCG TTT ATC TGT GTT GTT AAG AAC ACA AAT ATT TTT | 1014 |
|---|---|
| Phe Tyr Arg Tyr Pro Phe Ile Cys Val Val Lys Asn Thr Asn Ile Phe<br>    310      315      320 | |

| GAG TCG GCG CAT GTG CAG TTA ATA TAC CCA GTC CCT GAC TTC AAG AAT | 1062 |
|---|---|
| Glu Ser Ala His Val Gln Leu Ile Tyr Pro Val Pro Asp Phe Lys Asn<br>325     330      335 | |

| TAC CTC ATC GGG GGC TTT ATC ATC CTC ACG GCT ACA ATT GTA TGC TGT | 1110 |
|---|---|
| Tyr Leu Ile Gly Gly Phe Ile Ile Leu Thr Ala Thr Ile Val Cys Cys<br>340     345      350      355 | |

| GTG TGC ATC TAT AAA GTC TTC AAG GTT GAC ATA GTG CTT TGG TAC AGG | 1158 |
|---|---|
| Val Cys Ile Tyr Lys Val Phe Lys Val Asp Ile Val Leu Trp Tyr Arg<br>    360      365      370 | |

| GAC TCC TGC TCT GGT TTT CTT CCT TCA AAA GCT TCA GAT GGA AAG ACA | 1206 |
|---|---|
| Asp Ser Cys Ser Gly Phe Leu Pro Ser Lys Ala Ser Asp Gly Lys Thr<br>    375      380      385 | |

| TAC GAT GCA TAT ATT CTT TAT CCC AAG ACC CTG GGA GAG GGG TCC TTC | 1254 |
|---|---|
| Tyr Asp Ala Tyr Ile Leu Tyr Pro Lys Thr Leu Gly Glu Gly Ser Phe<br>    390      395      400 | |

| TCA GAC TTA GAT ACT TTT GTT TTT AAA CTG TTG CCT GAG GTC TTG GAG | 1302 |
|---|---|
| Ser Asp Leu Asp Thr Phe Val Phe Lys Leu Leu Pro Glu Val Leu Glu<br>405     410      415 | |

```
GGA CAG TTT GGA TAC AAG CTG TTC ATT TAT GGA AGG GAT GAC TAT GTT      1350
Gly Gln Phe Gly Tyr Lys Leu Phe Ile Tyr Gly Arg Asp Asp Tyr Val
420                 425                 430                 435

GGA GAA GAT ACC ATC GAG GTT ACT AAT GAA AAT GTA AAG AAA AGC AGG      1398
Gly Glu Asp Thr Ile Glu Val Thr Asn Glu Asn Val Lys Lys Ser Arg
                440                 445                 450

AGG CTG ATT ATC ATT CTA GTG AGA GAT ATG GGA GGC TTC AGC TGG CTG      1446
Arg Leu Ile Ile Ile Leu Val Arg Asp Met Gly Gly Phe Ser Trp Leu
            455                 460                 465

GGC CAG TCA TCT GAA GAG CAA ATA GCC ATA TAC AAT GCT CTC ATC CAG      1494
Gly Gln Ser Ser Glu Glu Gln Ile Ala Ile Tyr Asn Ala Leu Ile Gln
        470                 475                 480

GAA GGA ATT AAA ATC GTC CTG CTT GAG TTG GAG AAA ATC CAA GAC TAT      1542
Glu Gly Ile Lys Ile Val Leu Leu Glu Leu Glu Lys Ile Gln Asp Tyr
    485                 490                 495

GAG AAA ATG CCA GAT TCT ATT CAG TTC ATT AAG CAG AAA CAC GGA GTC      1590
Glu Lys Met Pro Asp Ser Ile Gln Phe Ile Lys Gln Lys His Gly Val
500                 505                 510                 515

ATT TGC TGG TCA GGA GAC TTT CAA GAA AGA CCA CAG TCT GCA AAG ACC      1638
Ile Cys Trp Ser Gly Asp Phe Gln Glu Arg Pro Gln Ser Ala Lys Thr
                520                 525                 530

AGG TTC TGG AAA AAC TTA AGA TAC CAG ATG CCA GCC CAA CGG AGA TCA      1686
Arg Phe Trp Lys Asn Leu Arg Tyr Gln Met Pro Ala Gln Arg Arg Ser
            535                 540                 545

CCA TTG TCT AAA CAC CGC TTA CTA ACC CTG GAT CCT GTG CGG GAC ACT      1734
Pro Leu Ser Lys His Arg Leu Leu Thr Leu Asp Pro Val Arg Asp Thr
        550                 555                 560

AAG GAG AAA CTG CCG GCA GCA ACA CAC TTA CCA CTC GGC TAGCATGGC        1782
Lys Glu Lys Leu Pro Ala Ala Thr His Leu Pro Leu Gly
    565                 570                 575

(2) INFORMATION FOR SEQ ID NO:4:

(i) SEQUENCE CHARACTERISTICS:
        (A) LENGTH: 576 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Asn Met Lys Val Leu Leu Gly Leu Ile Cys Leu Met Val Pro
1               5                   10                  15

Leu Leu Ser Leu Glu Ile Asp Val Cys Thr Glu Tyr Pro Asn Gln Ile
            20                  25                  30

Val Leu Phe Leu Ser Val Asn Glu Ile Asp Ile Arg Lys Cys Pro Leu
        35                  40                  45

Thr Pro Asn Lys Met His Gly Asp Thr Ile Ile Trp Tyr Lys Asn Asp
    50                  55                  60

Ser Lys Thr Pro Ile Ser Ala Asp Arg Asp Ser Arg Ile His Gln Gln
65                  70                  75                  80

Asn Glu His Leu Trp Phe Val Pro Ala Lys Val Glu Asp Ser Gly Tyr
            85                  90                  95

Tyr Tyr Cys Ile Val Arg Asn Ser Thr Tyr Cys Leu Lys Thr Lys Val
        100                 105                 110

Thr Val Thr Val Leu Glu Asn Asp Pro Gly Leu Cys Tyr Ser Thr Gln
    115                 120                 125

Ala Thr Phe Pro Gln Arg Leu His Ile Ala Gly Asp Gly Ser Leu Val
    130                 135                 140
```

-continued

```
Cys Pro Tyr Val Ser Tyr Phe Lys Asp Glu Asn Asn Glu Leu Pro Glu
145                 150                 155                 160

Val Gln Trp Tyr Lys Asn Cys Lys Pro Leu Leu Leu Asp Asn Val Ser
            165                 170                 175

Phe Phe Gly Val Lys Asp Lys Leu Leu Val Arg Asn Val Ala Glu Glu
        180                 185                 190

His Arg Gly Asp Tyr Ile Cys Arg Met Ser Tyr Thr Phe Arg Gly Lys
    195                 200                 205

Gln Tyr Pro Val Thr Arg Val Ile Gln Phe Ile Thr Ile Asp Glu Asn
210                 215                 220

Lys Arg Asp Arg Pro Val Ile Leu Ser Pro Arg Asn Glu Thr Ile Glu
225                 230                 235                 240

Ala Asp Pro Gly Ser Met Ile Gln Leu Ile Cys Asn Val Thr Gly Gln
                245                 250                 255

Phe Ser Asp Leu Val Tyr Trp Lys Trp Asn Gly Ser Glu Ile Glu Trp
            260                 265                 270

Asn Asp Pro Phe Leu Ala Glu Asp Tyr Gln Phe Val Glu His Pro Ser
        275                 280                 285

Thr Lys Arg Lys Tyr Thr Leu Ile Thr Thr Leu Asn Ile Ser Glu Val
    290                 295                 300

Lys Ser Gln Phe Tyr Arg Tyr Pro Phe Ile Cys Val Val Lys Asn Thr
305                 310                 315                 320

Asn Ile Phe Glu Ser Ala His Val Gln Leu Ile Tyr Pro Val Pro Asp
                325                 330                 335

Phe Lys Asn Tyr Leu Ile Gly Gly Phe Ile Ile Leu Thr Ala Thr Ile
            340                 345                 350

Val Cys Cys Val Cys Ile Tyr Lys Val Phe Lys Val Asp Ile Val Leu
        355                 360                 365

Trp Tyr Arg Asp Ser Cys Ser Gly Phe Leu Pro Ser Lys Ala Ser Asp
    370                 375                 380

Gly Lys Thr Tyr Asp Ala Tyr Ile Leu Tyr Pro Lys Thr Leu Gly Glu
385                 390                 395                 400

Gly Ser Phe Ser Asp Leu Asp Thr Phe Val Phe Lys Leu Leu Pro Glu
                405                 410                 415

Val Leu Glu Gly Gln Phe Gly Tyr Lys Leu Phe Ile Tyr Gly Arg Asp
            420                 425                 430

Asp Tyr Val Gly Glu Asp Thr Ile Glu Val Thr Asn Glu Asn Val Lys
        435                 440                 445

Lys Ser Arg Arg Leu Ile Ile Ile Leu Val Arg Asp Met Gly Gly Phe
450                 455                 460

Ser Trp Leu Gly Gln Ser Ser Glu Glu Gln Ile Ala Ile Tyr Asn Ala
465                 470                 475                 480

Leu Ile Gln Glu Gly Ile Lys Ile Val Leu Leu Glu Leu Glu Lys Ile
                485                 490                 495

Gln Asp Tyr Glu Lys Met Pro Asp Ser Ile Gln Phe Ile Lys Gln Lys
            500                 505                 510

His Gly Val Ile Cys Trp Ser Gly Asp Phe Gln Glu Arg Pro Gln Ser
        515                 520                 525

Ala Lys Thr Arg Phe Trp Lys Asn Leu Arg Tyr Gln Met Pro Ala Gln
    530                 535                 540

Arg Arg Ser Pro Leu Ser Lys His Arg Leu Leu Thr Leu Asp Pro Val
545                 550                 555                 560

Arg Asp Thr Lys Glu Lys Leu Pro Ala Ala Thr His Leu Pro Leu Gly
```

-continued

```
                565                 570                 575
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Primer oligonucleotide (iii) HYPOTHETICAL: NO (iv) ANTI-SENSE: NO (vii) IMMEDIATE SOURCE:
        (B) CLONE: Primer Oligonuleotide to 5' Leader Sequence of
            IL-1 Receptor (xi) SEQUENCE DESCRIPTION: SEQ ID NO:5:

GCGGATCCCC TCCTGAGAAG CT                                              22

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Primer oligonucleotide (iii) HYPOTHETICAL: NO (iv) ANTI-SENSE: NO (vii) IMMEDIATE SOURCE:
        (B) CLONE: Primer Oligonucleotide Upstream of
            Transmembrane Portion of IL-1 Receptor (xi) SEQUENCE DESCRIPTION: SEQ ID NO:6:

GCGGATCCCA TGTGCTACTG G                                               21

VIRAL VECTORS TO INHIBIT LEUKOCYTE INFILTRATION OR CARTILAGE DEGRADATION OF JOINTS

CROSS-REFERENCE TO RELATED APPLICATION

This is a continuation-in-part application of U.S. application Ser. No. 08/685,212, filed Jul. 23, 1996, which is a continuation of U.S. application Ser. No. 08/027,750, filed Mar. 8, 1993, now abandoned, which was a continuation-in-part of U.S. application Ser. No. 07/630,981, filed Dec. 20, 1990, now abandoned.

BACKGROUND OF THE INVENTION

1. Field of the Invention

The present invention relates to a method of introducing at least one gene encoding a product of interest into at least one cell of a mammalian host for use in treating the mammalian host. This method discloses employing vector molecules containing a gene encoding the product and infecting the target cells of the mammalian host using the vector molecule. Both viral and non-viral means can be used for effecting introduction of the gene into the host.

Numerous methods are within the scope of the invention for effecting introduction of a gene into a host. For example, in vivo methods can be employed to inject a DNA sequence encoding the product of interest into the host, such as through the use of a viral or non-viral vector containing the DNA sequence(s) of interest.

Alternatively, the gene encoding the product of interest can be associated with liposomes and injected directly into the host, such as in the area of the joint, where the liposomes fuse with target cells, resulting in an in vivo gene transfer to the connective tissue. In another embodiment, the gene encoding the product of interest is introduced into the area of the joint as naked DNA. The naked DNA enters the target cells, resulting in an in vivo gene transfer to the cells.

In vitro methods of introducing a gene of interest into a host are also within the scope of this invention. For example, the host's own connective tissue cells can be transduced in vitro with the gene of interest and introduced back into the host, such as through intraarticular injection or other methods known to those skilled in the art.

As an alternative, non-connective tissue cells such as hematopoietic progenitor cells, stromal cells, bone marrow cells, myoblasts, leukocytes and mature lymphoid or myeloid cells may be transfected in vitro, recovered, and injected into the bone marrow or bloodstream of the host using techniques known to the skilled artisan.

The present invention also relates to a method for treating a connective tissue of a host of introduction of at least one gene encoding a product of interest to at least one joint of the host, such that a therapeutic benefit is realized both in the treated joint and in untreated joints of the same host.

The methods of the present invention for introducing a gene of interest into a host result in the expression of the gene within the host such that a therapeutic benefit is realized. Such benefit can be seen not only in the targeted joint, but in other joints of the host as well. Enhanced therapeutic benefits are realized when two or more genes are used together.

BRIEF DESCRIPTION OF THE RELATED ART

Arthritis involves inflammation of a joint that is usually accompanied by pain and frequently changes in structure.

Arthritis may result from or be associated with a number of conditions including infection, immunological disturbances, trauma and degenerative joint diseases, such as osteoarthritis. The biochemistry of cartilage degradation in joints and cellular changes have received considerable investigation.

In a healthy joint, cells in cartilage (chondrocytes) and the surrounding synovium (synoviocytes) are in a resting state. In this resting state, these cells secrete basal levels of prostaglandins, cytokines and various proteinases, such as collagenase, gelatinase and stromelysin, with the ability to degrade cartilage. During the development of an arthritic condition, these cells become activated. In the activated state, synoviocytes and chondrocytes synthesize and secrete large amounts of prostaglandins, cytokines and proteinases.

In efforts to identify pathophysiologically relevant cell activators, it has been known that the cytokine interleukin-1 activates chondrocytes and synoviocytes and induces cartilage breakdown in vitro and in vivo. Additionally, interleukin-1 is a growth factor for synoviocytes and promotes their synthesis of matrix, two properties suggesting the involvement of interleukin-1 in the synovial hypertrophy that accompanies arthritis. In contrast, interleukin-1 inhibits cartilaginous matrix synthesis by chondrocytes, thereby suppressing repair of cartilage. Interleukin-1 also induces bone resorption and thus may account for the loss of bone density seen in rheumatoid arthritis. Interleukin-1 is inflammatory, serves as a growth factor for lymphocytes, is a chemotactic factor and a possible activator of polymorphonuclear leukocytes (PMNs). When present in a sufficient concentration, interleukin-1 may cause fever, muscle wasting and sleepiness.

The major source of interleukin-1 in the joint is the synovium. Interleukin-1 is secreted by the resident synoviocytes, which are joined under inflammatory conditions by macrophages and other white blood cells.

Much attention has been devoted to the development of a class of agents identified as the "Non-Steroidal Anti-Inflammatory Drugs" (hereinafter "NSAIDs"). The NSAIDs inhibit cartilage synthesis and repair and control inflammation. The mechanism of action of the NSAIDs appear to be associated principally with the inhibition of prostaglandin synthesis in body tissues. Most of this development has involved the synthesis of better inhibitors of cyclo-oxygenase, a key enzyme that catalyzes the formation of prostagladin precursors (endoperoxides) from arachidonic acid. The anti-inflammatory effect of the NSAIDs is thought to be due in part to inhibition of prostaglandin synthesis and release during inflammation. Prostaglandins are also believed to play a role in modulating the rate and extent of leukocyte infiltration during inflammation. The NSAIDs include drugs such as acetylsalicylic acid (asprin), fenoprofen calcium (Nalfon®Pulvules®, Dista Products Company), ibuprofen (Motrin®, The upjohn Company), and indomethacin (Indocin®, Merck and Company, Inc.).

Therapeutic intervention in arthritis is hindered by the inability to target drugs, such as the NSAIDs, to specific areas within a mammalian host, such as a joint. Traditional routes of drug delivery, such as oral, intravenous or intramuscular administration, depend upon vascular perfusion of the synovium to carry the drug to the joint. This is inefficient because transynovial transfer of small molecules from the synovial capillaries to the joint space occurs generally by passive diffusion. This diffusion is less efficient with increased size of the target molecule. Thus, the access of large drug molecules, for example proteins, to the joint space is substantially restricted. Intra-articular injection of drugs circumvents those limitations; however, the half-life of drug administered intraarticularly is generally short. Another disadvantage of intra-articular injection of drugs is that frequent repeated injections are necessary to obtain acceptable drug levels at the joint spaces for treating a chronic condition such as, for example, arthritis. Because therapeutic agents heretofore could not be selectively targeted joints, it was necessary to expose the mammalian host to systemically high concentrations of drugs in order to achieve a sustained, intra-articular therapeutic dose. Exposure of non-target organs in this manner exacerbated the tendency of anti-arthritis drugs to produce serious side affects, such as gastrointestinal upset and changes in the hematological, cardiovascular, hepatic and renal systems of the mammalian host.

It has been shown that genetic material can be introduced into mammalian cells by chemical or biological means. Moreover, the introduced genetic material can be expressed so that high levels of a specific protein can be synthesized by the hot cell. Cells retaining the introduced genetic material may include an antibiotic resistance gene thus providing a selectable marker for preferential growth of the transduced cell in the presence of the corresponding antibiotic. Chemical compounds for inhibiting the production of interleukin-1 are also known.

U.S. Pat. No. 4,778,806 discloses a method in inhibiting the production of interleukin-1 by monocytes and/or macrophages in a human by administering through the parenteral route a 2-2'-[1,3-propan-2-onediyl-bis (thio)] bis-1 H-imidazole or a pharmaceutically acceptable salt thereof. This patent discloses a chemical compound for inhibiting the production of interleukin-1. By contrast, in one embodiment of the present invention, gene therapy is employed that is capable of binding to an neutralizing interleukin-1.

U.S. Pat. No. 4780,470 discloses a method of inhibiting the production of interleukin-1 by monocytes in a human by administering a 4,5-diaryl-2 (substituted) imidazole. This patent also discloses a chemical compound for inhibiting the production of interleukin-1.

U.S. Pat. No. 4,794,114 discloses a method of inhibiting the 5-lipoxygenase pathway in a human by administering a diaryl-substituted imidazole fused to a thiazole, pyrolidine or piperidine ring or a pharmaceutically acceptable salt thereof. This patent also discloses a chemical compound for inhibiting the production of interleukin-1.

U.S. Pat. No. 4,870,101 discloses a method for inhibiting the release of interleukin-1 and for alleviating interleukin-1 mediated conditions by administering an effective amount of a pharmaceutically acceptable anti-oxidant compound such as disulfiram, tetrakis [3-(2,6-di-tert-butyl-4-hydroxyphenyl) propionyloxy methyl] methane or 2,4-di-isobutyl-6-(N,N-dimethylamino methyl)-phenol. This patent discloses a chemical compound for inhibiting the release of interleukin-1.

U.S. Pat. No. 4,816,436 discloses a process for the use of interleukin-1 as an anti-arthritic agent. This patent states that interleukin-1, in association with a pharmaceutical carrier, may be administered by intra-articular injection for the treatment of arthritis or inflammation. In contrast, the present invention discloses method of using and preparing a gene that is capable of binding to an neutralizing interleukin-1 as a method of resisting arthritis.

U.S. Pat. No. 4,935,343 discloses an immunoassy method for the detection of interleukin-1 beta that employs a monoclonal antibody that binds to interleukin-1 beta but does not bind to interleukin-1 beta. This patent discloses that the monoclonal antibody binds to interleukin-1 beta and blocks the binding of interleukin-1 beta to interleukin-1 receptors, and thus blocking the biological activity of interleukin-1 beta. The monoclonal antibody disclosed in the patent may by obtained by production of an immunogen through genetic engineering using recombinant DNA technology. The immunogen is injected into a mouse and there-after spleen cells of the mouse are immortalized by fusing the spleen cells with myeloma cells. The resulting cells include the hybrid continuous cell lines (hybridomas) that may be later screened for monoclonal antibodies. This patent states that the monoclonal antibodies of the invention may be used therapeutically, such as for example, in the immunization of a patient, or the monoclonal antibodies may be bound to a toxin to form an immunotoxin or the a radioactive material or drug to form a radio pharmacetucal or pharmaceutical.

U.S. Pat. No. 4,766,069 discloses a recombinant DNA cloning vehicle having a DNA sequence comprising the human interleukin-1 gene DNA sequence. This patent provides a process for preparing human interleukin-1 beta, and recovering the human interleukin-1 beta. This patent discloses use of interleukin-1 as an immunological reagent in humans because of its ability to stimulate T-cells and B-cells and increase immunoglobulin synthesis.

U.S. Pat. No. 4,396,601 discloses a method for providing mammalian hosts with additional genetic capability. This patent provides that host cells capable of regeneration are removed from the host and treated with genetic material including at least one marker which allows for selective advantage for the host cells in which the genetic material is capable of expression and replication. This patent states that the modified host cells are then returned to the host under regenerative conditions.

U.S. Pat. No. 4,968,607 discloses a DNA sequence encoding a mammalian interleukin-1 receptor protein which exhibits interleukin-1 binding activity.

U.S. Pat. No. 5,081,228 discloses a DNA sequence encoding both the murine and human interleukin-1 receptor. This patent also provides a process for the in vitro expression of said DNA sequences.

Patent application WO9634955 discloses a method of treating an arthritic condition using recombinantly modified articular chondrocytes.

U.S. Pat. No. 5,643,752 discloses a host cell transformed with an expression vector containing nucleic acid amino acids 30–224 of the TIMP-4 polypeptide.

Patent application WO9723639 discloses expression vectors containing DNA encoding a protein having a the formula X-X-B, where A and B are subunits of a dimeric protein or are each a biologically active protein; X is a linker polypeptide. Transformed hosts containing the vectors are also disclosed. The method reportedly can be used for the production of interleukin-12 using DNA coding for the 40 Kd and 35 Kd subunits of IL-12, joined by a suitable liner.

Patent application WO9700958 discloses an isolated nucleic acid encoding pCL13, a member of TGF-β family member, having ummunosuppressant, cell differentiation promoting and anit-proliferative activities.

In spite of these disclosures, there remains a very real and substantial need for a method for introducing at least one gene encoding a product of interest into at least one cell of a mammalian host in vitro, or alternatively in vivo, for use in treating the mammalian host. There is also a need for such a method in which treatment of one joint results in a therapeutic benefit being realized in non-treated joints as well.

SUMMARY OF THE INVENTION

The present invention has met the above described needs by providing methods for introducing at least one gene encoding a product into at least one cell of a mammalian host for use in treating the mammalian host. These methods include employing recombinant techniques to produce a vector molecule containing the gene encoding for the product of interest, and infecting the target cell of the mammalian host with the vector molecule containing the gene. The vector molecule can be any molecule capable of being delivered and maintained within the target cell or tissue such that the gene encoding the product of interest can be stably expressed. The vector molecule preferably utilized in the present invention is either a viral or retroviral vector molecule or a plasmid DNA non-viral molecule. This method preferably includes introducing the gene encoding the product into the cell of the mammalian connective tissue for a therapeutic or prophylactic use. Unlike previous pharamacological efforts, the methods of the present invention employ gene therapy to address the chronic debilitating effects of joint pathologies.

More specifically, the methods of the present invention include employing one or more genes that encode for at least one of the members selected from the group consisting of (a) a human interleukin-1 receptor antagonist protein (IRAP); (b) a Lac Z marker gene capable of encoding a beta-galactosidase protein; (c) a soluble interleukin-1 receptor protein (sIL-1R); (d) a soluble TNA-$\alpha$ receptor protein (sTNF-$\alpha$R); (e) a proteinase inhibitor; (f) a therapeutic cytokine; (g) CTLA4; (h) FasL: (i) an anti-adhesion molecule; and (j) a free radical antagonist. Biologically active derivatives and fragments of these genes and/or the proteins they encode are also within the scope of the present invention.

The viral vectors used in the methods of the present invention can be selected form the group consisting of (a) a retroviral vector, such as MFG or pLJ; (b) an adeno-associated virus; (c) an adenovirus; and (d) a herpes virus, including but not limited to herepes simplex 1 or herpes simples 2.

Alternatively, a non-viral vector, such as a DNA plasmid vector, can be used. Any DNA plasmid vector known to one of ordinary skill in the art capable of stable maintenance within the targeted cell or tissue upon delivery, regardless of the method of delivery utilized is within the scope of the present invention.

Non-viral means for introducing the gene encoding for the product into the target cell are also within the scope of the present invention. Such non-viral means can be selected from the group consisting of (a) at least one liposome, (b) $Ca_3(PO_4)_2$, (c) electroporation, (d) DEAE-dextran, and (e) injection of naked DNA.

An additional method for introducing at least one gene encoding a product into at least one cell of a mammalian host for use in treating the mammalian host utilizes biological means such as a virus. Preferably, the virus is a pseudo-type retrovirus, the genome having been altered such that the pseudo-type retrovirus is capable only of delivery and stable maintenance within the target cell, but not retaining an ability to replicate within the target cell or tissue. The altered viral genome is further manipulated by recombinant DNA techniques such that the viral genome acts as a DNA vector molecule containing the gene of interest to be expressed within the target cell or tissue.

A further embodiment of this invention includes a method to produce an animal model for the study of connective tissue pathologies which includes introducing at least one gene encoding a product into at least one cell of a mammalian host.

In a specific method disclosed as an example of the animal model, and not as a limitation to the present invention, a DNA plasmid vector containing the interleukin-1 beta coding sequence was ligated downstream of the cytomegalovirus (CMV) promoter. This DNA plasmid construction was encapsulated within iposomes and injected intraarticularly into the knee joints of recipient rabbits. Interleukin-1 beta (IL-1$\beta$) was expressed and significant amounts of interleukin-1 beta were recovered from the synovial tissue. An alternative is injection of the naked plasmid DNA into the knee joint, allowing direct transfection of the DNA into the synovial tissue. Injection of IL-1$\beta$ into the joint of a mammalian host allows for prolonged study of various joint pathologies and systemic indices of inflammation, as described within this specification.

A preferred method of using the genes of this invention involves employing recombinant techniques to generate a cell line which produces infectious retroviral particles containing the gene encoding for the product of interest. The producer cell line is generated by inserting the gene into a retroviral vector under the regulation of a suitable eukaryotic promoter, transfecting the retroviral vector containing the gene into the retroviral packaging cell kine for the production of a viral particle that is capable of expressing the gene, and infecting synovial cells of a mammalian host using the viral particle. Infection can be accomplished directly by intra-articular injection into a joint space of a mammalian host that is lined with synovial cells. In a preferred embodiment, synoviocytes recovered form the knee joint are cultured in vitro for subsequent utilization as a delivery system for gene therapy. Other connective tissue cells could also be used, as could other non-connective tissue cells, such as skin cells, for in vitro culture techniques. The methods of this invention may be employed both prophylactically and in the therapeutic treatment of arthritis in any susceptible joint.

In another embodiment of this invention, a method of using a gene coding for the soluble interleukin-1 receptor (sIL-1R) involves employing recombinant techniques to generate a cell line which produces infectious viral particles coding for sIL-1R. The producer cell line is generated by inserting the gene into a viral vector under the regulation of a suitable eukaryotic promoter, transfecting the viral vector containing the gene into the viral packaging cell line for the production of a viral particle capable of expressing the gene coding for sIL-1R, and infecting target cells, such as synovial cells, of a mammalian host using the viral particle. The cells can be infected in culture (ex vivo) with viral particles and subsequently transplanted back into the joint, or can be infected in vivo by direct administration of the viral particles to the host joint. This method may be employed in both prophylactic and therapeutic treatment of joint pathologies in any area.

In an example of on embodiment of this invention, recombinant techniques are used to produce a viral vector carrying two genes. The first gene encodes the product of interest, such as the soluble interleukin-1 receptor, and the second gene encodes for selectable antibiotic resistance. This method of use involves transfecting the viral vector into a viral packaging cell line to obtain a cell line producing infectious viral particles carrying the gene.

Another embodiment of this invention provides a method for preparing a gene encoding a product of interest including synthesizing the gene by a polymerase chain reaction, introducing the amplified coding sequence into a retroviral vector, transfecting the retroviral vector into a retrovirus packaging cell line and collecting viral particles from the retrovirus packaging cell line.

In another embodiment of this invention, a compound for parenteral administration to a patient in a therapeutically or prophylactically effective amount is provided that contains a gene encoding a product of interest in a suitable pharmaceutical carrier.

In another preferred embodiment of the invention, connective tissue cells are transfected in vivo following direct intraarticular injection of a DNA molecule containing the gene of interest into the joint. Transfection of the recipient tissue cells according to this embodiment bypasses the requirement of removal, culturing, in vitro transfection, selection and transplanting the DNA vector-containing target cells to promote stable expression of the heterologous gene of interest. Methods of injecting the DNA molecule into the joint include, but are not limited to, association of the DNA molecule with cationic liposomes or the direct injection of the DNA molecule itself into the joint. The DNA molecule, regardless of the form of presentation to the joint, is preferably presented as a vector molecule, either as a viral DNA vector molecule, or more preferably, a DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the host cells. Alternatively, non-connective tissue cells can be targeted in vivo in any of the methods described above.

In another preferred embodiment of this invention, one or more genes are introduced to a first joint of a patient through any of the delivery means described throughout the specification. Expression of the gene(s) in the first joint results in a therapeutically or prophylactically beneficial effect in the first joint. Such a beneficial effect is also observed in other joints of the patient. Thus, the methods of the present invention provide for direct treatment of joints as well as indirect treatment of untreated joints of the same patient.

It is an object of the present invention to provide a method of introducing at least one gene encoding a product into at least one cell of a mammalian host for use in treating the mammalian host.

It is an object of the invention to provide a method of introducing a gene encoding a product into at least one cell of a mammalian host for a therapeutic use.

It is an object of the present invention to provide a method of introducing into the synovial lining cells of a mammalian arthritic joint at least one gene which codes for proteins having therapeutic properties.

It is an object of the present invention to provide an animal model for the study of connective tissue pathology.

It is an object of the present invention to provide a method of introducing, by either ex vivo or in vivo methods, a gene coding for the sIL-1R that is capable of binding to and neutralizing substantially all isoforms of interleukin-1, including interleukin-1 alpha and interleukin-1 beta.

It is an object of the present invention to provide a method of introducing, by higher ex vivo or in vivo methods in a mammalian host, a gene that is capable of binding to and neutralizing substantially all isoforms of interleukin-1 and thus substantially resists the degradation of cartilage and protects surrounding soft tissues of the joint space.

It is an object of the present invention to provide a method of introducing, by either ex vivo or in vivo methods, a gene coding for the sIL-1R that is capable of binding to and neutralizing substantially all isoforms of interleukin- 1 for the prevention of arthritis in patients that demonstrate a high susceptibility for developing the disease.

It is an object of the present invention to provide a method of introducing, by either ex vivo or in vivo methods, a gene coding for an sIL-1R that is capable of binding to and neutralizing substantially all isoforms of interleukin-1 for the treatment of patients with arthritis.

It is an object of the present invention to provide a method of introducing, by either ex vivo or in vivo methods, a gene or genes that address chronic debilitating joint pathophysiologies.

It is a further object of the present invention to provide a compound for parenteral administration to a patient which comprises a gene encoding a product of interest in a suitable pharmaceutical carrier.

Another object of this invention is to provide a method of introducing more than one gene encoding more than one product of interest such that expression of the proteins results in an enhanced therapeutic benefit.

A further object of the present invention is to provide a method for treating at lest one symptom of a connective tissue disorder by treating one joint of a mammalian host, such that a therapeutic benefit is realized in both the treated joint and non-treated joints.

These and other objects of the invention will be more fully understood form the following description of the invention, the referenced drawings and the claims.

BRIEF DESCRIPTION OF THE DRAWINGS

FIGS. 8A–8C show the amino acid and nucleotide sequence of the human (SEQ ID NOS: 1 2) and mouse (SEQ ID NOS: 3–4) interleukin-1receptors.

On Day 4, knees were lavaged with 1 ml saline. On Day 7, rabbits were killed and the knees again lavaged. The concentrations of human IRAP in the lavage fluids were determined by ELISA using a commercial kit (R&D Systems, Minneapolis, Minn.). Values given are means ±S.E. Numbers of knees are shown above each column. Asterisks denote values which differ at p<0.05 (t-test).

Figure 15:
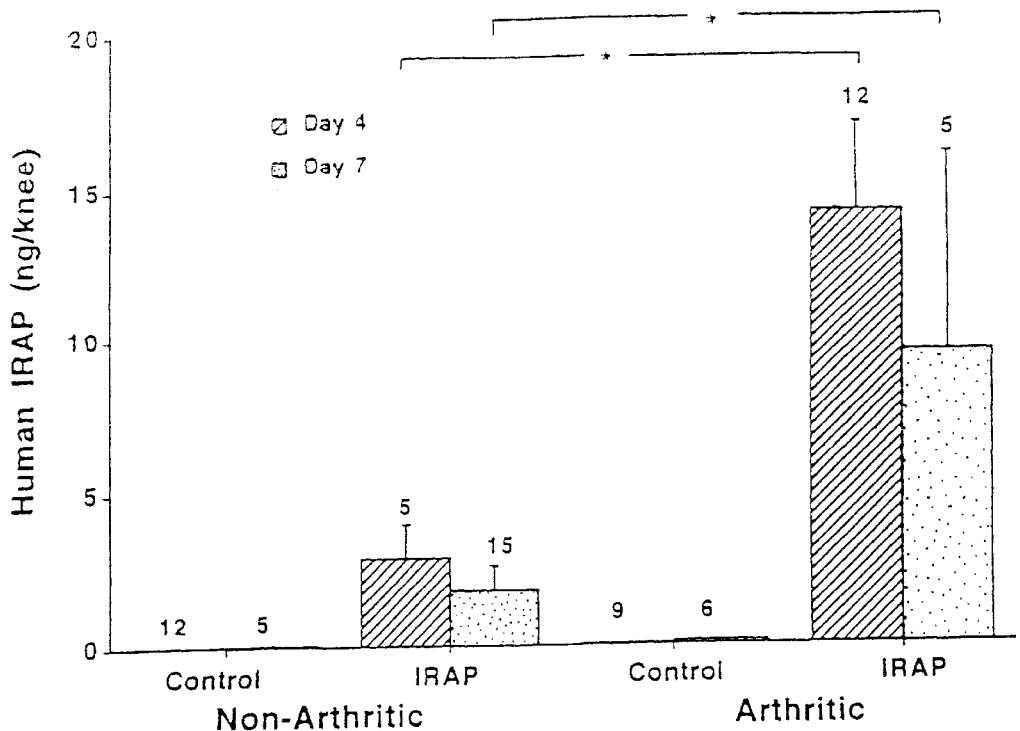
FIG. 15 shows expression of human IRAP in normal and arthritic knees of rabbits. Antigen-induced arthritis was initiated by injecting 5 mg ovalbumin into one knee joint (arthritic knee) of pre-sensitized rabbits on Day 1. The untreated knee (non-arthritic knee) received carrier solution only. On Day 2, autologous synoviocytes ($10^7$/knee in 1 ml saline) were transferred to selected knee joints by intraarticular injection. Certain non-arthritic knees and arthritic knees received cells transduced with the human IRAP gene. Other non-arthritic and arthritic knees received untransduced cells or cells transduced with lac Z and neo$^r$ genes (controls). As the results obtained with these two types of control cells were indistinguishable, they have been pooled in the figures. Detailed methods for synoviocytes culture, transduction and intraarticular implantation are disclosed throughout this specification.
Figure 16:
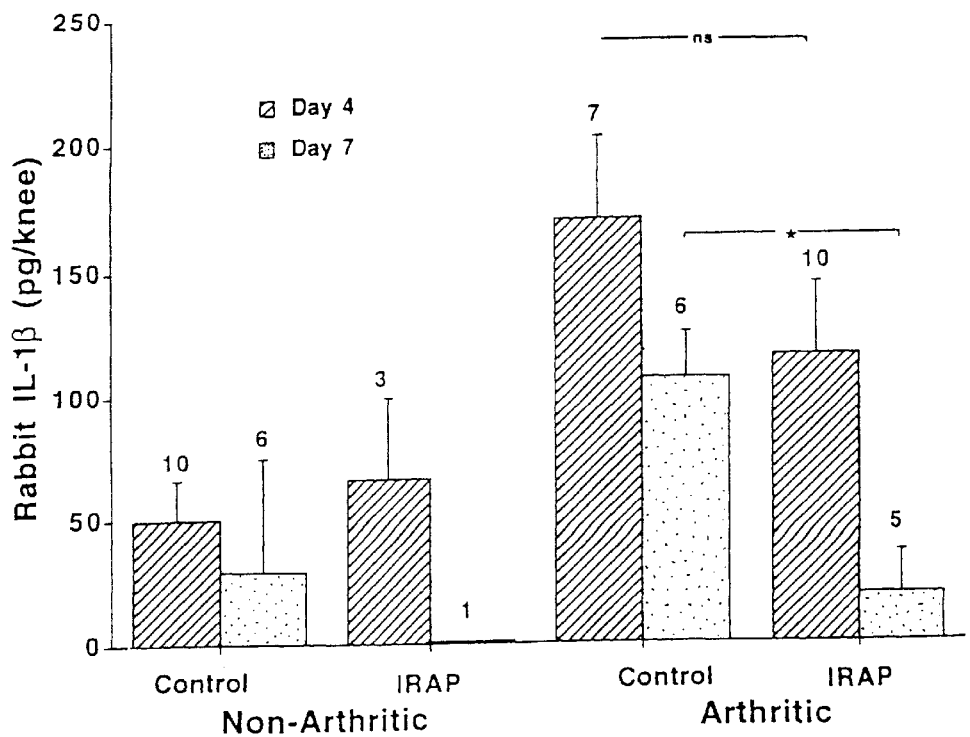

FIG. 16 shows concentrations of rabbis IL-1β in the normal and arthritic knee joints of rabbits. Experimental conditions were identical to those described in FIG. 15. However, lavage fluids were assayed for rabbit IL-1α and rabbit IL-1β by RIA using a commercial kit (Cytokine Sciences, Boston, Mass.). Low levels of IL-1β are present in non-arthritic knees as a reflection of the slight inflammatory effects provoked by intraarticular injection. No IL-1α was detectable in any of the samples. Values given are means ±S.E. Numbers of knees are shown above each column. Asterisks denote values which differ at p<0.05 (t-test).

Figure 17A:
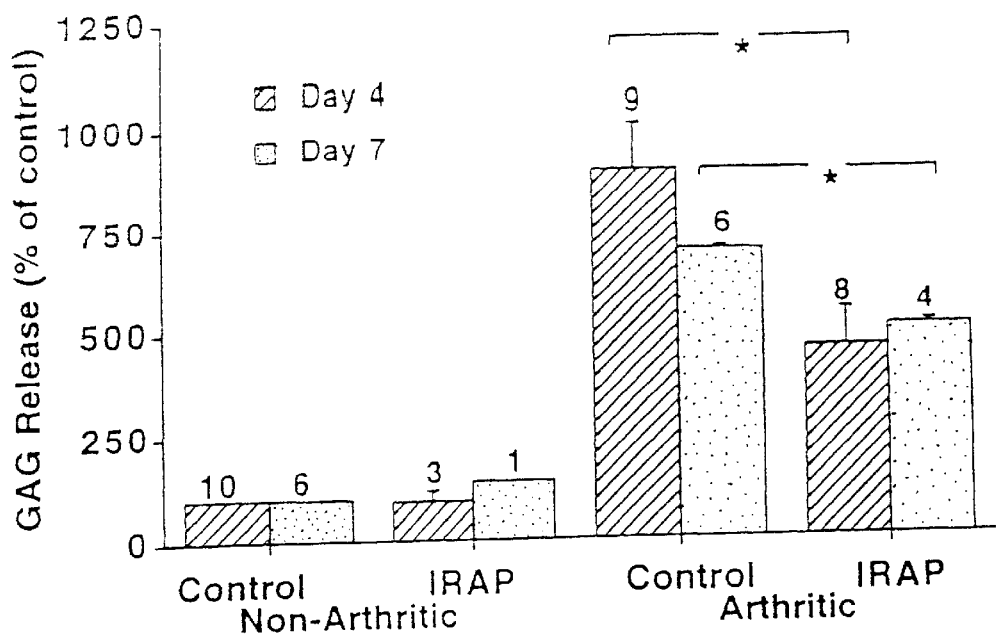
Figure 17B:
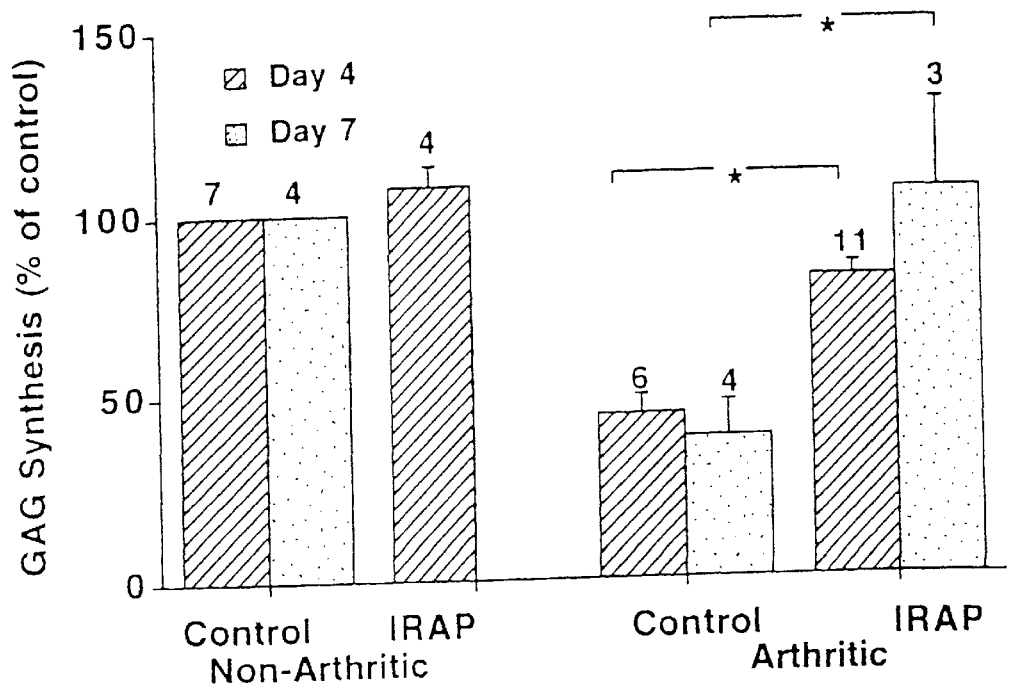

FIG. 17(A–B) shows the effect of IRAP gene transfer on cartilage matrix metabolism. Experimental conditions were as described for FIG. 15, except that rabbits were killed both at days 4 and 7. GAG concentrations in the lavage fluids (FIG. 17a) were measured spectrophotometrically by the dimethymethylene blue assay (Farndale, et al., Biochim. Biophys. Acta. 883:173–177 (1986)). Fragments of articular cartilage were shaved from the femoral condyles of the knees and GAG synthesis (FIG. 17b) was measured as the uptake of $^{35}SO_4^{2-}$ into macromolecular material as described (Taskiran, et al., Biochem. Biphys. Res. Commun. 200:1442–148 (1994)). Results are shown in each case as percent of control. Values given are means ±S.E. Numbers of knees are shown above each column.

Figure 18:
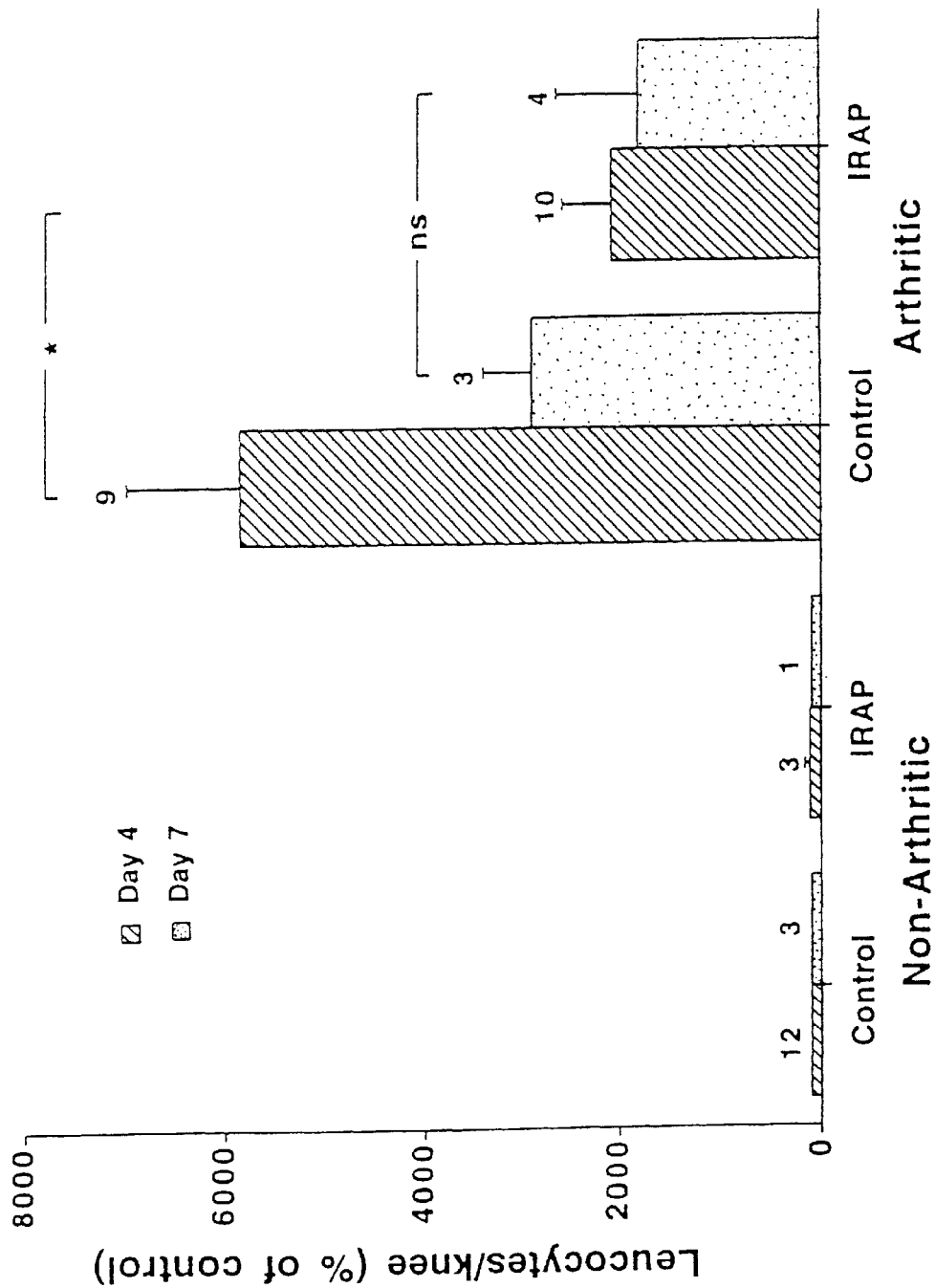

FIG. 18 shows effects of IRAP gene transfer on leukocytosis. Experimental conditions ere identical to those described in FIG. 15. Numbers of leukocytes in the lavage fluids ere determined with a hemocytometer. Values shown are means ±S.E. Numbers of knees are shown above each column. Asterisks denote values which differ at p<0.05 (t-test).

Figure 19:
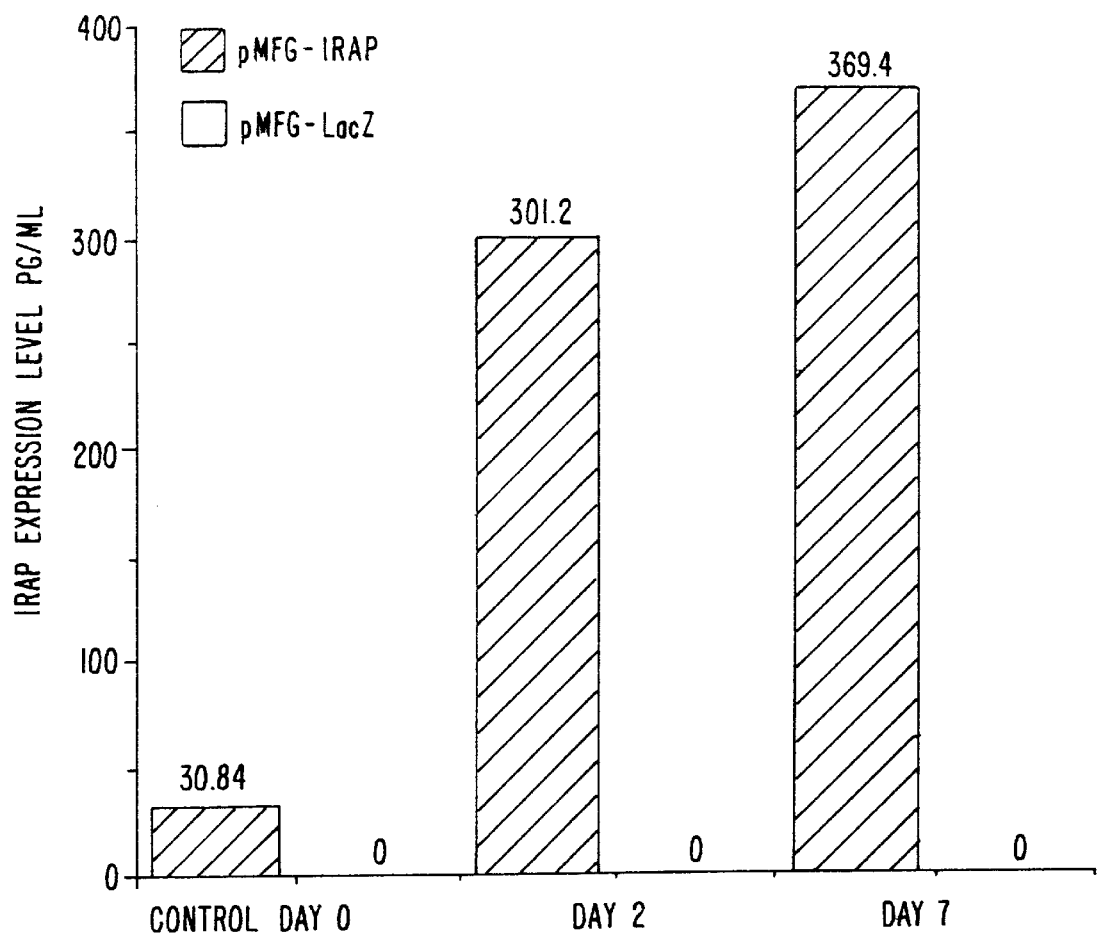

FIG. 19 shows the levels of IRAP expressed in the rabbit knee 0,2 and 7 days after intraarticular injection of MFG-IRAP vectors, determined according to the method of Example XVI.

Figure 20A:
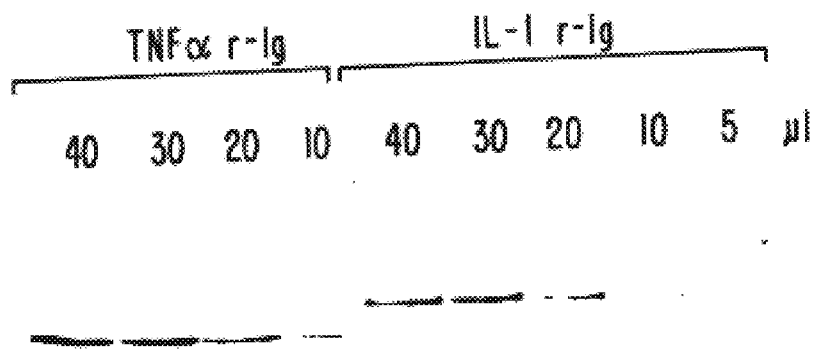
Figure 20B:
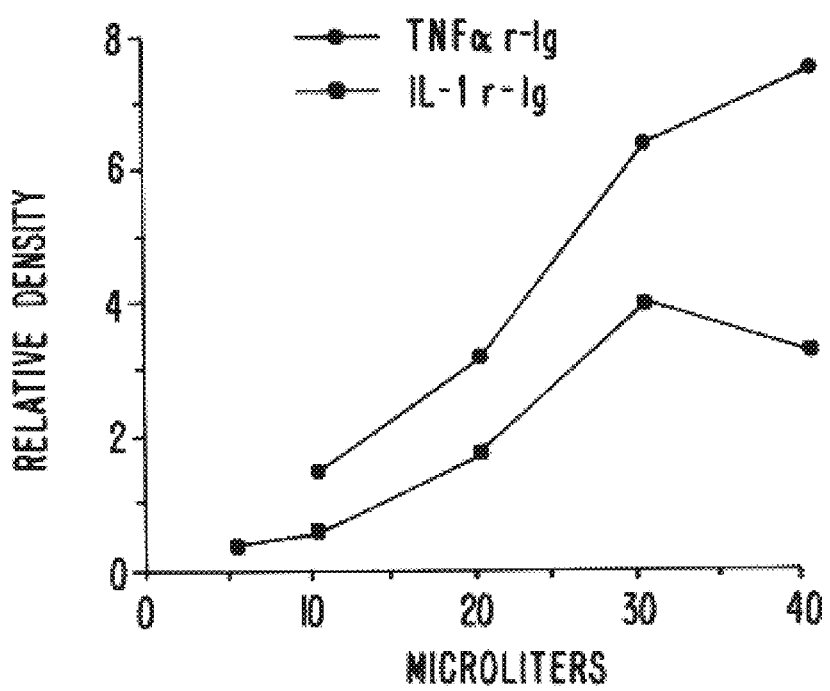

FIG 20a shows the ELISA measurements of the sTNF-αR and sIL-1R taken from rabbit knees according to the method of Example XVII. FIG. 20b plots the relative density versus microliters of sTNF-αR-Ig and sIL-1R-Ig taken from rabbit knees according to the method of Example XVII.

Figure 21:
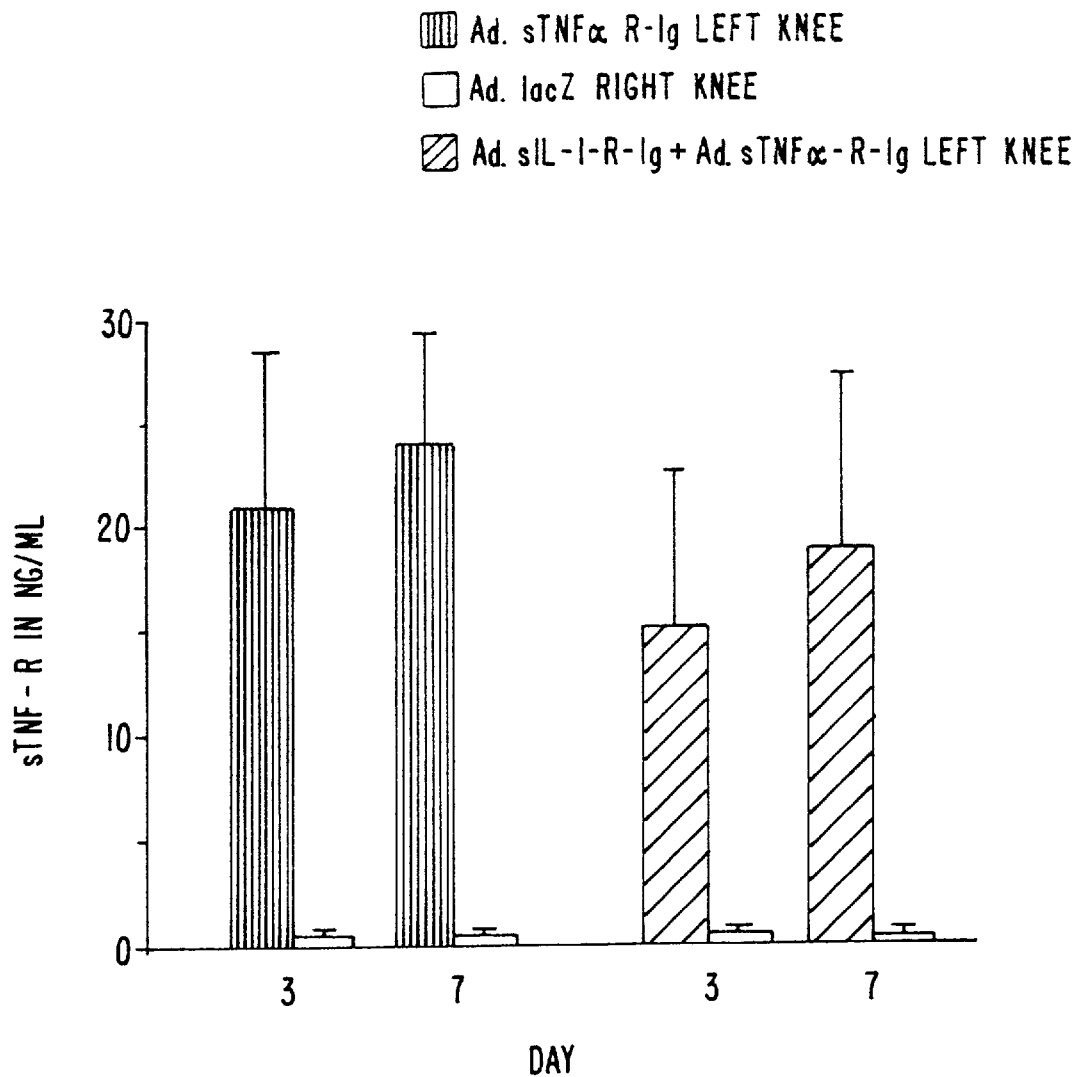

FIG. 21 shows the level of sTNF-αR expression in rabbit knees injected with Ad.sTNF-αR-Ig, Ad.lacZ, or Ad.sIL-1R-Ig and AD.sTNF-α-Ig determined according to the method of Example XVII.

Figure 22A:
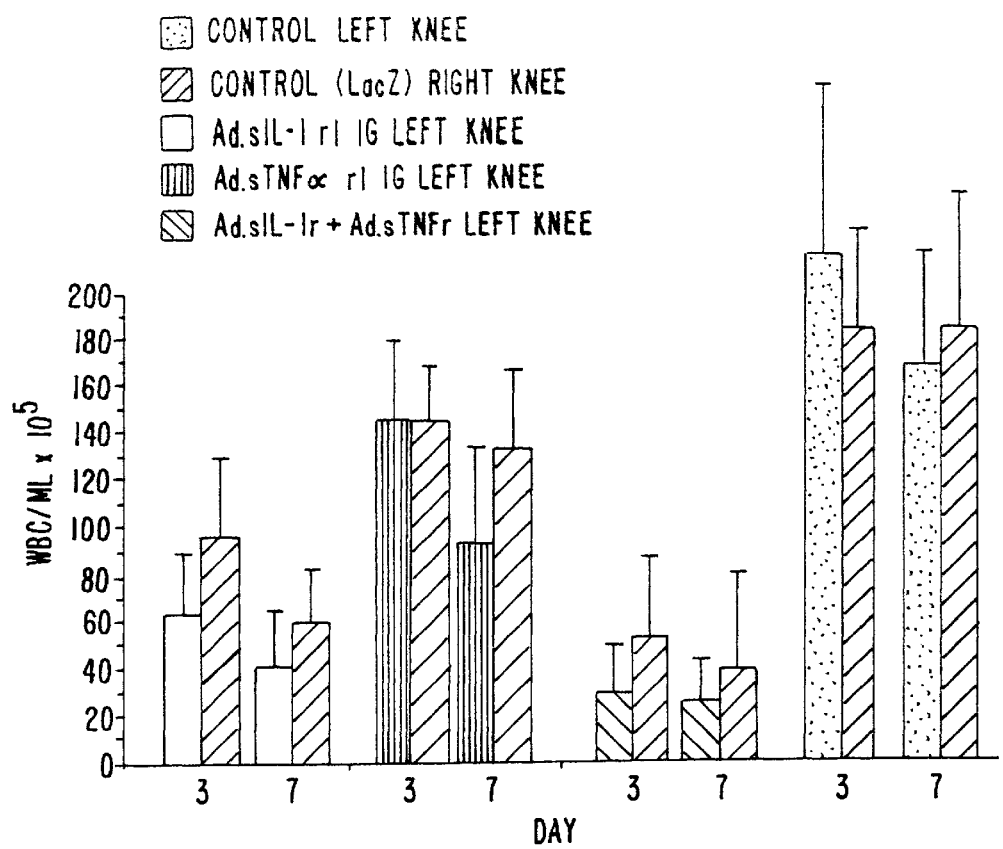
Figure 22B:
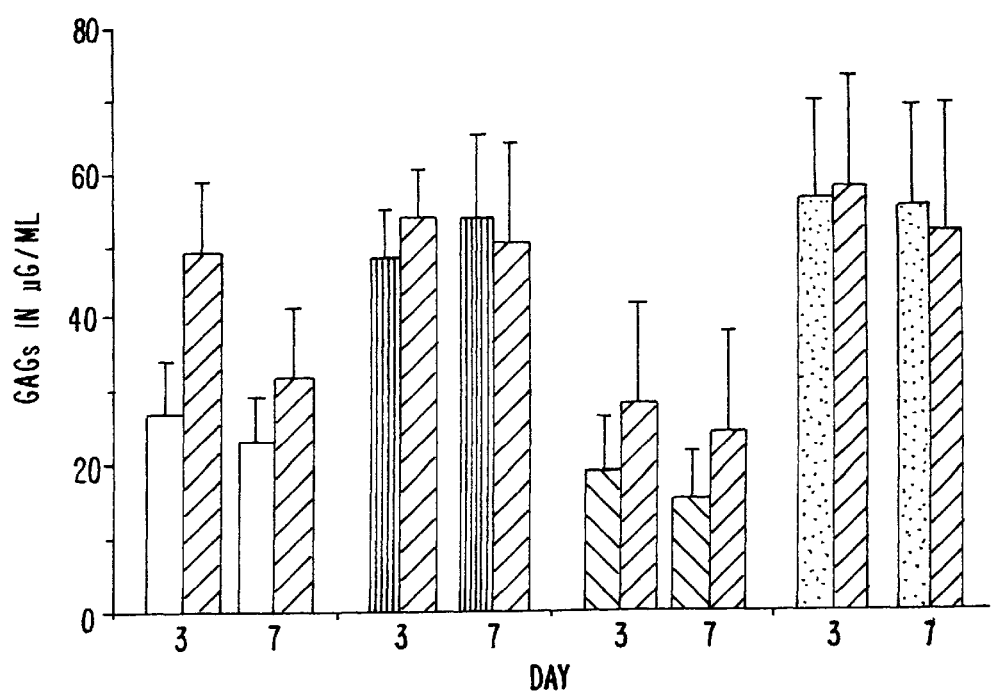
Figure 23A:
Figure 23B:
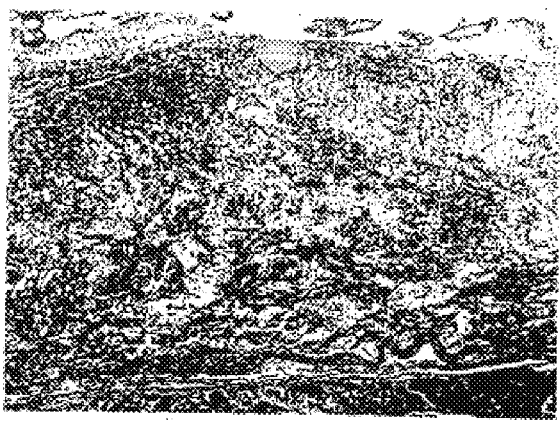
Figure 23C:
Figure 23D:
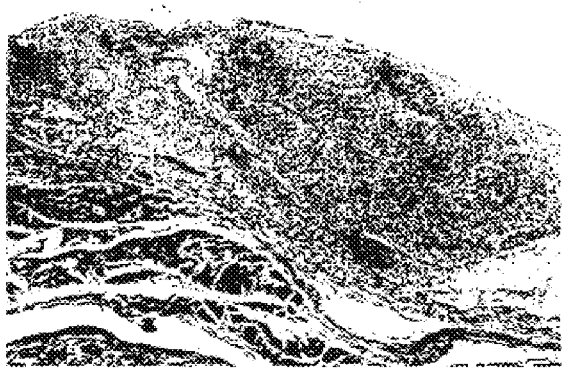
Figure 23E:
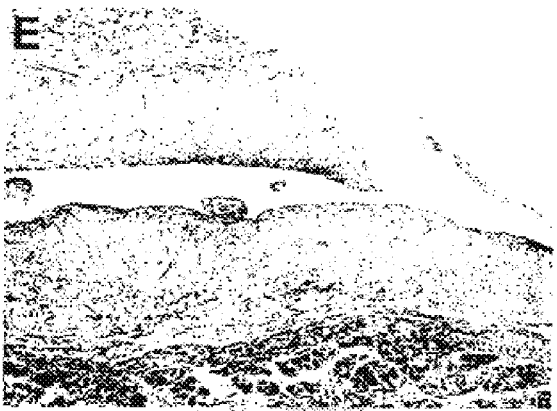
Figure 23F:
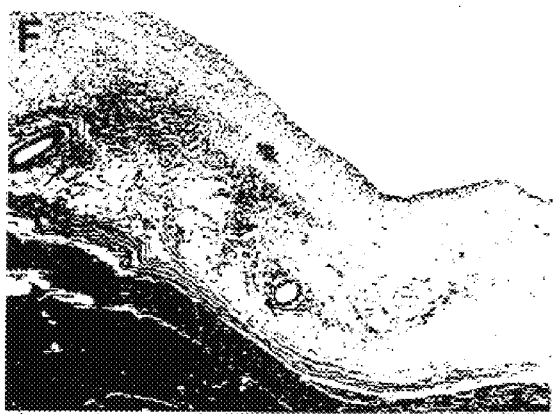
Figure 23G:
Figure 23H:

FIGS. 22(A–B) 22a shows the white blood cell count ×$10^5$ in rabbit knees measured 3 and 7 days after injection determined according to the method of Example XVII. FIG. 22b shows the GAG levels in rabbit knees measured 3 and 7 days after injection determined according to the method of Example XVII.

FIGS. 23(A–H) shows the results of a histological analysis of synovial tissue recovered form rabbit knees, determined according to the method of Example XVII.

Figure 24:
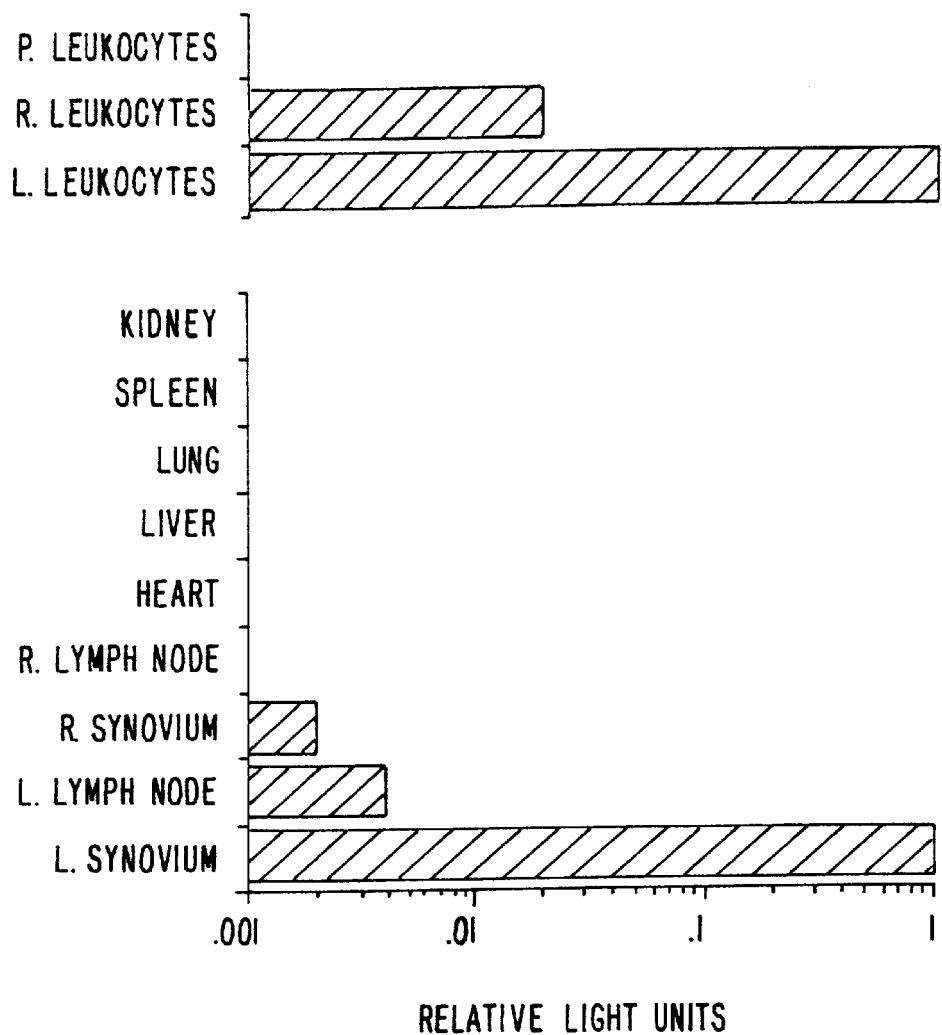

FIG. 24 shows expression of luciferase activity in various tissues following intraarticular injection of Ad.luciferase into a.i.a. knees, determined according to the method of Example XVII.

Figure 25:
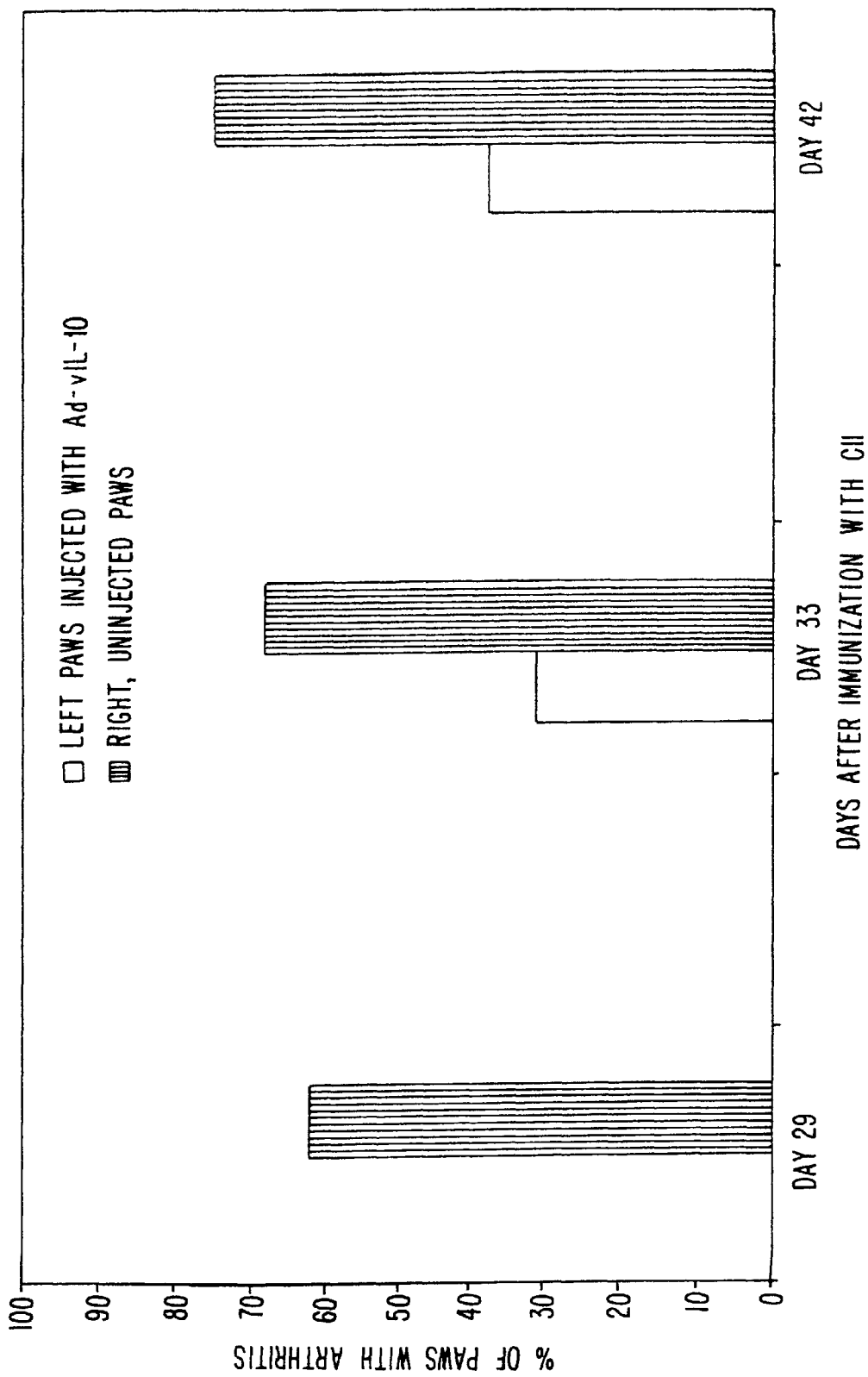

FIG. 25 shows a bar graph of % paws with arthritis following injection of left side paws with Ad.vIL-10, determined according to the methods of Example XVIII.

Figure 26:
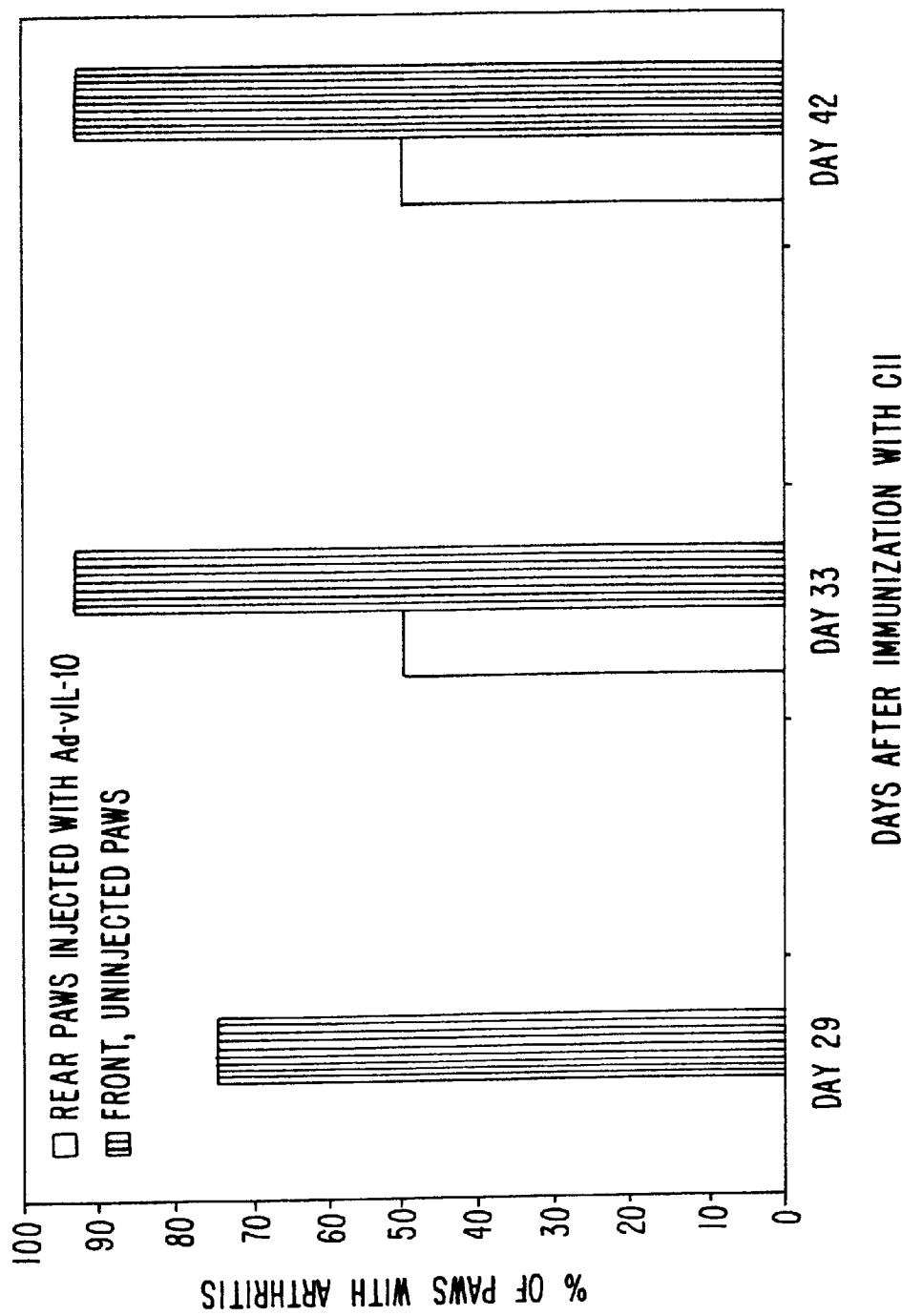

FIG. 26 shows a bar graph of % paws with arthritis following injection of Ad.vIL-10 in rear paws, determined according to the methods of Example XVIII.

Figure 27:
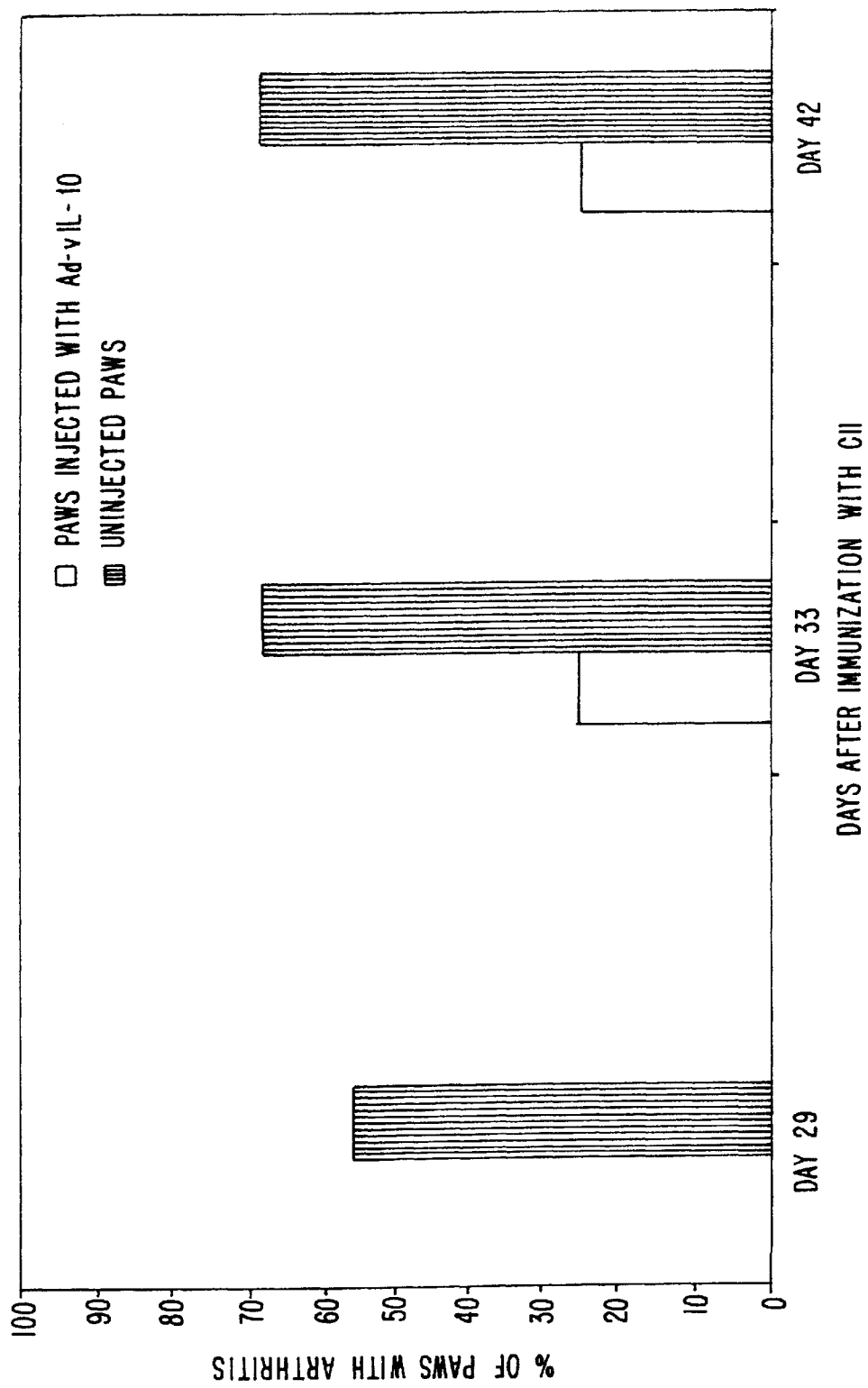

FIG. 27 shows a bar graph of % paws with arthritis following injection of Ad.vIL-10 in front right and left rear paws, determined according to the methods of Example XVIII.

Figure 28:
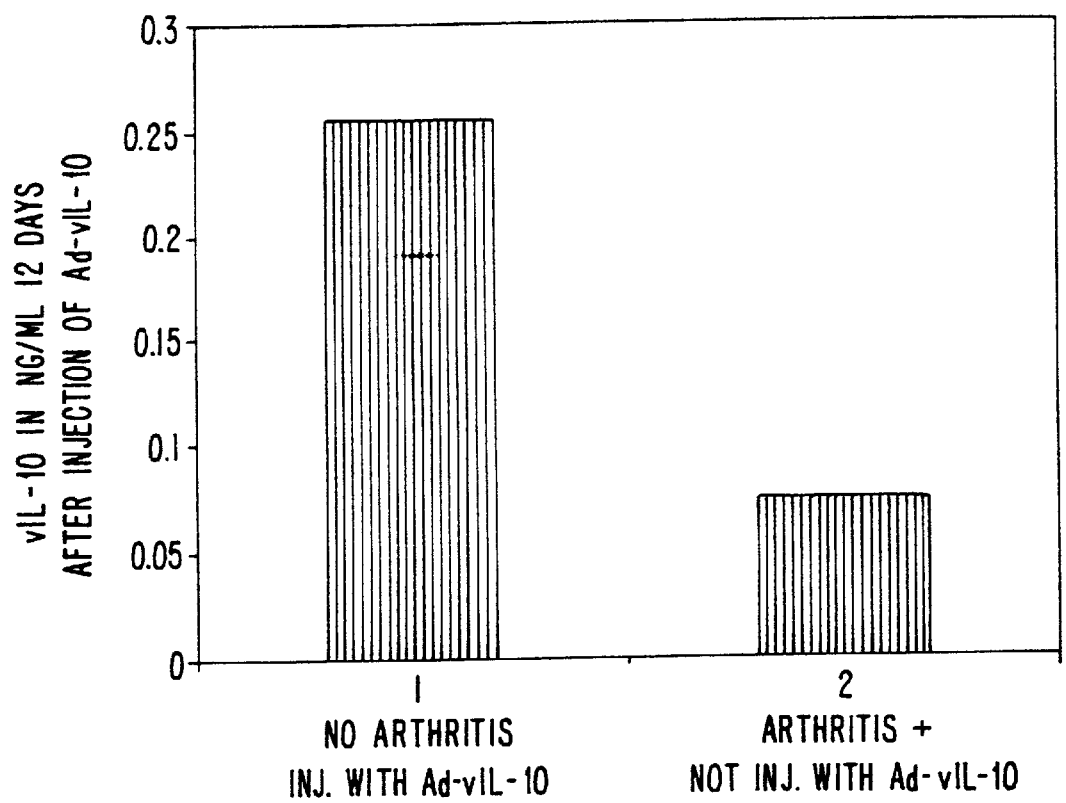

FIG. 28 compares vIL-10 expression in a paw injected with Ad.vIL-10 and protected against arthritis to vIL-10 expression in a control paw, determined according to the methods of Example XVIII.

Figure 29:
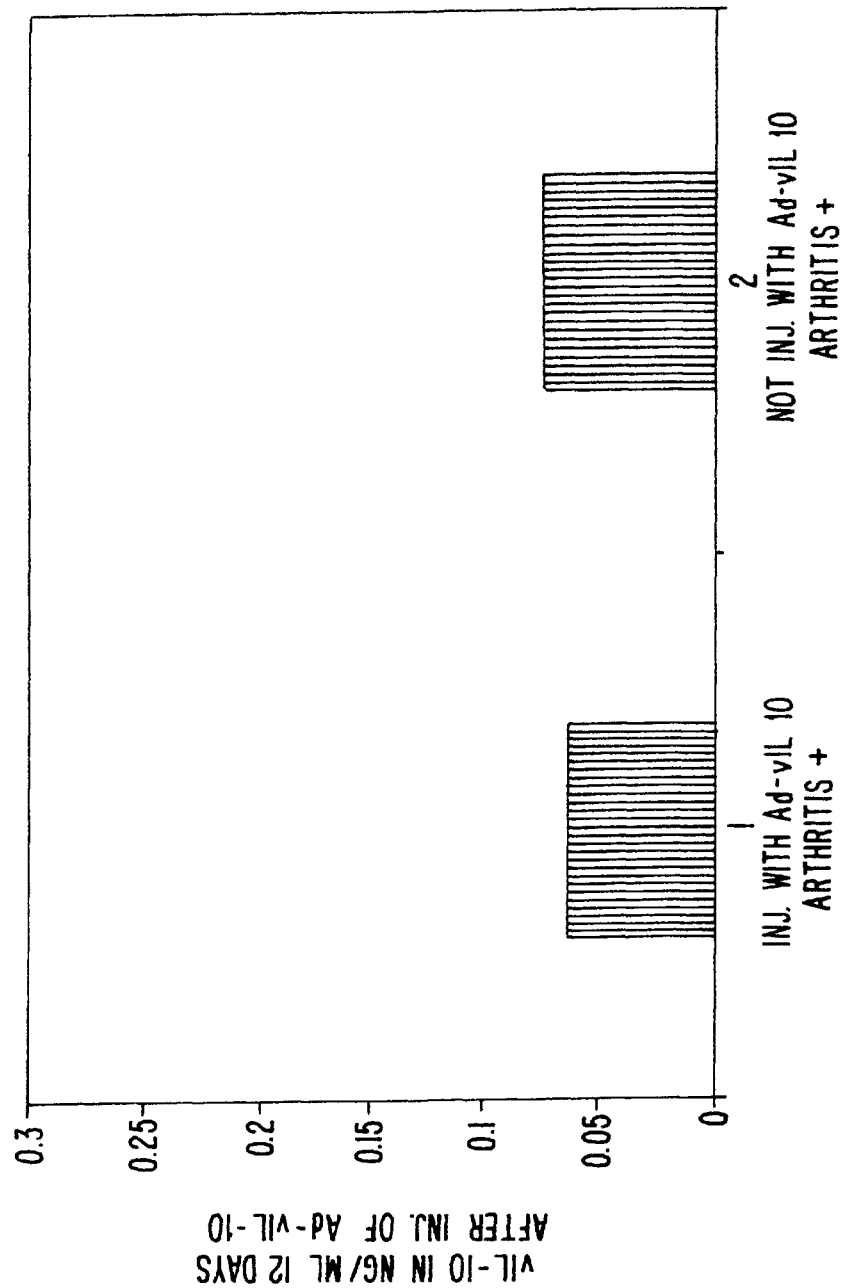

FIG. 29 compares vIL-10 expression in a paw injected with Ad.vIL-10 and not protected against arthritis to vIL-10 expression in a control paw, determined according to the methods of Example XVIII.

Figure 30:
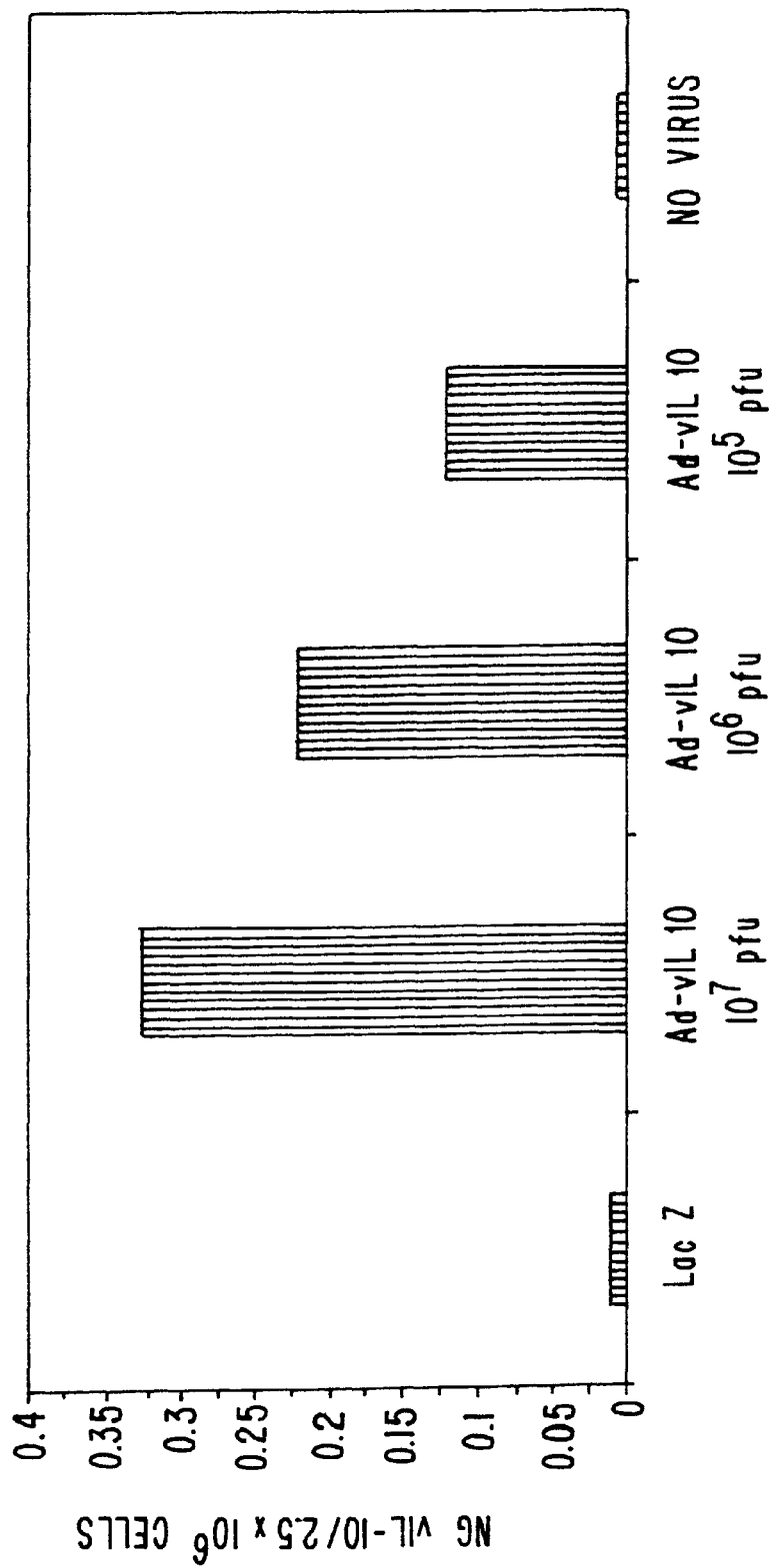

FIG. 30 shows a bar graph of vIL-10 expression in lymph nodes of mice injected in vivo with Ad.vIL-10, determined according to the methods of Example XVIII.

Figure 31A:
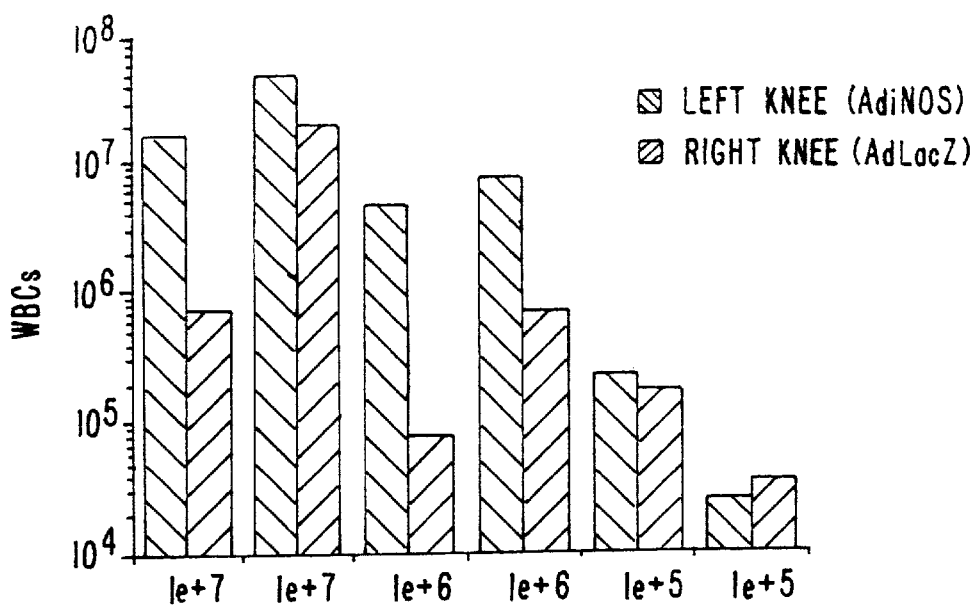

FIG. 31a shows the white blood cell counts in Ad.iNOS knees and Ad.LacZ knees determined according to the methods of Example XIX.

Figure 31B:
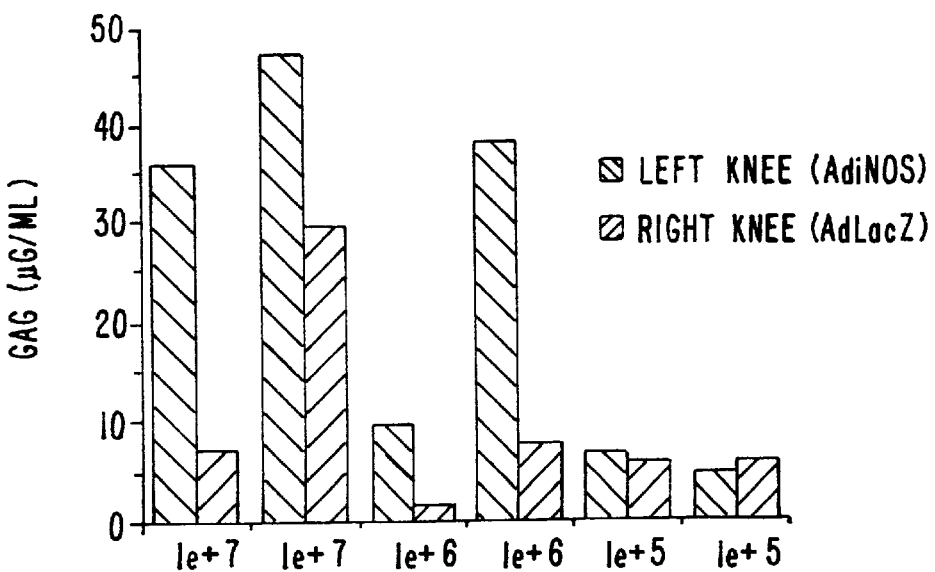

FIG. 31b shows the GAG release in Ad.iNOS and Ad.LacZ knees determined according to the methods of Example XIX.

Figure 32:
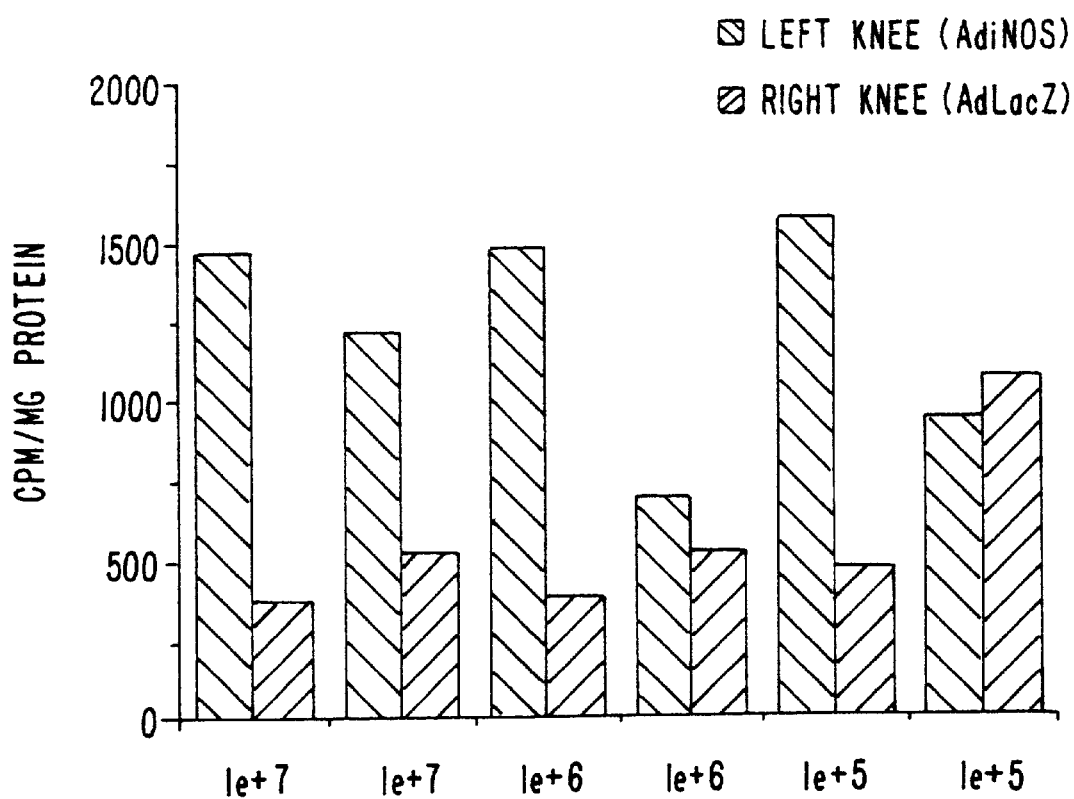

FIG. 32 shows the NO synthase in counts per minute per milligram (CPM/mg) of protein in Ad.iNOS and Ad.LacZ knees, determined according to the methods of XIX.

Figure 33:
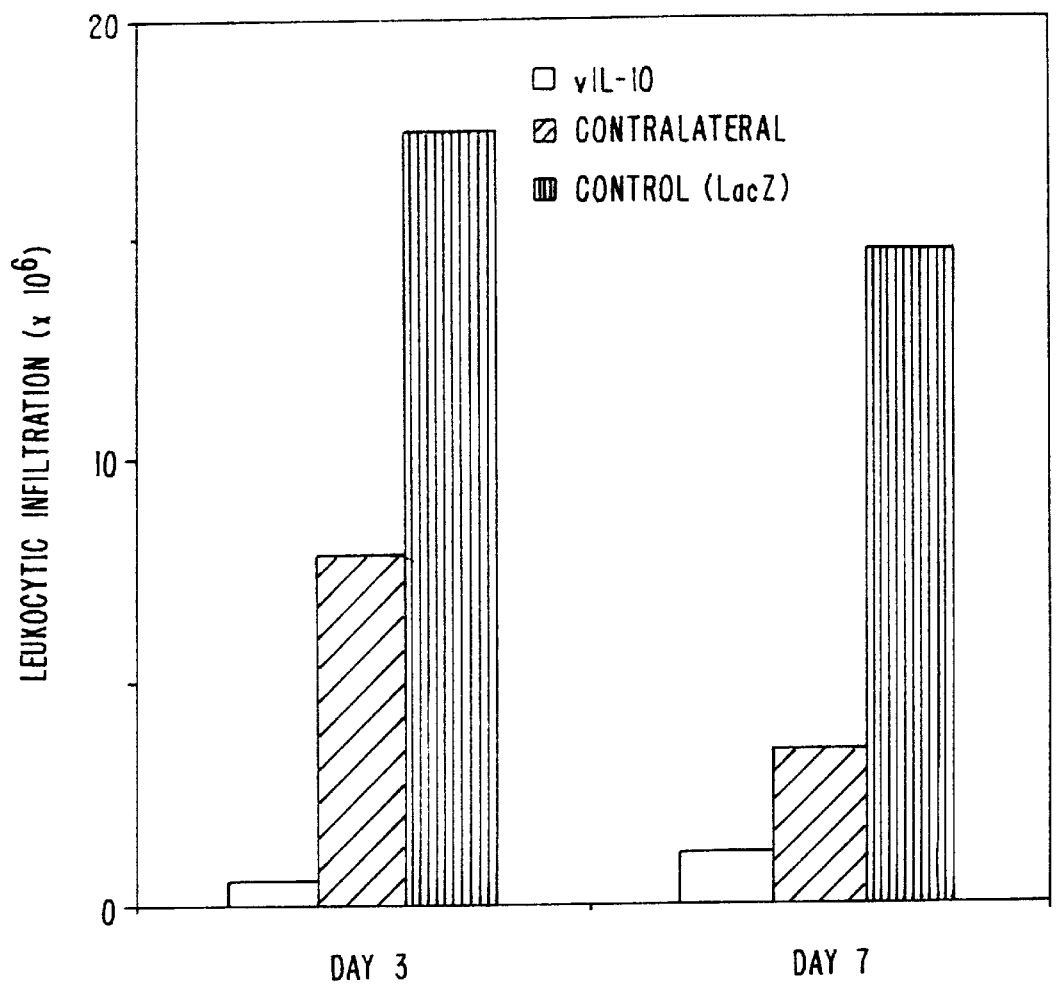

FIG. 33 shows a bar graph depicting the leukocytic infiltration in knees injected with vIL-10, the untreated knee and control knees 3 and 7 days after injection, determined according to the methods of Example XX.

Figure 34:
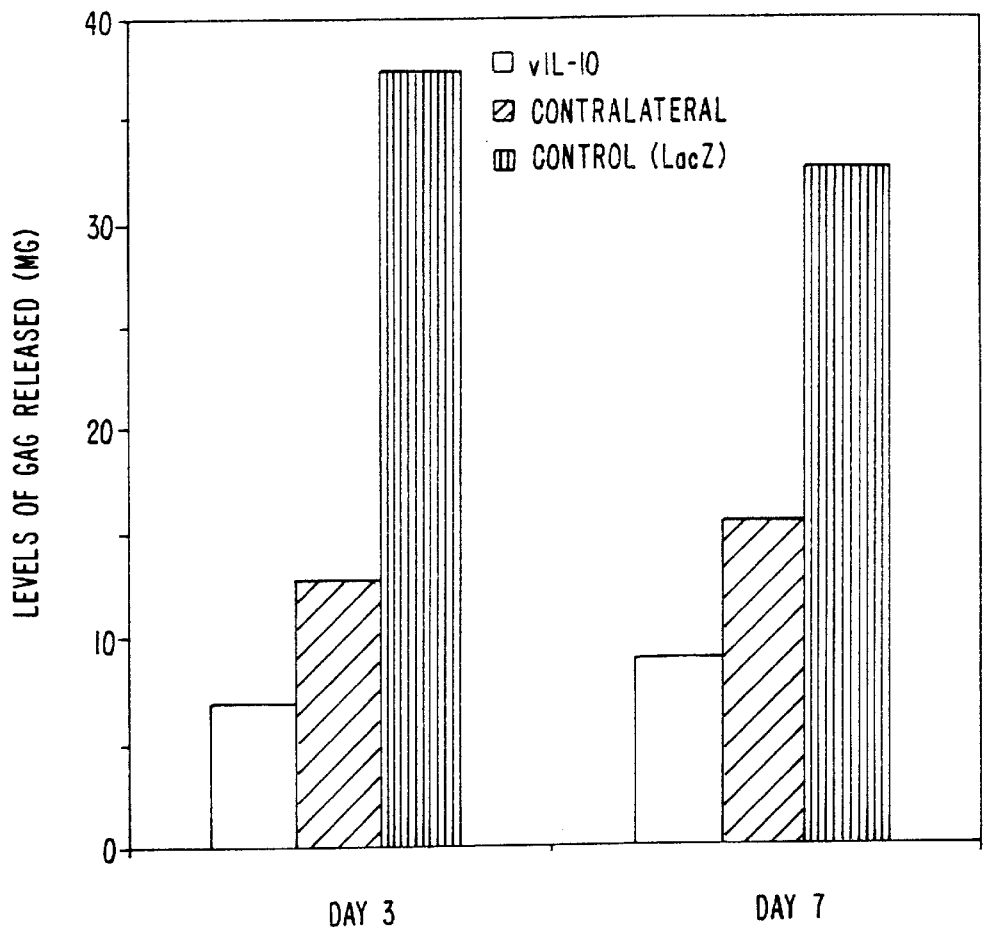

FIG. 34 is a bar graph showing the levels of GAG released in knees injected with vIL-10, the untreated knee, and control knees 3 and 7 days after injection, determined according to the methods of Example XX.

Figure 35:
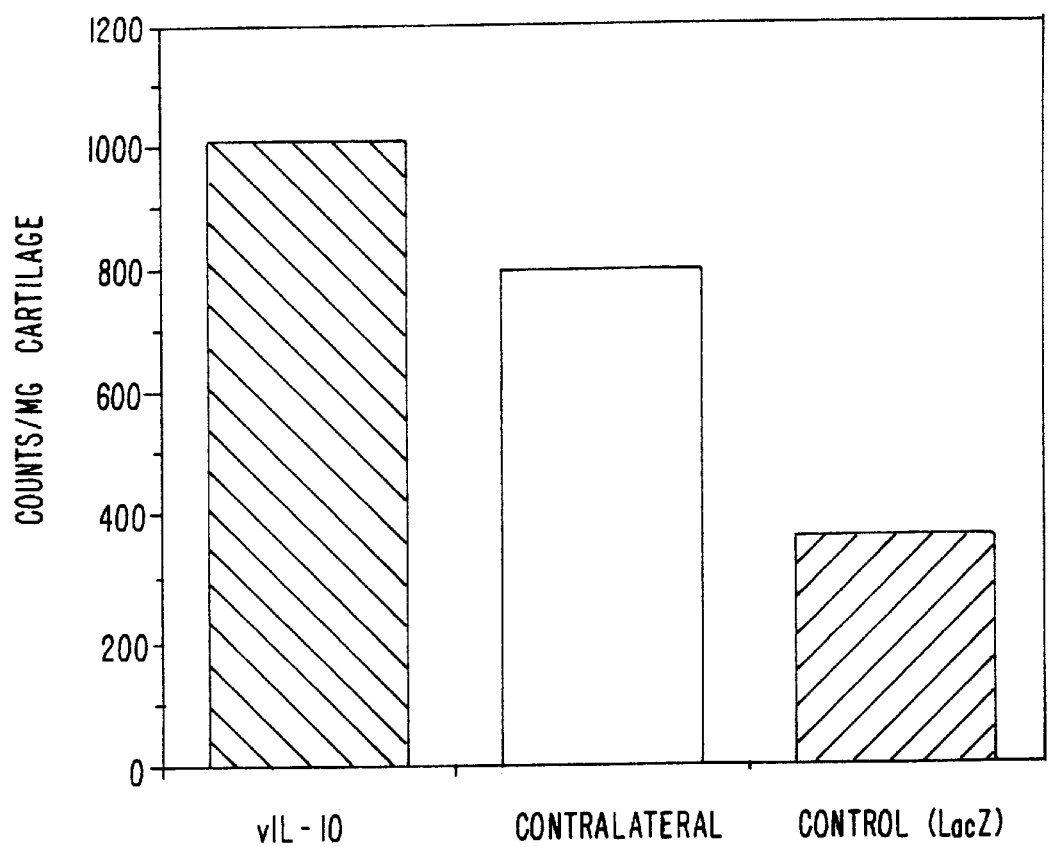

FIG. 35 shows the effects of vIL-10 on GAG synthesis rates in a.i.a. rabbit knees injected with vIL-10, the untreated knees, and control knees, determined according to the methods of Example XX.

Figure 36:
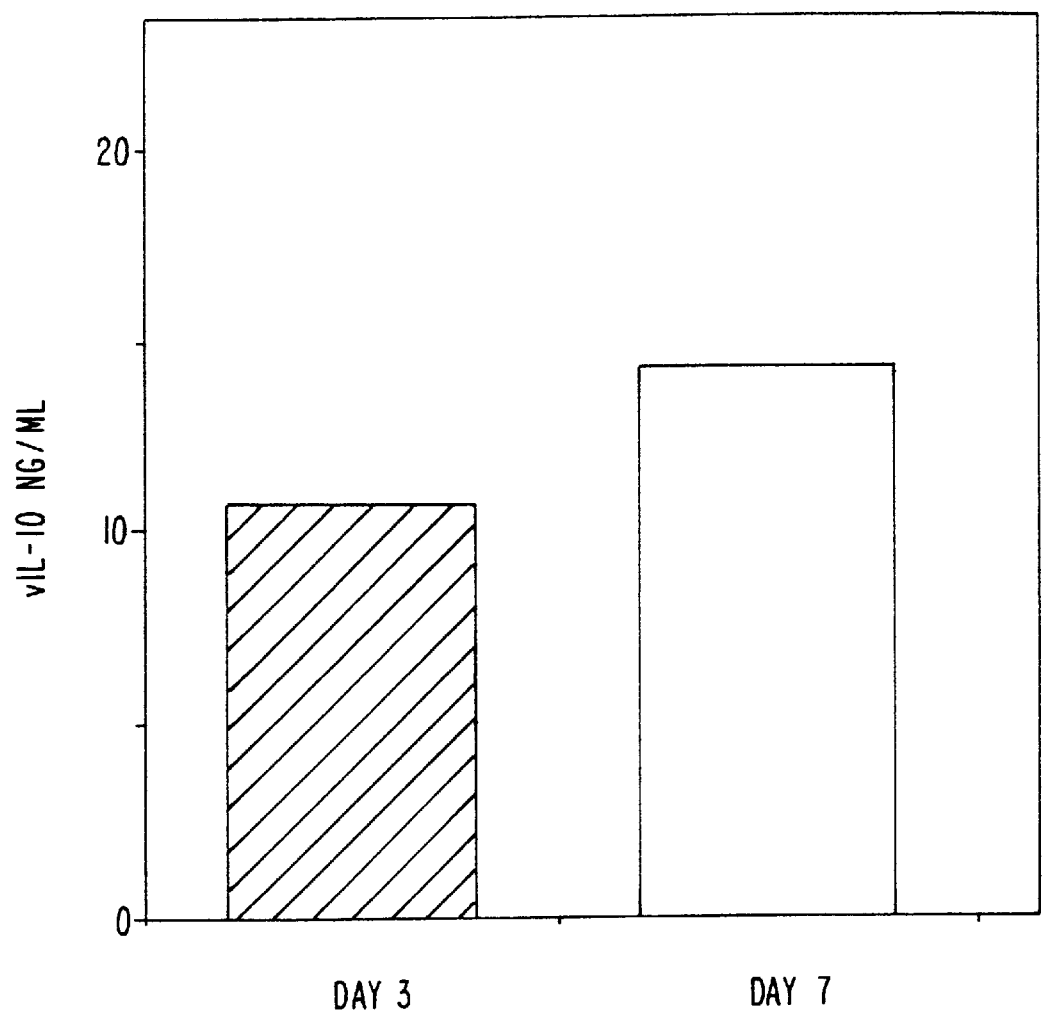

FIG. 36 shows the intraarticular expression of vIL-10 in rabbit knees 3 and 7 days after injection, determined according to the methods of Example XX.

FIG. 37(A–D) shows the histological analysis of rabbit knees injected with Ad.vIL-10, untreated knees, and control knees, determined according to the methods of Example XX.

Figure 38:
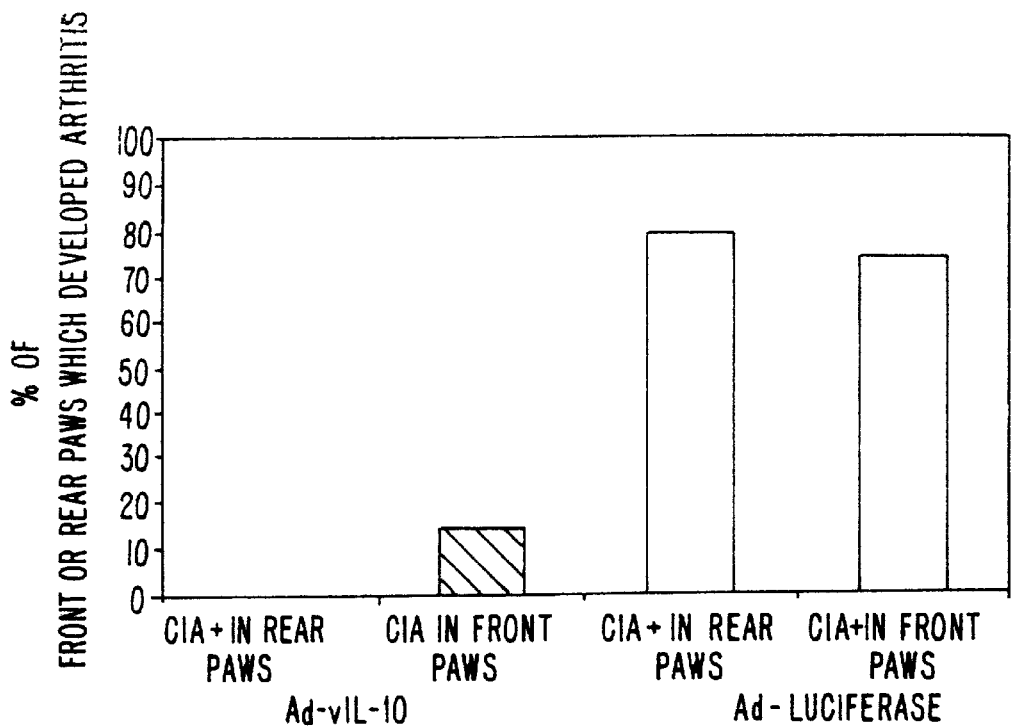

FIG. 38 shows the percentage of mice paws with arthritis 10 weeks after treatment, determined according to the methods of Example XXI.

Figure 39:
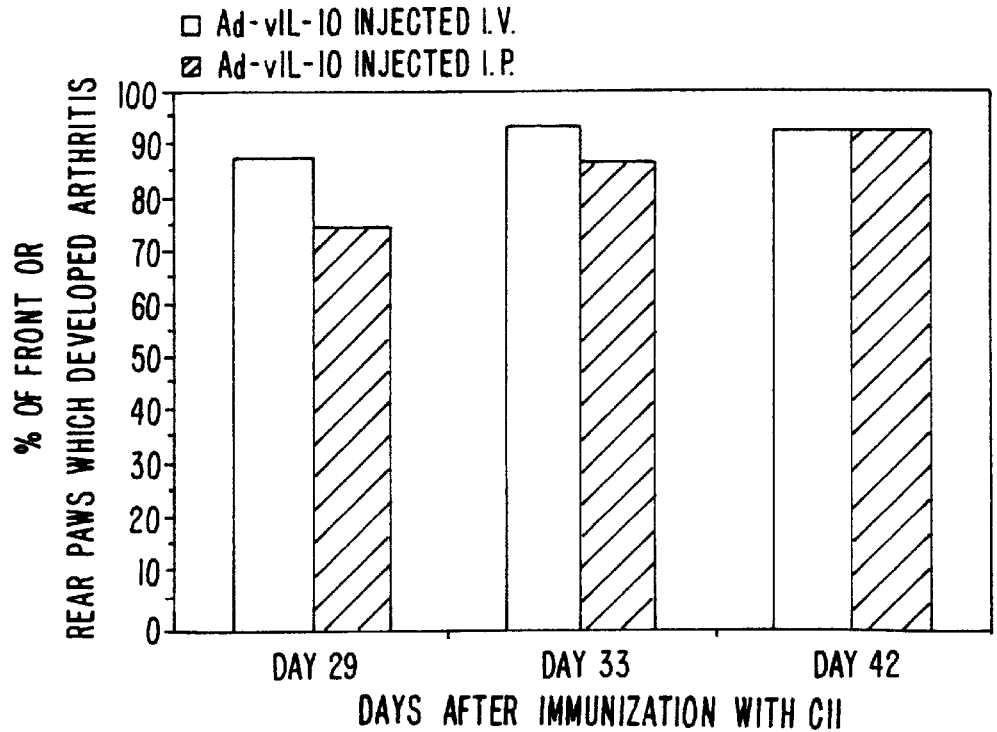

FIG. 39 shows the percentage of arthritic paws injected with Ad.vIL-10 systematically, determined according to the methods of Example XXI.

DETAILED DESCRIPTION OF THE INVENTION

As used herein, the term "pateint" includes members of the animal kingdom including but not limited to human beings.

As used herein, the term "mammalian host" includes mammalian members of the animal kingdom including but not limited to human beings.

As used herein, the term "target cells" refers to cells that are targeted for transfection with the gene or genes encoding the product(s) of interest. Target cells can be either cells that are removed form a host and cultured with the gene(s) in vitro and returned to a host in an ex vivo methodology, or cells that are in the host and are transduced or transfected in vivio. Generally a target cell when used in reference to ex vivo methods is any cell that, when injected into a joint of a patient, will survive and express the gene. When used in reference to in vivo methods, a target cell is any cell capable of being transduced or transfected with one or more genes of interest and which will subsequently express the gene. Target cells include both connective tissue cells and non-connective tissue cells, as those terms are defined below.

As used herein, the term "connective tissue" includes but is not limited to a ligament, a cartilage, a tendon, a synovium, skin, bone, meniscus and intervertebral disc tissue of a mammalian host.

As used herein, the term "non-connective tissue" includes but is not limited to hematopoietic progenitor cells, stromal cells, bone marrow cells, myoblasts, leukocytes, and lymphoid or myeloid cells of a mammalian host.

As used herein, the terms "gene", "DNA sequence" or "product" "of interest" refer to genes, DNA sequences or the products they encode that are introduced to the host according to any of the methods of the present invention. For methods used in the therapeutic or prophylactic treatment of a host, the products of interest would be those proteins or peptides, or fragments or derivatives thereof, that have therapeutic and/or prophylactic properties. For methods used in the animal model, the products of interest would be those proteins or peptides, or fragments or derivatives thereof, that have a pathologic effect on the host, contributing to one or more of the deleterious effects of connective tissue disorders.

As used herein, the term "therapeutic" refers to the ability of a gene, product, protein, peptide, method and the like to alleviate at least one symptom of a connective tissue disorder, or the benefit realized from such alleviation. The term "prophylactic" refers to the ability of a gene, product, protein, peptide, method and the like to prevent or at lest retard the onset of at lest one symptom of a connective tissue disorder, or the benefit realized from such action.

As used herein, the term "enhanced therapeutic benefit" refers to the therapeutic benefit realized when more than one gene of interest is introduced to a host at the same time; the therapeutic benefit is greater than the therapeutic benefit of each of the genes administered separately. The benefit can be either additive or synergistic.

As used herein, the term "DC-chol" means a cationic liposome containing cationic cholesterol derivatives. The "DC-chol" molecule includes a tertiary amino group, a medium length spacer arm (two atoms) and a carbamoyl linker bond as descried in *Biochem. Biophys. Res. Commun.*, 179:280–285 (1991), X. Gao and L. Huang.

As used herein, "SF-chol" is defined as a type of cationic liposome.

As used herein, the term "biologically active" used in relation to liposomers denotes the ability to introduce functional DNA and/or proteins into the target cell.

As sued herein, the term "biologically active" in reference to nucleic acid, protein, protein fragment or derivatives thereof is defined as an ability of the nucleic acid or amino acid sequence to mimic a known biological function elicited by the wild type form of the nucleic acid or protein.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic effect.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared with the wild type sequence, while the sequence still encodes a protein or peptide, or fragments thereof, that retain their wild type function despite these variations. Proteins, protein fragments, peptides, or derivatives also can experience deviations from the wild type from which still functioning in the same manner as the wild type form. Similarly, derivatives of the genes and products of interest used in the present invention will have the same biological effect on the host as the non-derivatized forms. Examples of such derivatives include but are not limited to dimerized or oligomerized forms of the genes or proteins, as wells as the genes or proteins modified by the addition of an immunoglobulin (Ig) group. Biologically active derivatives and fragments of the genes, DNA sequences, peptides and proteins of the present invention are therefore also within the scope of this invention.

One skilled in the art could test for the biological activity of derivatives and fragments of the genes listed above by various methods known to those skilled in the art. To determine if a fragment or derivative of IRAP is biologically active, a bioassay can be performed; if the compound blocks the ability of interleukin-1 to cause inflammation and cartilage breakdown, the derivative or fragment is a biologically active derivative or fragment of IRAP. Similarly, a bioassay can be performed to determine if a fragment or derivative of soluble interleukin-1 receptor protein is biologically active by determining whether the compound blocks the ability of interleukin-1 to cause inflammation and cartilage breakdown. To determine if a fragment or derivative of sTNF-αR protein is biologically active, a bioassay can be performed; if the compound prevents cell death in an L929 cell line in response to TNF-α, the fragment or derivative is biologically active. To determine if a fragment or derivative of a proteinase inhibitor is biologically active, a bioassay can be performed to determine whether the action of a proteinase is inhibited, such as by monitoring the rate of breakdown of a proteinaceous substrate. Inhibition of the proteinase would indicate biological activity. For example, the biological activity of a TIMP matrix metalloproteinase inhibitor can be determined by its ability to inhibit the activity of matrix metalloproteinases, as assayed by methods described by Watanabe et al., *Exp. Cell Res.*, 167:218–226 (1986). To determine if a fragment or derivative of a therapeutic cytokine is biologically active, a bioassay can be performed to determine if the cytokine has a therapeutic or prophylactic effect in inhibiting any of the symptoms associated with a connective tissue disorder. For example, the biological activity of IL-6 can b determined by its ability to promote growth of B29 cells, as described by Arden et al., *Eur. J. Immunol.*, 17:1411–1416 (1987). The biological activity of IL-10 or vIL-10 can be determined by the ability of derivatives or fragments of these compounds to inhibit the production of nitric oxide by activated macrophages. To determine if a fragment or derivative of a growth hormone or a growth factor is biologically active, bioassays can be performed as taught by Taskiran et al., *Biochem. Biophys. Res. Commun.*, 200:142–148 (1994); biologically active derivatives or fragments will demonstrate increased proteoglycan synthesis by cartilage. To determine if a fragment or derivative of an anti-adhesion molecule is biologically active, a bioassay can be performed to determine the ability of the derivative or fragment to inhibit adhesion. To determine if a fragment or derivative of a free radical antagonist is biologically active, a bioassay can be performed to determine the ability of the fragment or derivative to inhibit the production of free radicals. To determine if a derivative or fragment of CTLA4 is biologically active, a bioassay can be performed to determine if the compound has the ability to bind to cells expressing B7.1, in which case it would be active. To determine if a derivative or fragment of FasL is biologically active, a bioassay can be performed to determine if the compound has the ability to induce apoptosis of cells express Fas, which would indicate biological activity. To determine if a derivative or fragment of iNOS is biologically active, a bioassay can be performed to determine if the compound has the ability to synthesize NO, which would indicate biological activity. Any other manner for determining biological activity known to those skilled in the art can also be used.

Connective tissues are difficult to target therapeutically. Intravenous and oral routes of drug delivery that are known in the art provide poor access to these connective tissues and have the disadvantage of exposing the mammalian host body systemically to the therapeutic agent. More specifically, known intra-articular injection of joins provide direct access to a joint. However, most of the injected drugs have a short intraarticular half-life. The present invention solves these problems by introducing into the mammalian host, genes encoding for proteins that may be used to treat the mammalian host. In a preferred embodiment, this invention provides a method for introducing into the connective tissue of a mammalian host genes encoding for proteins with anti-arthritic properties.

The present invention provides a method for introducing at least one gene encoding a product into at least one target cell of a mammalian host for use in treating the mammalian host, which method comprises employing recombinant techniques to produce a vector containing one or more DNA sequences encoding one or more products of interest and infecting the target cell of the mammalian host with the vector. This method preferably includes introducing the gene encoding the product into at least one cell of the connective tissue of the mammalian host for a therapeutic use. Both in vivo and ex vivo methods can be used to introduce the gene of interest to the host.

Any type of connective tissue cell or non-connective tissue cells, as those terms are described herein, can be used. Preferably, if using connective tissue synovial cells are used; more preferably, for treating a human patient, the patient's own cells, such as autologous synovial cells, are used. When ligament cells are used, preferably the ligament is the medial collatoral ligament (MCL). Use of cells and/or tissue from the patellar tendon and hamstring are also within the scope of the invention. Preferably, if using non-connective tissue, stromal cells are used.

For the ex vivo methods, all of the non-connective tissue cells can be injected back into the host, such as in the bone marrow or bloodstream of the host following transduction. Both connective and non-connective tissue cells can be injected into the joint space or other areas of the host following transduction. For the in vivo methods, connective and non-connective tissue cells can be targeted at any location of the host, including but not limited to the bone marrow, bloodstream or joint space of the host.

Use of numerous genes, and biologically active derivatives and fragments thereof, are within the scope of the invention. Any gene capable of maintenance and expression, and encoding a product having a therapeutic and/or prophylactic effect in the treatment of joint pathologies can be used in the methods of treating a host. This includes, but is not limited to, DNA sequences encoding one or more of: interleukin-1 receptor antagonist protein (IRAP); a Lac Z marker gene capable of encoding a beta-galactosidase; a soluble interleukin-1 receptor (sIL-1R); a soluble TNF-α receptor (sTNF-αR); a proteinase inhibitor; a therapeutic cytokine; CTLA4; FasL; an anti-adhesion molecule; and a free radical antagonist. Any other gene having therapeutic properties and DNA capable of maintenance and expression can also be used. These genes can be either commercially obtained through any supplier, or can be made by one skilled in the art from cDNA libraries or through the reverse transcriptase polymerase chain reaction (RTPCR) method.

IRAP is a cytokine known to suppress the inflammatory responses caused by interleukin-1 in joint spaces. Introduction of IRAP to these spaces, therefore, causes a reduction in the inflammation associated with joint pathologies characterized as having IL-production. It is believed that the IRAP binds with the interleukin-1 receptors, thereby preventing binding of the IL-1 to the receptors, and inhibiting the inflammatory effects caused when IL-1 binds to the receptors, although the inventors do no wish to be bound by this mechanism.

Similarly, soluble interleukin-1 receptors (sIL-1R) bind to IL-1 without transmitting a cellular response, thereby preventing IL-1 from binding to the native, cell surface receptors. Any sIL-1 receptor can be used, including but not limited to, Type I and Type II receptors; sIL-1R Type II receptors are preferred because they do not bind to IRAP, while Type I receptors do. The sIL-1R of the present invention can be of any type, including Type I and Type II. The Type I sIL-1R is an 80 Kd glycoprotein that is present on T-lymphocytes, fibroblasts, and chondrocytes. The Type II sIL-1R is 67 Kd in size and is found predominantly on macrophages and pre-B-cells.

Soluble tumor necrosis factor-alpha receptor (sTNF-αR) binds TNF-α and prevents it from having a damaging effect on the connective tissue of a patient TNF-α is a cytokine which is known to contribute to the pathological effects of connective tissue disorders. The sTNF-αR of the present invention can be of any type, including Type I and Type II. The Type I sTNF-αR is an 55 Kd glycoprotein and the Type II sTNFα-R is 75 Kd in size. Both type of TNF-α receptors are widely distributed on various cell types. Both the sIL-1R and sTNF-αR have been shown to alleviate at least some of the symptoms associated with connective tissue disorders.

Various proteinase inhibitors are also within the scope of the present invention. Proteinase inhibitors are substances that prevent the enzymatic breakdown of proteins. Both proteinase inhibitors and metalloproteinase inhibitors are within the scope of the invention; preferred proteinase inhibitors are tissue inhibitor of metalloproteinase (TIMP), TIMP-1, TIMP-2, TIMP-3, TIMP-4, plasminogen activator inhibitors (PAIs) and serpins.

Cytokines are small proteins with the properties of locally acting hormones. They serve to communicate between cells in a paracrine manner, and may also act in an autocrine manner on the same cell that produces the cytokine(s). Certain cytokines are important in driving pathophysiological changes in arthritic joints, while other cytokines offer protective effects against these changes. Cytokines exhibiting a protective effect include various forms of interleukin (IL) including IL-4, IL-10 and IL-13; all of these cytokines act in an anti-inflammatory capacity, as an immunosuppressive agent, or exert an immunostimulatory effect, depending on the target cell. It is also believed that they protect against cartilage breakdown.

Viral IL-10 (vIL-10), another cytokine, is a variant of IL-10 produced by the Epstein Barr virus. This virally encoded gene product is also immuno-suppressive and anti-inflammatory.

Growth factors are types of cytokines that are anti-arthritic in that they maintain synthesis of the cartilaginous matrix. Growth factors include, but are not limited to, transforming growth fact (TGF), TGF-β1, TGF-β2 and TGF-β3, fibroblast growth factor (FGF), aFGF and bFGF, insulin-like growth factor (IGF), IGF-1 and IFG-2. While the effect of certain growth factors is not known, IGF's are known to maintain the synthesis of the cartilaginous matrix, and promote cartilage repair.

Growth hormone, and at least some of the bone morphogenetic proteins (BMP) are also cytokines. Growth hormone is believed to act by inducing local synthesis of IGF-1, although the inventors do not wish to be bound by this mechanism. There are at least nine BMP's; the BMP's are members of the TGF-β super family. BMP's induce the formation of both bone and cartilage. BMP-2 and BMP-7 (also known as osteogenic protein-1 (OP-1)) have shown to be particularly promising in the therapeutic treatment of connective tissue disorders, and are therefore the preferred BMP's for use in the methods of the present invention.

As used herein, the term "cytokine" refers to all of the therapeutic cytokines described above.

CTLA4 is a surface molecule found on T-cells, which binds to a counter-ligand known as B7 on the surface of antigen-presenting cells (APC's). In its soluble form, CTLA4 binds to B7 and thereby prevents B7 from interacting with a co-stimulatory molecule known as CD28 on the surface of the T-cell. When B7 CD28 interactions are blocked in this way, T-cell activation and hence the immune response is prevented. There is evidence that this process can induce immune tolerance. CTLA4 is typically used in soluble form.

Fas ligand (FasL) is a cell surface protein that binds to another protein, called Fas, found on the surface of other cells, including lymphocytes. When FasL binds to Fas, the cell expressing Fas undergoes apoptosis. Soluble FasL may also induce apoptosis and may be used to kill lymphocytes, as well as other Fas⁺ cells in synovium.

Various anti-adhesion molecules are also within the scope of the present invention. These molecules function by inhibiting cell-cell and cell-matrix interactions and have anti-inflammatory properties. Examples of such proteins, including their fragments and derivatives, are soluble ICAM-1 and soluble CD44.

The use of free radical antagonists is also within the scope of the present invention. These antagonists function to prevent the deleterious effects of free radical formation within the afflicted joint. Examples include but are not limited to the superoxide dismutase and proteins or protein fragments which inhibit NO and NO synthase.

Preferred genes for use in the present invention for eliciting a therapeutic and/or prophylactic benefit in a host include IRAP, sIL-1RI, sIL-1RII, sTNF-αRI, sTNF-αRII, TIMP-1, TMP-2, TIMP-3, TIMP-4, PAIs, serpins, IL-4, IL-10, IL-13, IGF-1, IGF-2, vIL-10, CTLA4, BMP-1, BMP-2, BMP-3, BMP-4, BMP-5, BMP-6, BMP-7, FasL and their derivative forms. Use of other therapeutic genes is also within the scope of the present invention.

The scope of the present invention includes the use of one or more of the above-recited therapeutic genes in the therapeutic or prophylactic treatment of a connective tissue disorder. Genes encoding for more than one protein can be introduced through the same vector, as described below, or can be introduced through the use of different vectors, with each vector containing a different gene of interest. An unexpected discovery of the present invention is that the use of two or more genes together produces an enhanced therapeutic benefit. Particularly preferred for use together are genes encoding for sTNF-αR and sIL-1R. Other gene combinations are within the scope of the present invention as well. When administering two or more different genes through two or more different vectors or other means of delivery, each of the delivery means can be introduced simultaneously or can be introduced in succession. If in succession, introduction of the second, third, or greater genes is preferably done immediately following introduction of the first gene, to ensure that the highest levels of expression of each gene are achieved in the host at the same time.

Numerous methods known to those skilled in the art can be used to introduce the gene encoding the product of interest into the mammalian host. For example, viral and non-viral vectors can be prepared by recombinant methods to include the gene coding for the product of interest.

In one embodiment of this invention, the viral vector is a retroviral vector. Retroviral vectors include, but are not limited to, MFG and pLJ. An MFG vector is a simplified Moloney murine leukemia virus vector (MoMLV) in which the DNA sequences encoding the pol and env proteins have been deleted so as to render it replication defective. An MFG vector can be prepared that contains one DNA sequence of interest. Two (DFG), three (TFG) or even more DNA sequences of interest can also be included in the MoMLV. Thus, DFG and TFG are forms of MFG having multiple genes. For ease of reference, the term MFG, as used herein includes any singular or multiple gene forms of the vector. A pLJ retroviral vector is also a form of the MoMLV and is more fully described by Korman et al., *Proc. Nat'l Acad. Sci.*, 84:2150–2154 (1987), which description is hereby incorporated by reference.

Preferred embodiments of this invention includes employing a gene capable of encoding a human IAP, sIL-1R, sTNF-αR, and vIL-10, or biologically active derivatives or fragments thereof, and employing MFG as the retroviral vector.

Other viral vectors containing the gene encoding for the product can also be used, such as an adeno-associated virus, an adenovirus, and a herpes virus, such as herpes simplex type-1 or herpes simplex type-2. Other DNA vectors, such as plasmid or viral vectors can also be used.

Non-viral means for introducing the gene encoding for the product into the target cell can also be used. This method includes employing non-viral means selected from the group consisting of at least one liposome, $Ca_3(PO_4)_2$, electroporation, and DEAE-dextran. Direct injection of naked DNA can also be used. The liposome can be a material selected from the group consisting of DC-chol, SF-chol and numerous others known to those skilled in the art. It will be understood that such non-viral means for introducing the gene encoding for the product into the target cell provides a non-infectious delivery system. An advantage of the use of a non-infectious delivery system is the elimination of insertional mutagenesis and virally induced disease. In addition, the viral vectors employing a liposome are not limited by cell division as is required for the retroviruses to effect infection and integration of target cells.

Yet another method for introducing at least one gene encoding a product into at least one cell of a mammalian host for use in treating the mammalian host includes employing the biologic means of utilizing a virus to deliver the DNA vector molecule to the target cell or tissue. Preferably, the virus is a pseudo-type retrovirus, the genome having been altered such that the pseudo-type retrovirus is capable only of deliver and stable maintenance within the target cell, but not retaining an ability to replicate within the target cell or tissue.

The altered viral genome is further manipulated by recombinant DNA techniques such that the viral genome acts as a DNA vector molecule which contains the heterologous gene of interest to be expressed within the target cell or tissue.

As described above, the gene or interest can be introduced to the mammalian host through a variety of viral and non-viral means. These means can be employed both in vitro and in vivo.

For example, this invention provides a method for introducing at least one gene encoding a product into at least one target cell of a mammalian host for use in treating the mammalian host by effecting in vivo the infection of the cell by introducing the DNA sequence coding for the product directly into the mammalian host. This in vivo method involves introducing a DNA sequence directly to the target cell(s). The DNA sequence can be contained within any of the viral or non-viral vectors disclosed herein or can be a naked DNA sequence. Preferably, this method includes effecting the direct introduction into the mammalian host by intraarticular injection, although any method of introduction known to those skilled in the art can be used. Upon introduction of the DNA sequence to the connective or non-connective tissue cells, the cells are transduced with the DNA sequence, and the product which the sequence encodes will be expressed within the cell.

A method for introducing at lest one gene encoding a product into at least one target cell of a mammalian host for use in treating the mammalian host is provided that includes introducing the gene into the target cell in vitro and transplanting the transduced cell having the gene into the mammalian host. After introducing the gene encoding for the product into the target cell and before the transplanting the target cell into the mammalian host, the target cells having the gene can be stored. This method includes storing target cells frozen in 10 percent DMSO in liquid nitrogen.

In a preferred embodiment of the invention, target cells are transfected in vivo following direct intraarticular injection of a DNA molecule containing the gene of interest into the joint. Transfection of the recipient target cells bypasses the requirement of removal, culturing, in vitro transfection, selection and transplanting the DNA vector containing—target cells to promote stable expression of the heterologous gene of interest. Methods of injecting the DNA molecule into the joint include, but are not limited to, association of the DNA molecule with cationic liposomes or the direct injection of the DNA molecule itself into the joint. Expression of the heterologous gene of interest subsequent to in vivo transfection of the host tissue is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the host tissue.

As will be appreciated, the in vivo methodology of the present invention can be used with any of the above-listed therapeutic genes. One or more therapeutic genes can be used. An unexpected finding of the present invention is that the concurrent injection of more than one gene results in an enhanced therapeutic benefit. Thus, the therapeutic benefit observed when using more than one gene together is greater than if the genes were introduced separately. A particularly preferred embodiment involves the injection of DNA encoding sIL-1R and sTNF-αR either concurrently or in succession. Genes encoding these two products, or any other products can be introduced to a target cell either by the same vector or separate vectors, or by other delivery means as described above. Any of the viral or non-viral vector or biological means described throughout the specification can be used for the introduction of one or more genes to the host for the in vivo therapeutic benefit to be realized. When administering two or more different genes through two or more different vectors or other means of delivery, each of the delivery means can be introduced simultaneously or can be introduced in succession. If in succession, introduction of the second, third, or greater genes is preferably done immediately following introduction of the first gene, to ensure that the highest levels of expression of each gene are achieved in the host at the same time.

Also, any of the connective tissue cells or non-connective tissue cells, as those terms are described herein, can be targeted by in vivo injection of the gene or genes of interest.

As described herein, a DNA sequence that encodes a protein of interest is introduced to a joint of a mammalian host through a variety of ways. Subsequent expression of the protein is observed. An unexpected finding of the present invention is that the introduction of DNA into one joint leads to expression of the protein in that joint, and also in other joints of the host as well. Treatment of, for example, one knee joint leads to a therapeutic effect in other knee joints as well. Thus, the protective effects of local gene therapy as taught by the present invention are not limited to the target joint, but can affect distal joints as well.

Accordingly, another embodiment of the present invention provides a method for treating a connective tissue disorder comprising generating a recombinant vector that comprises at least one DNA sequence encoding one or more genes of interest and infecting a population of target cells, in vivo, in a first joint of a host with the vector such that subsequent expression of the gene(s) in the host reduces at least one deleterious joint pathology or indicia of inflammation normally associated with a connective tissue disorder both in the first joint and in one or more distal or untreated joints in the host. Any of the therapeutic genes and vectors as described above can be used. Alternatively, introduction of the gene(s) of interest can be accomplished by any of the non-vector means disclosed herein.

The present invention provides for a distal or systemic-type method of treatment following local injection. As discussed particularly in Example XVII, direct intraarticular delivery of adenoviral vectors encoding IL-1 and TNFα inhibitors (sIL-1R and STNF-αR) have an anti-inflammatory effect that is not limited to the site of virus injection. One possible explanation for this observation is that sufficient levels of inhibitor protein were present in the contralateral joint to confer a protective effect. However, significant levels (>1 ng/ml) of TNFα inhibitor molecules were not detected in sera or lavage fluids from untreated joints. To test if lower levels of the soluble receptors could indeed produce local anti-inflammatory effects, $3.5 \times 10^6$ pfu of each adenoviral inhibitor were injected into knees of rabbits 24 hours post-induction of a.i.a. This lower does of adenovirus resulted in a low but detectable level of sTNFα-receptor expression ranging from ~0.5 to 1.5 ng/ml of lavage fluid. However, there was no apparent local anti-inflammatory effect.

A second possible mechanism for the observed therapeutic benefit in untreated joints is that adenoviral particles or virally transduced cells were migrating from the joint of injection to the opposite knee or other organs, and thereby causing a systemic anti-inflammatory effect. To test this possibility, an adenoviral vector encoding the firefly luciferase reporter gene (Ad.luciferase) was utilized. A.i.a. was induced in both knees of two rabbits. Twenty-four hours post induction, $1.5 \times 10^9$ pfu of the Ad.luciferase virus was injected into one knee of each rabbit, while the untreated knee received $7 \times 10^7$ pfu of Ad.lacZ. At 7 days post injection, the rabbits were bled and sacrificed, the joints lavaged, and the joint capsules of both knees harvested along with regional lymphoid tissue, heart, liver, lung, spleen and kidney. Recovered tissues and leukocytes were then analyzed for the presence of intracellular luciferase activity. A low level of luciferase activity was observable in lymphoid tissue obtained near the site of injection and in synovial tissue of the untreated knee joint relative to knees receiving the Ad.luciferase vector. Analysis of similar numbers of leukocytes obtained from both knee joints and peripheral blood showed luciferase activity in leukocytes obtained from the injected knee and a lower level in the untreated knee. No appreciable activity was detected in circulating leukocytes. These results demonstrate that a population of transduced leukocytes can migrate to the opposing inflamed knee joint suggesting a possible mechanism for the observed untreated effect. The inventors do not wish to be bound by any of these mechanisms, however.

The in vivo methods of the invention can be used in the therapeutic treatment of patients suffering from one or more of the symptoms associated with joint pathologies, and in the repair and/or regeneration of connective tissue effected by such pathologies. The methods can also be used prophylactically, the prevent or retard onset of the symptoms of connective tissue disorder in patients susceptible to such disorders.

The methods of the present invention provide a means for introduction of one or more products of interest to the connective tissue of a host. These products are generally known in the art as being effective against the symptoms of connective tissue disorders. The amount of each product, in the form of the DNA sequence encoding the product, to introduce will vary from patient to patient depending on such factors as the size of the patient, the joint affected, the severity of the connective tissue disorder, the gene being used and whether the method is being used therapeutically or prophylactically. Therapeutic responses are typically seen based upon delivery of a vector or other delivery vehicle sufficient to give gene expression in the high pico- to low nanogram range.

One skilled in the art can determine the amount of vector or other delivery means to administer to a patient to achieve these levels of expression based upon the factors listed above. Introduction of vectors, such as a retroviral vector, in normal titer (about $10^5$ cfu/ml) is typically sufficient, but high titer concentrations (equal to or greater than about $10^7$ cfu/ml) are preferred.

Another embodiment of the present invention provides a method to produce an animal model for the study of connective tissue pathology. As will be understood by those skilled in the art, over-expression of interleukin-1 in the joint of a mammalian host is generally responsible for the induction of an arthritic condition. This invention provides a method for producing an animal model using the above described gene transfer technology of this invention. Preferably, the method of this invention provides a method for producing an animal model using the various gene transfer technologies of this invention s described above to effect an animal model for arthritis. For example, constitutive expression of interleukin-1 in the joint of a rabbit following the method of gene transfer provided for by this invention leas to the onset of an arthritic condition. It will be appreciated by those skilled in the art that this rabbit model is suitable for use for the testing of therapeutic agents. This method includes introducing at lest one gene encoding a product into at least one cell of a connective tissue of a mammalian host comprising (a) employing recombinant techniques to produce a recombinant vector that contains the gene encoding for the product and (b) infecting the target cell of the mammalian host using the recombinant vector containing the gene coding for the product for effecting the animal model.

Any gene known to contribute to one or more of the symptoms of connective tissue disorders can be used in the animal model. As with the therapeutic treatment methodology, more than one gene can be introduced. Genes suitable for use in the animal model methods of the present invention, therefore, include any genes which cause such a symptom, including but not limited to various forms of interleukin such as IL-1α, IL-1β, IL-2, IL-7 IL-8, IL-12, IL-15 and IL-17, TNF-α, TNF-β, iNOS and proteinases including but not limited to aggrecanase, or a matrix metalloproteinase selected from the group consisting of at least one collagenase, gelatinase and stromelysin. Inducible nitric oxide synthase (iNOS or NOSII) is an enzyme found in arthritic joints, which catalyzes the formation of the radical nitric oxide (NO).

Any biologically active derivatives or fragments of these genes can also be used. One skilled in the art can test the biological activity of such derivatives or fragments by evaluating their ability to contribute to one or more of the deleterious symptoms associated with connective tissue disorders.

Any of the viral or non-viral means described in conjunction with the therapeutic method can be used to effect delivery of the DNA sequence or sequences of interest in the animal model. Also, any of the connective or non-connective tissue cells can be targeted in the animal model, as described above for the therapeutic methods. It will be appreciated by those skilled in the art that introduction of any of the deleterious genes listed above will result in conditions mimicking those seen in an animal suffering from a connective tissue disorder. The afflicted animal can then be used to study potential methods for therapeutically treating such connective tissue disorders experienced by humans. Thus, the animal model of the present invention provides a correlatable means of studying connective tissue disorders.

EXAMPLES

The following examples are intended to illustrate the present invention and should not be construed as limiting the invention in any way.

Example I

Packaging of AAV

The only cis-acting sequences required for replication and packaging of recombinant adeno-associated virus (AAV) vector are the AAV terminal repeats. Up to 4 kb of DNA can be inserted between the terminal repeats without effecting viral replication or packaging. The virus rep proteins and viral capsid proteins are required in trans for virus replication as is an adeno-associated virus helper. To package a recombinant AAV vector, the plasmid containing the terminal repeats and the therapeutic gene is co-transfected into cells with a plasmid that expresses the rep and capsid proteins. The transfected cells are then infected with adeno-associated virus and virus isolated from the cells about 48–72 hours post-transfection. The supernatants are heated to about 56° Centigrade to inactivate the adeno-associated virus, leaving an active virus stock of recombinant AAV.

Example II

Electroporation

The connective tissue cells to be electroporated are placed into Hepes buffer saline (HBS) at a concentration of about $10^7$ cells per ml. The DNA to be electroporated is added at a concentration of about 5–20 ug/ml of HBS. The mixture is placed into a cuvette and inserted into the cuvette holder that accompanies the Bio-RAD electroporation device (1414 Harbour Way South, Richmond, Calif. 94804). A range between about 250 and 300 volts at a capacitance of about 960 ufarads is required for introduction of DNA into most eukaryotic cell types. Once the DNA and the cells are inserted into the Bio-RAD holder, a button is pushed and the set voltage is delivered to the cell-DNA solution. The cells are removed from the cuvette and replated on plastic dishes.

Example III

Figure 1:
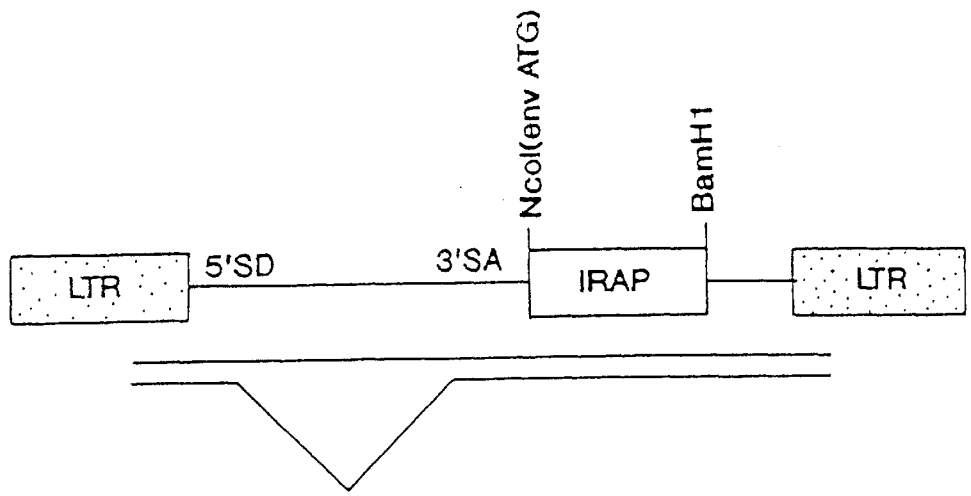
FIG. 1 shows the structure of the cDNA encoding the human interleukin-1 receptor antagonist protein (IRAP) gene inserted into the NcoI and BamHI cloning sites of the retroviral vector MFG.

The cDNA encoding the human interleukin-1 receptor antagonist (IRAP) was inserted into the NcoI and BamHI cloning sites of the retroviral vector MFG as shown in FIG. 1. Specifically, a Pst1 to BamHI fragment from the IRAP cDNA was linked to a synthetic oligonucleotide adapter from the NcoI site (representing the start site of translation for IRAP) to the Pst1 site (approximately 12 base pairs downstream from the NcoI site) to the MFG backbone digested at NcoI and BamHI in a three part ligation reaction. This three part ligation involving a synthetic oligo and two DNA fragments is well known by those skilled in the art of cloning. LTR means long terminal repeats, 5'SD means 5' splice donor, 3'SA means 3' splice acceptor. The straight arrow and the crooked arrow in FIG. 1 represent unspliced and spliced messenger RNAs respectively. IRAP is encoded by the spliced message.

Figure 2:
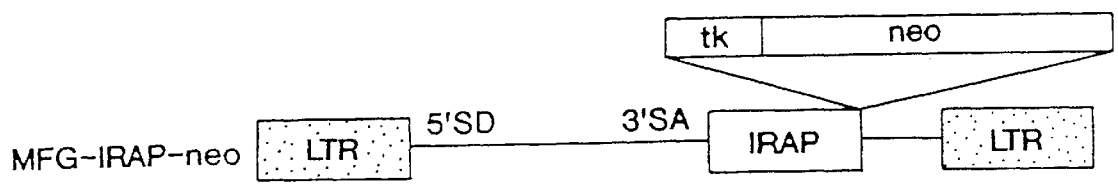
FIG. 2 shows the structure of the cDNA encoding the human interleukin-1 receptor antagonist protein (IRAP) gene with a selectable neo marker inserted into the retroviral vector MFG.
Figure 3:
FIG. 3 shows a micrography of synovium recovered from the knee of a rabbit approximately one month after introaarticular injection of LacZ$^+$, neo$^+$ synoviocytes employing the methods of this invention.

FIG. 2 shows the cDNA encoding the human interleukin-1 receptor antagonist protein (IRAP) with a selectable neo gene marker. FIG. 3 shows a low power micrograph of synovium recovered from the knee of a rabbit one month after intra-articular injection of LacZ$^+$, neo$^+$ synoviocytes. Tissue was stained histochemically for the presence of beta-galactosidase. This micrograph counterstained with eosin revealed an area of intensely stained, transplanted cells demonstrating that these cells have colonized the synovial lining of the recipient joint.

Example IV

Animal Models

The methods of this invention of transferring genes to the synovia of mammalian joints permit the production an analysis of joint pathologies that were not previously possible. This is because the only other way of delivering potentially arthritogenic compounds to the joint is by intra-articular injection. Not only are such compounds quickly cleared from joints, but the effects of bolus injections of these compounds do not accurately mimic physiological conditions where they are constantly produced over a long period of time. In contrast, the gene transfer technologies of this invention permit selected proteins of known or suspected involvement in the arthritic process to be expressed intraarticularly over an extended period of time, such as for example, at least a three month period. The animal models of this invention therefore permits the importance of each gene product to the arthritic process to be evaluated individually. Candidate genes include, but are not restricted to, those coding for cytokines such as interleukin-1(IL-1) alpha, IL-1 beta, and TNF-alpha, and matrix metalloproteinases such as collagenases, gelatinases and stromelysins.

Additionally, the gene transfer techniques of this invention are suitable for use in the screening of potentially therapeutic proteins. In this use, the animal models of the invention are initiated in joints whose synovia express gene coding for potential anti-arthritic proteins. Candidate proteins include, but are not restricted to, inhibitors of proteinases such as, for example, the tissue inhibitor of metalloproteinases, and cytokines such as, for example, transforming growth factor-beta.

Example V

Method for Using Synoviocytes As A Delivery System For Gene Therapy

Rabbits are killed by intravenous injection of 4 ml nembutal, and their knees quickly shaved. Synovia are surgically removed from each knee under aseptic conditions, and the cells removed from their surrounding matrix by sequential digestion with trypsin and collagenase (0.2% w/v in Gey's Balanced Salt Solution) for about 30 minutes and about 2 hours, respectively. The cells recovered in this way are seeded into 25 cm$^2$ culture flasks with about 4 ml of Ham's $F_{12}$ nutrient medium supplemented with 10% fetal bovine serum, 100 U/ml penicillin and 100 $\mu$g/ml streptomycin, and incubated at about 37° in an atmosphere of 95% air, 5% $CO_2$. Following about 3–4 days incubation, the cells attain confluence. At this stage, the culture medium is removed and the cell sheet washed twice with approximately 5 mls of Gey's Balanced Salt Solution to remove non-adherent cells such as lymphocytes. The adherent cells are then treated with trypsin (0.25% w/v in balanced salt solution). This treatment detaches the fibroblastic, Type B synoviocytes, but leaves macrophages, polymorphonuclear leukocytes and the Type A synoviocytes attached to the culture vessel. The detached cells are recovered, re-seeded into 25 cm$^2$ culture vessels at a 1:2 split ratio, medium is added and the culture returned to the incubator. At confluence this procedure is repeated.

After the third such passage, the cells are uniformly fibroblastic and comprise a homogeneous population of Type B synoviocytes. At this stage, cells are infected with the retroviral vector.

Following infection, cells are transferred to fresh nutrient medium supplemented with about 1 mg/ml G418 (GIBCO/BRL, P.O. Box 68, Grand Island, N.Y. 14072-0068) and returned to the incubator. Medium is changed every three days as neo$^-$ cells die and the neo$^+$ cells proliferate and attain confluency. When confluent, the cells are trypsinized and subcultured as described above. One flask is set aside for staining with X-gal to confirm that the neo$^+$ cells are also Lac Z$^+$. When the subcultures are confluent, the medium is recovered and tested for the presence of IRAP, soluble IL-1R or other appropriate gene products as hereinbefore described. Producing synoviocyte cultures are then ready for transplantation.

The cells are recovered by centrifuging, washed several times by resuspension in Gey's Balanced Salt Solution and finally resuspended at a concentration of about $10^6$–$10^7$ cells/ml in Gey's solution. Approximately 1 ml of this suspension is then introduced into the knee joint of a recipient rabbit by intra-articular injection. For this purpose a 1 ml syringe with a 25-gauge hypodermic needle is used. Injection is carried out through the patellar tendon. Experiments in which radiopaque dye was injected have confirmed that this method successfully introduces material into all parts of the joint.

Variations on the disclosed harvesting, culture and transplantation conditions in regard to the numerous examples presented within this specification will be evident upon inspection of this specification. Several tangential points may be useful to one practicing the ex vivo based gene therapy portion of the disclosed invention:

(1) If the yield of synoviocytes from the harvested synovial tissue is poor, the surgical technique may be at fault. The synovium has a strong tendency to retract when cut. Therefore, the inner capsule is grasped firmly, and with it the synovium, while excising this tissue. A small (about 2 mm) transverse incision can be made inferiorly, followed by sliding one point of the forceps into the joint space so that the synovium and inner capsule are sandwiched between the points of the forceps. The tissue is then excised without releasing the tissue thus preventing retraction of the synovium.

(2) A two compartment digestion chamber may be used to initially separate the cells from extracellular debris. In lieu of this choice, synovial tissue may be digested in a single chamber vessel and filtered through a nylon monofilament mesh of 45 $\mu$m pore size.

(3) When resuspending cells, the smallest amount of medium possible can be used to prevent formation of clumps of cells, which are difficult to separate once formed. EDTA in millimolar amounts can also be used to prevent clumps.

(4) During trypsinization, synoviocytes can lose the fusiform morphology that they possess in adherence, and assume a rounded shape. The cells initially will detach in clumps of rounded cells; one may allow the majority of cells to separate from each other before stopping trypsinization.

(5) Synoviocytes may be transduced with multiple transgenes by use of retroviral vectors containing multiple transgenes or by sequential transduction by multiple retroviral vectors. In sequential transduction, the second transduction should be made following selection, when applicable, and passage after the first transduction.

(6) As the synovium is a well-innervated structure, intraarticular injection can be painful, especially if done rapidly. Intra-articular injection of a 1 ml volume should take 10 to 15 seconds.

(7) In the animal model, the depth of the needle stick should not exceed 1 cm during intraarticular injection, and depression of the syringe plunger should meet with little to no resistance. Resistance to advancement of the syringe plunger indicates that the tip of the needle is not in the joint space.

(8) In the animal model, to retrieve a useful volume of the injected Gey's solution during joint lavage, the needle should not be inserted too deeply, otherwise it may penetrate the posterior capsule and may lacerate the popliteal artery. Firm massage of the suprapatellar, infrapatellar, and lateral aspects of the knee during aspiration helps to increase the amount of fluid recovered; in general, it should be possible to recover $\geq 0.5$ ml of fluid. When knees are badly inflamed, lavage is often difficult because of the presence of large numbers of leukocytes, fibrin, and other debris in the joint.

The animal can be anesthetized or sacrificed and the Gey's solution recorded surgically.

Example VI

The method of Example V for producing generally uniformly fibroblastic cells of a homogeneous population of Type B synoviocytes was followed to effect growing cultures of lapine synovial fibroblasts. These growing cultures of lapine synovial fibroblasts were subsequently infected with an amphotropic retroviral vector carrying marker genes coding for beta-galactosidase (Lac Z) and resistance to the neomycin analogue (G418 (neo$^+$). Following infection and growth in selective medium containing about 1 mg/ml G418, all cells stained positively in a histochemical stain for beta-galactosidase.

Neo selected cells carrying the Lac Z marker gene were transplanted back into the knees of recipient rabbits to examine the persistence and expression of these genes in vivo. Two weeks following transplantation, islands of Lac Z$^+$ cells within the synovium of recipient knees were observed. This confirmed the ability of the method of this invention to introduce marker genes into rabbit synovia and to express them in situ.

Example VII

Neo-selected, Lac Z$^+$ synoviocytes were recovered from cell culture, suspended in Gey's Balanced Salt Solution and injected intra-articularly into the knee joints of recipient rabbits (about $10^5$–$10^7$ cells per knee). Untreated control knees received only a carrier solution. At intervals up to 3 months following transplant, the rabbits were killed and their synovia and surrounding capsule recovered. Each sample may be analyzed in three ways. A third of the synovium was stained histochemically en masse for the presence of beta-galactosidase. A second portion may b used for immunocytochemistry using antibodies specific for bacterial beta-galactosidase. The final portion may be digested with trypsin and collagenase, and the cells thus recovered cultured in the presence of G418.

Staining of the bulk synovial tissue revealed extensive areas of Lac Z$^+$ cells, visible to the naked eye. Control synovia remained colorless. Histochemical examination of synovia revealed the presence of islands of cells staining intensely positive for beta-galactosidase. These cells were present on the superficial layer of the synovial lining, and were absent form control synovia. From such tissue it was possible to grow Lac Z$^+$, neo$^+$ cells. Cells recovered from control tissue were Lac Z$^-$ and died when G418 was added to the culture. This indicates that the transplanted, transduced synovial fibroblasts have successfully recolonized the synovia of recipient joints, and continue to express the two marker genes, Lac Z and neo. Maintaining intra-articular Lac Z and neo expression in transplanted synoviocytes has been effected for about 6 weeks using primary cells and about 2 weeks using the HIG-82 cell line.

Example VIII

Based upon the methods of the hereinbefoe presented examples, and employing standard recombinant techniques well known by those skilled in the art, the human IRAP gene was incorporated into an MFG vector as shown in FIG. 1. Following the infection of synoviocyte cultures of rabbit origin with this viral vector, IRAP was secreted into the culture medium.

Figure 4:
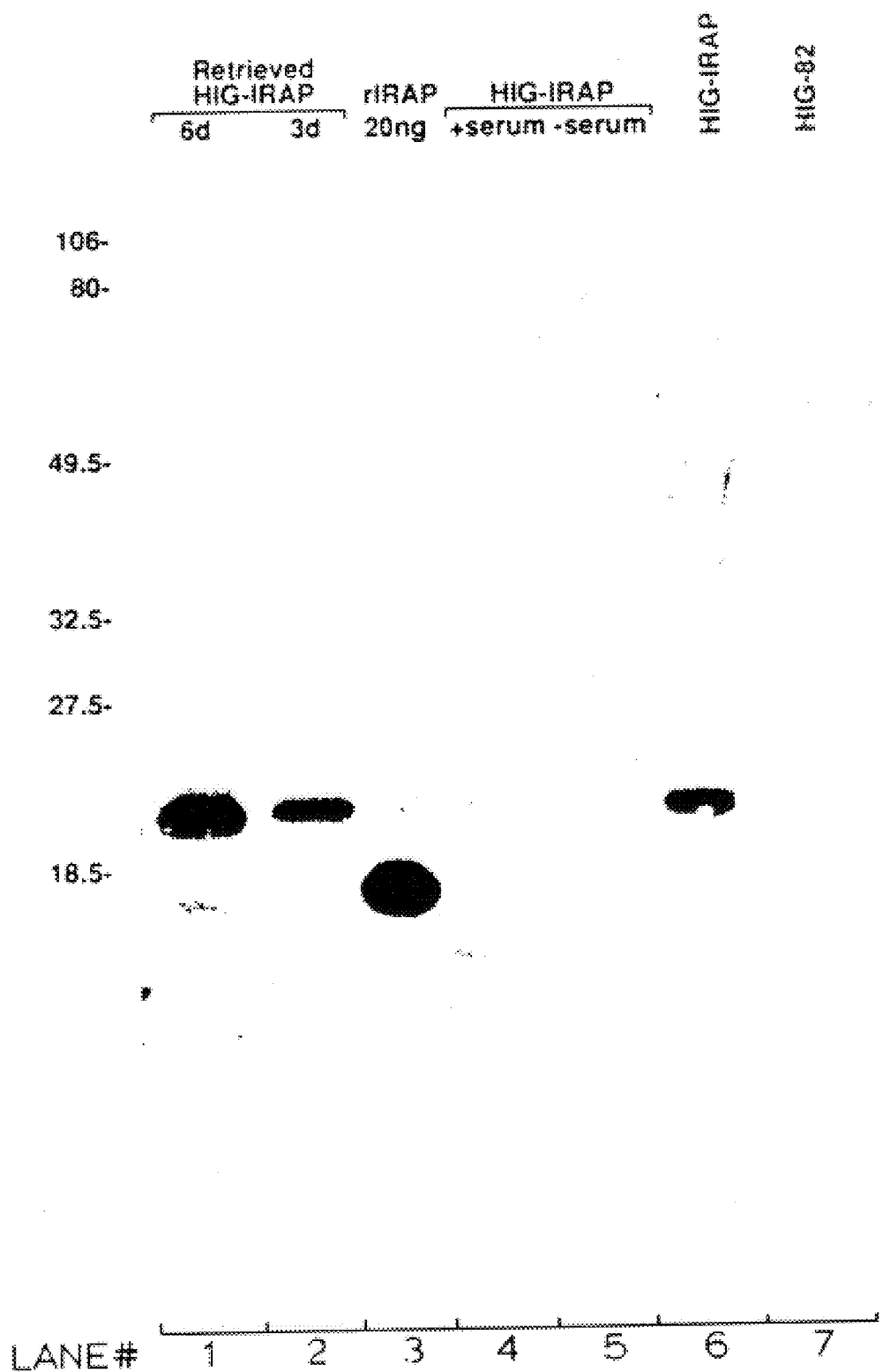
FIG. 4 shows a Western blot demonstrating the production of interleukin-1 recepor antagoist protein by four cultures of HIG-82 cells (Georgescu 1988) infected using the method of this invention employing the MFG-IRAP viral vector.

Western blotting, well known by those skilled in the art, was carried out using an IRAP-specific rabbit polyclonal antibody that does not recognize human or rabbit IL-1alpha or IL-1beta, or rabbit IRAP. FIG. 4 shows a Western blot which sets forth the production of IRAP by four cultures of HIG-82 cells infected with MFG-IRAP. Three forms of the IRAP are present: a non-glycosylated form which runs with recombinant standards, and two larger glycosylated forms. The results of the Western blotting shown in FIG. 4 demonstrated that IRAP was produced by HIG-82 synoviocyte cell line (Georgescu, 1988) following infection with the MFG-IRAP vector of this invention. The Western blotting of FIG. 4 shows the IRAP concentration of the conditioned medium is as high as 50 ng/ml. This is approximately equal to 500 ng IRAP/$10^6$ cells/day. Lane 1 and Lane 2 of FIG. 4 show that the recipient synovia tissue secrete substantial amounts of HIG-IRAP at 3 days (Lane 2) and 6 days (Lane 1). Lane 3 shows human recombinant IRAP. Lane 6 indicates that rabbit synovial cells produce a larger glycosylated version of this molecule after infection with MFG-IRAP. Lane 7 indicates that native rabbit synovial cells do no produce this glycosylated form.

Figure 5A:
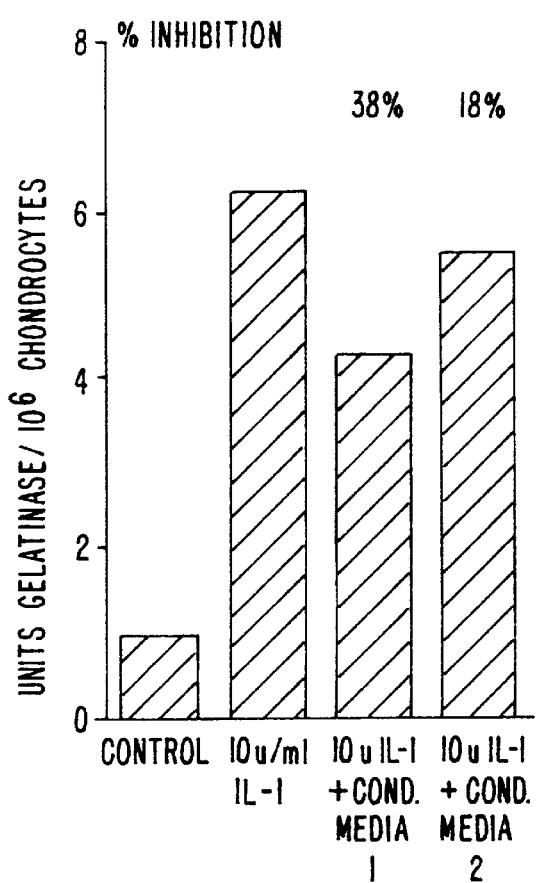
FIG. 5 shows data demonstrating the inhibition of gelatinase production by chondrocytes by the addition of medium conditioned by MFG-IRAP infected HIG-82 cells.
Figure 5B:
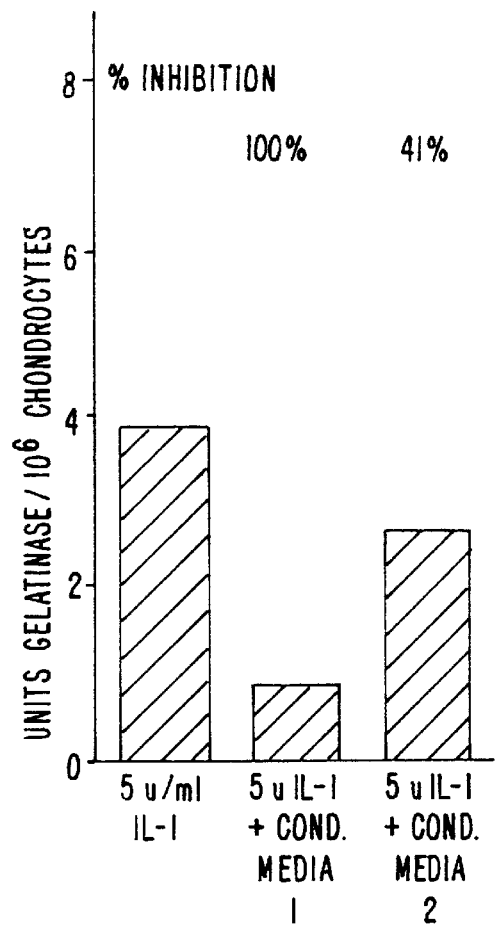

FIG. 5 shows that medium conditioned by IRAP$^+$ synoviocytes blocks the induction of matrix metalloproteinases in articular chondrocytes exposed to recombinant human IL-1 beta. Chondrocytes normally secrete 1 U/$10^6$ cells, or less, gelatinase into their culture media. FIG. 5 shows that when to about 5 U/ml or 10 U/ml IL-1are added, gelatinase production increases to over 4 U and 6 U/$10^8$ cells, respectively. Addition of medium conditioned by MFG-IRAP-infected HIG-82 cells employed by the method of this invention suppressed gelatinase production by IL-1 treated chondrocytes. With 5 U/ml IL-1 (FIG. 5, right panel) inhibition was 100% for one culture and 51% for the other. With 10 U/ml IL-1, inhibition was reduced to 38% and 18% (FIG. 5, left panel) as is expected of a competitive inhibitor. These data demonstrate that the IRAP produced by HIG-82 cells infected with MFG-IRAP is biologically active.

Example IX

This example demonstrates the uptake and expression of Lac Z gene by synoviocytes using infection by a liposome (lipofection). A six well plate containing synoviocyte cultures were transduced with the Lac Z gene by lipofection. The content of each well is as follows:

| Well 1 | Control cells, treated with liposomes alone |
|---|---|
| Well 2 | Control cells, treated with DNA alone |
| Well 3 | DNA + 150 nmole liposomes |
| Well 4 | DNA + 240 nmole liposomes |
| Well 5 | DNA + 300 nmole liposomes |
| Well 6 | DNA + 600 nmole liposomes |

Figure 6:
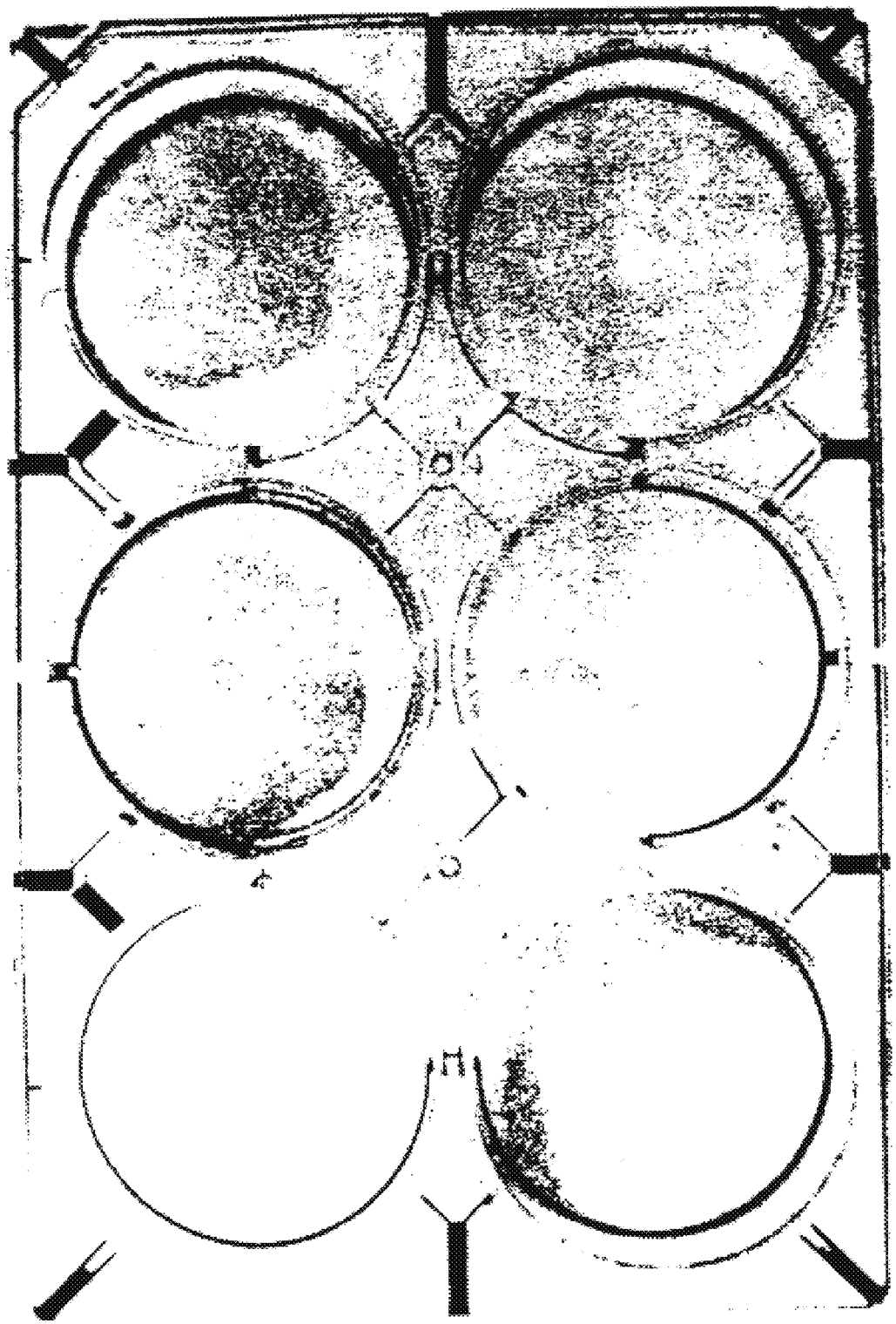
FIG. 6 shows the uptake and expression of the Lac Z gene by synoviocytes using lipofection. Well 1—Control cells, treated with liposomes alone; Well2—Control cells, treated with DNA alone; Well3—DNA+150 nmole lipsomes; Well4—DNA+240 nmole liposomes; Well5—DNA+300 nmole lipsomes; Well6—DNA+600 nmole liposomes.

Wells 3–6 containing sub-confluent cultures of synovial fibroblasts were transfected with 6 ug of DNA complexed with 150–600 nmoles/well of "DC-chol" liposome or in the alternative, with "SF-chol". Three days later, cells were stained histochemically for expression of beta-galactosidase (FIG. 6).

Table 1 shows the results of using the liposomes "DC-chol" and "SF-chol" in converting synoviocyte cultures to the Lac Z$^+$ phenotype without selection. Table 1 sets forth that the "DC-chol" liposome in a concentration of about 300 nmole/well converted generally 30% of the synovial cells in synoviocyte cultures to the Lac Z$^+$ phenotype without selection. Reduced expression was shown in Well 6 for "DC-chol" due to the toxic effect of the high liposome concentration.

TABLE 1

| Liposome, nmole/well | % Lac Z⁺ Cells | |
| --- | --- | --- |
| | DC-chol | SF-chol |
| 150 | 10 | 0.5 |
| 240 | 22 | 1.0 |
| 300 | 30 | 2.8 |
| 600 | NA | 3.5 |

In another embodiment of this invention, a gene and method of using this gene provides for the neutralization of interleukin-1. Interleukin-1 is a key mediator of cartilage destruction in arthritis. Interleukin-1 also causes inflammation and is a very powerful inducer of bone resorption. Many of these effects result from the ability of interleukin-1 to increase enormously the cellular synthesis of prostaglandins and various proteinases including collagenase, gelatinase, stromelysin, plasminogen activator and aggrecanase. The catabolic effects of interleukin-1 upon cartilage are exacerbated by is ability to suppress the synthesis of the cartilaginous matrix by chondrocytes. Interleukin-1 is present at high concentrations in synovial fluids aspirated from arthritic joints and it has been demonstrated that intra-articular injection of recombinant interleukin-1 in animals causes cartilage breakdown and inflammation.

Figure 7:
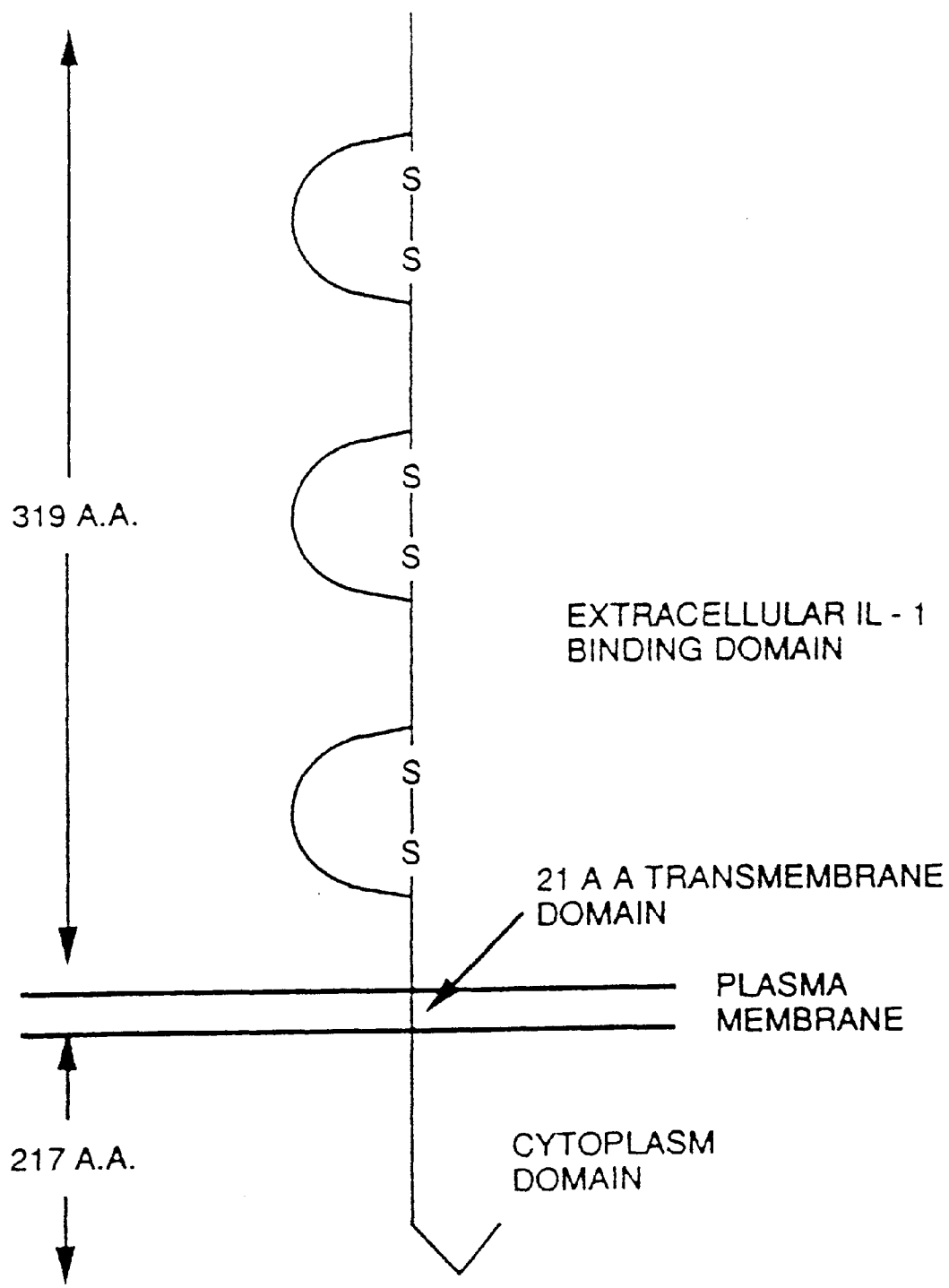
FIG. 7 shows the interleukin-1 binding domain amino acid arrangement.
Figure 8A:
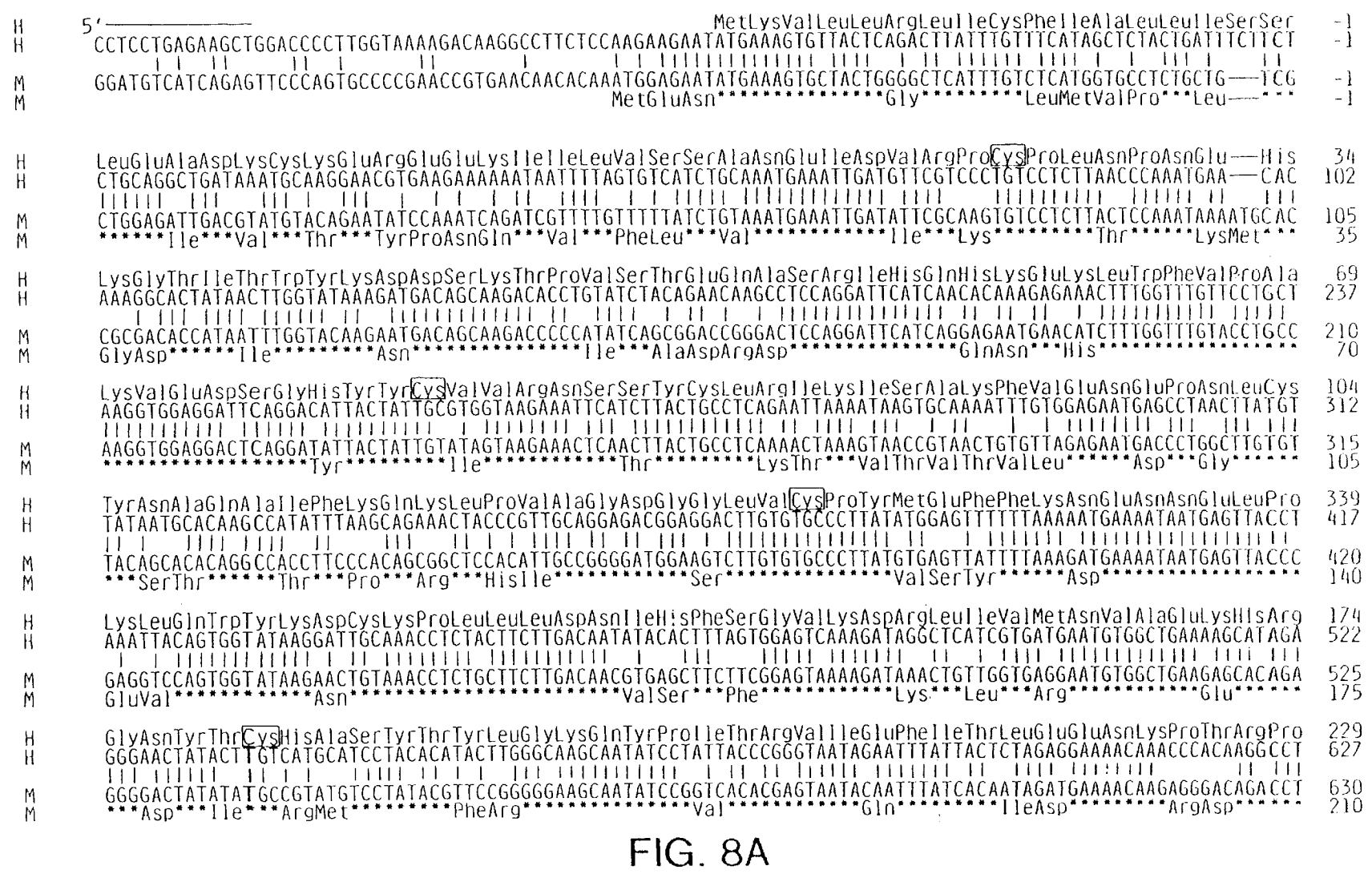
Figure 8B:
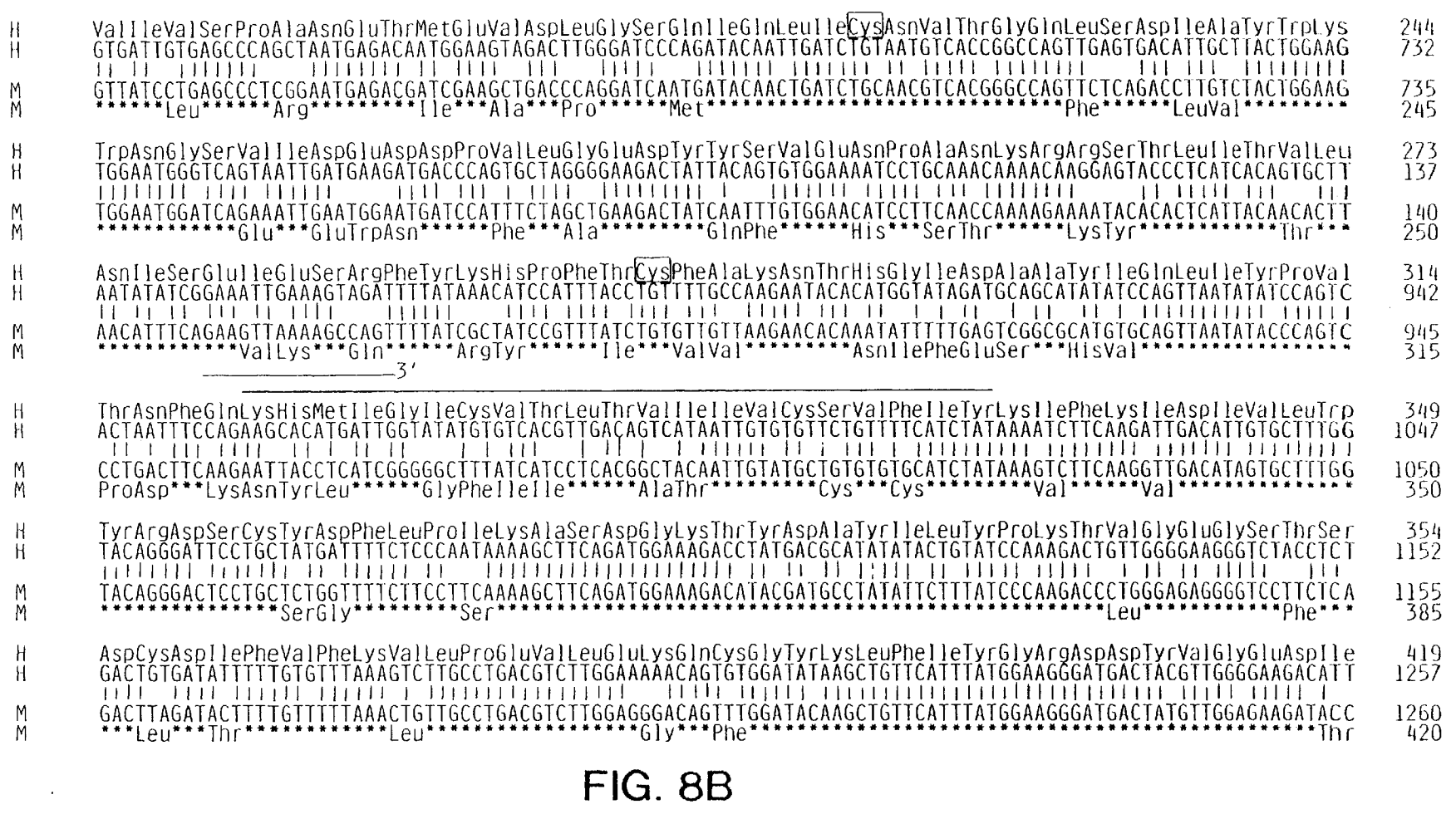

Interleukin-1 exists as several species, such as unglycosylated polypeptide of 17,000 Daltons. Two species have previously been cloned, interleukin-1 alpha and interleukin-1 beta. The alpha form has a pI of approximately 5, and the beta form as a pI around 7. Despite the existence of these isoforms, interleukin-1 alpha and interleukin-1 beta have substantially identical biological properties and share common celyl surface receptors. The type I interleukin-1 receptor is a 80 kDa (kilodalton) glycoprotein and contains an extracellular, interleukin-1 binding portion of 319 amino acids which are arranged in three immunoglobulin-like domains held together by disulfide bridges as shown in FIG. 7. A 21 amino acid trans-membrane domain joins the extracellular portion to the 217 amino acid cytoplasmic domain. FIGS. 8A–8C show the amino acid and nucleotide sequence of the human and mouse interleukin-1 receptors. In FIG. 8B, the 21 amino acid trans-membrane region of the interleukin-1 receptor is marked by the thicker solid line. In FIGS. 8A and 8B, the position of the 5' and 3' oligonucleotides for PCR are marked by thinner short lines, respectively. The lysine amino acid just 5' to the trans-membrane domain to be mutated to a stop codon is marked by a solid circle in FIG. 8B.

Synovium is by far the major, and perhaps the only, intraarticular source of interleukin-1 in the arthritic joint. Synovia recovered from arthritic joints secrete high levels of interleukin-1. Both the resident synoviocytes and infiltrating blood mononuclear cells within the synovial lining produce interleukin-1.

The present invention provides a method of using in vivo a gene coding for a truncated form of the interleukin-1 receptor which retains its ability to bind interleukin-1 with high affinity but which is released extracellularly and therefore inactive in signal transduction. The binding of this truncated and modified receptor to interleukin-1 inhibits the intraarticular activity of interleukin-1.

This method of using a gene encoding the extracellular interleukin-1 binding domain of an interleukin-1 receptor that is capable of binding to and neutralizing interleukin-1 includes employing a retroviral vector carrying a truncated interleukin-1 receptor gene which encodes a truncated and soluble active form of the receptor. The expression of the novel interleukin-1 receptor gene is controlled by regulatory sequences contained within the vector that are active in eukaryotic cells. This recombinant viral vector is transfected into cell lines stably expressing the viral proteins in trans required for production of infectious virus particles carrying the recombinant vector. These viral particles are used to deliver the recombinant interleukin-1 receptor to the recipient synovial cells by direct virus infection in vivo.

The soluble human interleukin-1 receptor to be inserted into the retroviral vector may be generated by a polymerase chain reaction (PCR). An oligonucleotide complementary to the 5' leader sequence of the human interleukin-1 receptor (GCGGATCCCCTCCTGAGAAGCT; SEQ ID NO:5) and an oligonucleotide complementary to a region just upstream from the transmembrane domain of the interleukin-1 receptor (GCGGATCCCATGTGCTACTGG; SEQ ID NO:6) are used a primers for PCR. The primer for the region of the interleukin-1 receptor adjacent to the trans-membrane domain contains a single base change so that the lys codon at amino acid 336 of SEQ ID NOS:1 and 2 (AAG) is changed to a stop codon (TAG). By inserting a translation stop codon just upstream from the transmembrane domain, a truncated form of interleukin-1 receptor that is secreted by the cell is generated. A BamHI recognition sequence (GGATCC) is added to the 5' end of the PCR primers, and following amplification, the resulting interleukin-1 receptor fragment is cloned into a BamHI site. A cDNA library from human T-cells is used as a source for the interleukin-1 receptor cDNA. To amplify the appropriate region of the interleukin-1 receptor from the cDNA library, the complementary primers are added to the DNA and 50 cycles of annealing, primer extension and denaturation are performed using a thermocycler and standard PCR reaction conditions well known by those persons skilled in the art. Following amplification of the interleukin-1 soluble receptor using the PCR process, the resulting fragment is digested with BamHI and inserted into the pLJ retroviral vector. The pLJ retroviral vector is available from A. J. Korman and R. C. Mulligan. See also *Proc. Natl. Acad. Sci.,* Vol. 84, pp. 2150–2154 (April 1987) co-authored by Alan J. Korman, J. Daniel Frantz, Jack L. Strominger and Richard C. Mulligan. Restriction analysis was performed to determine the correct orientation of the insert. It could also be cloned into MFG.

The retrovirus vector carrying the truncated interleukin-1 receptor is transferred into the CRIP (*Proc. Natl. Acad. Sci.,* Vol. 85, pp. 6460–6464 (1988), O. Danos and R. C. Mulligan) packaging cell line using a standard $Ca_3(PO_4)_2$ transfection procedure and cells wherein the viral vector is stably integrated and is selected on the basis of resistance to the antibiotic G418. The viral vector containing the neomycin resistant (neo-r) gene is capable of imparting resistance of the cell line to G418. The CRIP cell line expresses the three viral proteins required for packaging the vector viral RNAs into infectious particles. Moreover, the viral particles produced by the CRIP cell line are able to efficiently infect a wide variety of mammalian cell types including human cells. All retroviral particles produced by this cell line are defective for replication but retain the ability to stably integrate into synovial cells thereby becoming an heritable trait of these cells. Virus stocks produced by this method are substantially free of contaminating helper-virus particles and are also non-pathogenic.

Figure 9:
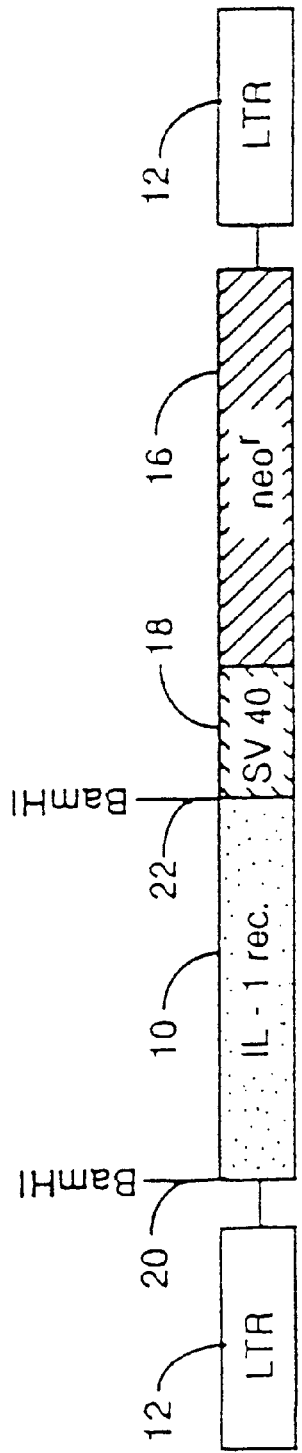
FIG. 9 shows gene encoding a soluble interleukin-1 receptor inserted into a retroviral vector.

More specifically, the truncated interleukin-1 gene can be inserted into a retroviral vector under the regulation of a suitable eukaryotic promoter such as the retroviral promoter already contained within the gene transfer vector, such as for example, the pLJ vector shown in FIG. 9. FIG. 9 shows the structure of the pLJ interleukin receptor retroviral vector and partial restriction endonuclease map. Reference numeral 10 shows the interleukin-1 receptor inserted into a retroviral vector. Reference numeral 12 indicates long terminal repeats (LTR's) at each end of the structure of the pLJ interleukin receptor retroviral vector shown in FIG. 8. These LTR's regulate the viral transcription and expression of the interleukin-1 receptor. Bacterial gene encoding resistance to the antibiotic neomycin (neo-r) is shown at reference number 16. The Simian Virus 40 enhancer promoter (SV 40) is indicated at reference numeral 18, and regulates the expression of the neo-r gene. Reference numbers 20 and 22, respectively, show the sites wherein the resulting interleukin receptor fragment is cloned. It will be understood by those persons skilled in the art that other vectors containing different eukaryotic promoters may also be utilized to obtain a generally maximal level of interleukin-1 receptor expression. The vectors containing the truncated, and modified interleukin-1 receptor will be introduced into a retroviral packaging cell line (CRIP) by transfection and stable transformants isolated by selection for the expression of the neomycin resistance gene also carried by the pLJ vector. The CRIP cell line expresses all the proteins required for packaging of the exogenous retroviral RNA. Viral particles produced by the G418-selected CRIP cell lines will carry a recombinant retrovirus able to infect mammalian cells and stably express the interleukin-1 truncated receptor. The viral particles can be used to infect synovial cells directly in vivo by injecting the virus into the joint space or alternatively in vitro as part of the ex vivo transplantation methods of the present invention.

Another embodiment of this invention provides a method for using the hereinbefore described viral particles to infect in culture synovial cells obtained from the lining of the joint of a mammalian host. The advantage of the infection of synovial cells in culture is that infected cells harboring the interleukin-1 receptor retroviral construct can be selected using G418 for expression of the neomycin resistance gene. The infected synovial cells expressing the interleukin-1 receptor can then be transplanted back into the joint by intra-articular injection. The transplanted cells will express high levels of soluble interleukin-1 receptor in the joint space thereby binding to and neutralizing substantially all isoforms of interleukin-1, including interleukin-1 alpha and interleukin-1 beta.

The method used for transplantation of the synovial cells within the joint is a routine and relatively minor procedure used in the treatment of chronic inflammatory joint disease. Although synovium can be recovered from the joint during open surgery, it is now common to perform synovectomies, especially of the knee, through the arthroscope. The arthroscope is a small, hollow rod inserted into the knee via a small puncture wound. In addition to permitting the intraarticular insertion of a fibre-option system, the arthroscope allows access to surgical instruments, such that synovial tissue can be removed arthroscopically. Such procedures can be carried out under "spinal" anesthetic and the patient allowed home the same day. In this manner sufficient synovium can be obtained from patients who will receive this gene therapy.

The synovial cells (synoviocytes) contained within the excised tissue may be aseptically recovered by enzymic digestion of the connective tissue matrix. Generally, the synovium is cut into pieces of approximately 1 millimeter diameter and digested sequentially with trypsin (0.2% w/v in Gey's Balanced Salt Solution) for 30 minutes at 37° Centigrade, and collagenase (0.2% w/v in Gey's Balanced Salt Solution) for 2 hours at 37° Centigrade. Cells recovered from this digestion are seeded into plastic culture dishes at a concentration of $10^4$–$10^5$ cells per square centimeter with Ham's $F_{12}$ medium supplemented with 10% fetal bovine serum and antibiotics. After 3–7 days, the culture medium is withdrawn. Non-adherent cells such as lymphocytes are removed by washing with Gey's Balanced Salt Solution and fresh medium added. The adherent cells can now be used as they are, allowed to grow to confluency or taken through one or more subcultures. Subcultivating expands the cell number and removes non-dividing cells such as macrophages.

Following genetic manipulation of the cells thus recovered, they can be removed from the culture dish by trypsinizing, scraping or other means, and made into a standard suspension. Gey's Balanced Salt Solution or other isotonic salt solutions of suitable composition, or saline solution are suitable carriers. A suspension of cells can then be injected into the recipient mammalian joint. Intra-articular injections of this type are routine and easily carried out in the doctor's office. No surgery is necessary. Very large numbers of cells can be introduced in this way and repeat injections carried out as needed.

Another embodiment of this invention is the gene produced by the hereinbefore described method of preparation. This gene carried by the retrovirus may be incorporated in a suitable pharmaceutical carrier, such as for example, buffered physiologic saline, for parenteral administration. This gene may be administered to a patient in a therapeutically effective dose. More specifically, this gene may be incorporated in a suitable pharmaceutical carrier at a therapeutically effective dose and administered by intra-articular injection.

In another embodiment of this invention, this gene may be administered to patients as a prophylactic measure to prevent the development of arthritis in those patients determined to be highly susceptible of developing this disease. More specifically, this gene carried by the retrovirus may be incorporated in a suitable pharmaceutical carrier at a prophylactically effective dose and administered by parenteral injection, including intraarticular injection.

EXAMPLE X fifty micrograms of a DNA plasmid vector molecule containing the interleukin-1 beta coding sequence ligated downstream of the CMV promoter was encapsulated within cationic liposomes, mixed with Geys biological buffer and injected intraarticularly into the knee joints of a rabbit. Forty eight hours subsequent to injection one nanogram of interleukin-1 beta was recovered from the knee joint area. Therefore, injection of the DNA containing liposome solution within the region of the synovial tissue prompted fusion of the liposomes to the synovial cells, transfer of the DNA plasmid vector into synovial cells and subsequent expression of the IL-1 beta gene. Additionally, it is possible to inject non-encapsulated (i.e., naked) DNA into the joint area and monitor transfection of the DNA vector into the synovial cells ad determined by subsequent expression of the IL-1 beta gene in synovial cells. Therefore, either method may be utilized as a plausible alternative to the in vitro manipulation of synovial also exemplified in the present invention.

EXAMPLE XI

Figure 10:
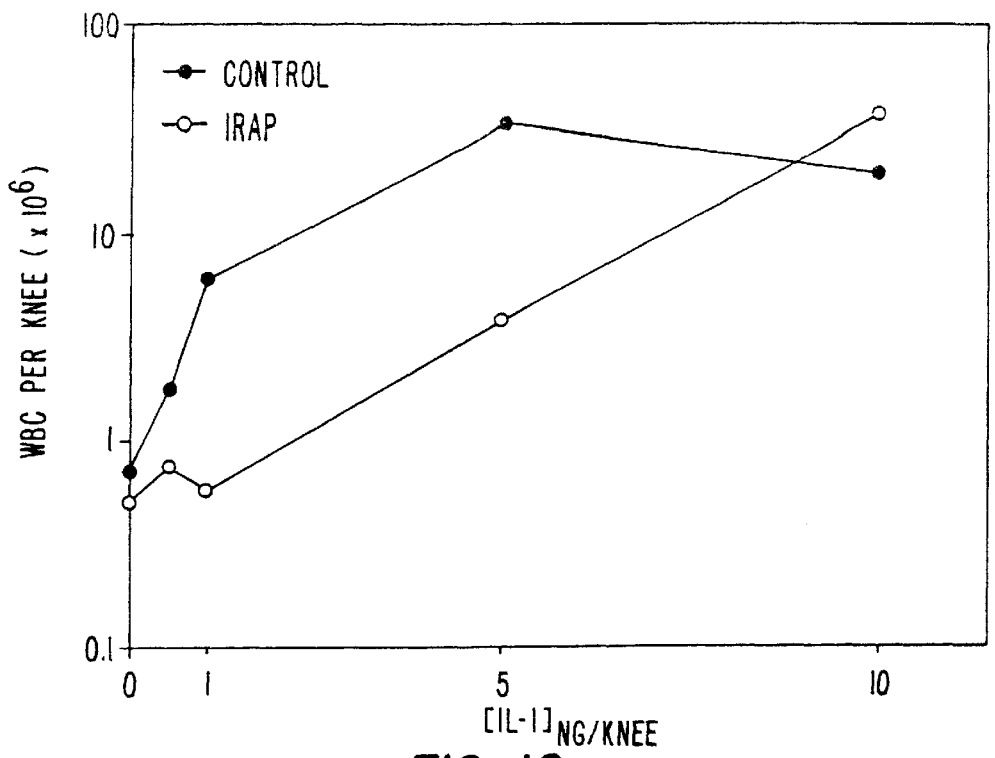
FIG. 10 shows anti-inflammatory properties of the MG-IRAP transgene. MFG-IRAP/HIG-82 cells ($10^7$) or untransduced HIG-82 cells ($10^7$) were transplanted to the knee joints of rabbits 3 days before intraarticular challenge with the indicated amounts of recombinant human interleukin-1beta (rhIL-1β). Lavage of joints occurred 18 hours later, after which infiltrating leukocytes were counted.

The in vivo biological activity of the MFG-IRAP construct was tested as the ability to suppress the effects of IL-1β. Rabbit knees were injected with recombinant human IL-1β, known to cause an increased concentration of leukocytes within the afflicted joint space. Introduction of MFG-IRAP/HIG-82 cells into rabbit knees strongly suppresses IL-1β production of leukocytes to the afflicted joint space. In contrast, control HIG-82 cells do not suppress the leukocyte infiltration to the joint space challenged with IL-1β (see FIG. 10). Inhibition is greatest at the lowest doses of human recombinant IL-1β (hrIL-1β), as expected by the competitive mechanism through which IRAP antagonizes IL-1. Therefore, this rabbit model confirms that in vivo, intra-articular expression of IRAP is biologically active and can protect the joint from inflammation provoked by IL-1.

EXAMPLE XII

This example further evaluates ex vivo delivery into rabbit knee joints of the MFG-IRAP construct. As known, IRAP is an acidic glycoprotein of approximately 25 kDa that functions as a natural antagonist of the biological actions of interleukin-1 (IL-1) by binding to IL-1 receptors. Unlike IL-1, IRAP has no agonist activity, instead acting as a competitive inhibitor of the binding of IL-1.

This example shows that in vivo expression of IRAP by genetically modified synovial cells inhibits IL-1β-induced leukocyte infiltration into the joint space, synovial thickening and hypercellularity, and loss of proteoglycans from articular cartilage.

As disclosed within this specification, the preferred mode of treating a patient through the ex vivo route will be by transplanting genetically modified autologous synovial cells by intra-articular injection. However, HIG-82 cells, easily maintained in culture, were used for these experiments to show that intra-articularly expressed IRAP is effective in inhibiting the physiological sequelae of intra-articularly injected IL-1.

MFG-IRAP/HIG-82 cells or control (uninfected HIG-82) cells, were transplanted into rabbit knees by intra-articular injection by the methods disclosed within this specification. Briefly, cultures of these cells were infected with MFG-IRAP. Media conditioned for 3 days by infected MFG-IRAP/HIG 82 cells were assayed for human IRAP by ELISA assay using a commercial kit (R&D Systems, Minneapolis, Minn., USA) and found to contain approximately 500 ng IRAP/$10^6$ cells. Western blotting confirmed the presence of human IRAP of size 22–25 kDa. HIG-IRAP cells were trypsinized, suspended in Gey's balanced salt solution and 1 ml of suspension, containing $10^7$ cells, was injected intra-articularly into the left knee joints of New Zealand White rabbits (2.5 kg). The untreated control knees received a similar injection of untransduced HIG-82 cells.

Three days following transplantation of the cells, knee joints were challenged by various doses of a single intra-articular injection of human recombinant IL-1β dissolved in 0.5 ml Gey's solution. Control knees were injected with 0.5 ml of Gey's solution.

Eighteen hours after injection of hrIL-1β, rabbits were killed and the knee joints evaluated histopathologically and for expression of IRAP. Each joint was first lavaged with 1 ml Gey's solution containing 10 mM EDTA. Cell counts in these washings were performed with a hemocytometer. An aliquot was removed for cytospinning and staining with 'DiffQuick' (Baxter Scientific Products) before examination under light microscopy. Washings were then centrifuged. Supernatants were removed for IRAP ELISA and for the determination of glycosaminoglycan (GAG) concentrations as an index of cartilage breakdown. GAG determinations were carried out with the dimethylmethylene blue assay (Farndale, et al., *Biochim. Biophys. Acta.* 883:173–177 (1986)).

Synovia were dissected from the knee joints, fixed in 70% ethanol, dehydrated, embedded in paraffin, sectioned at 5 μm and stained with hematoxylin and eosin.

Figure 11:
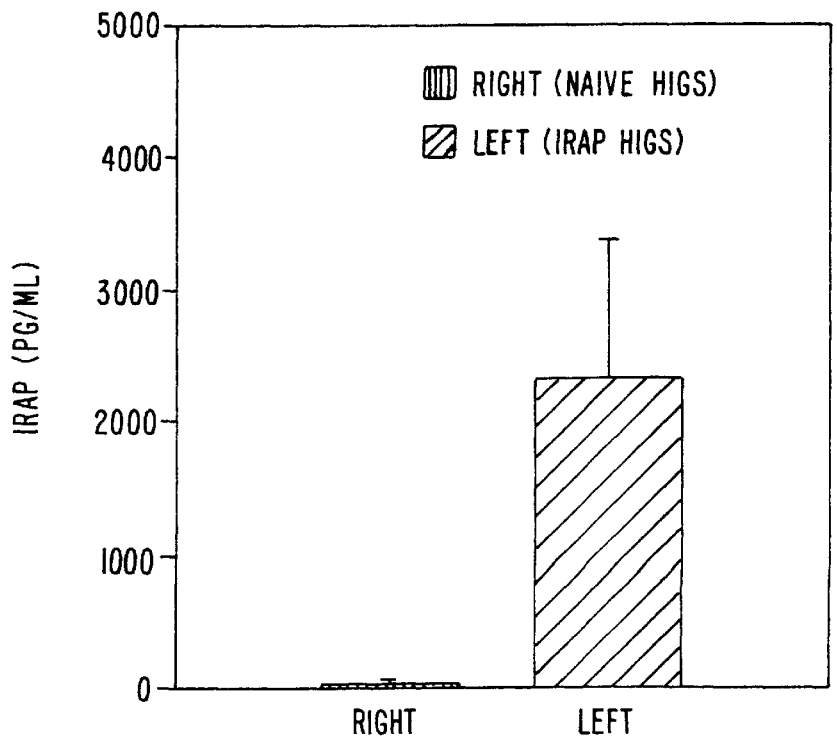
FIG. 11 shows levels of human IRAP in rabbit knees four day following transplant of synoviocytes. Either untransduced (naive) HIG-82 cells or cells carrying a human IRAP gene (MGF-IRAP/HIG-82) were injected intraarticularly in the knee joints or rabbits ($10^7$ cells/knee). Four days later, knees were lavaged and the concentration of human IRAP determined by ELISA. Values given are means ±S.D. (N=15).
Figure 12A:
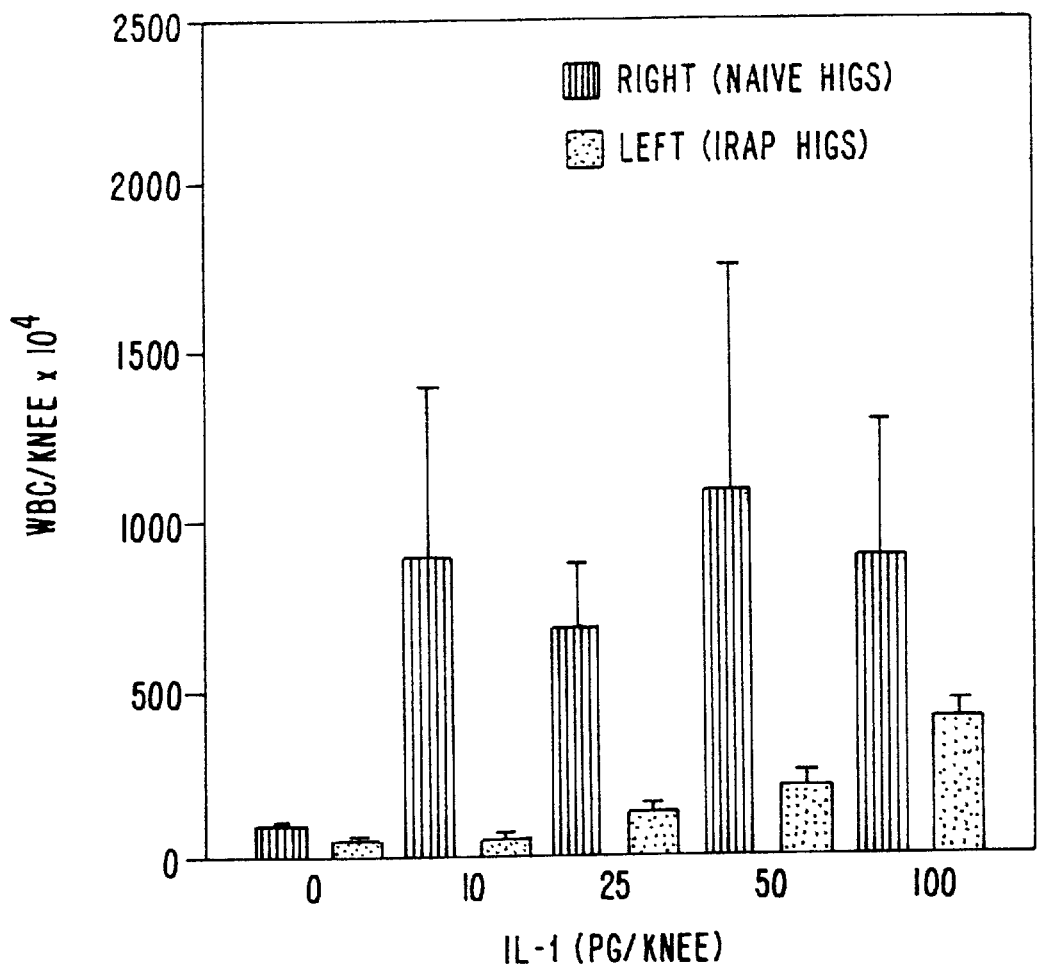
FIG. 12(A–C) shows inhibition of IL-1 induced leukocyte infiltration in knees expressing IRAP gene. Either naive or IRAP-transduced HIG-82 cells were transplanted into rabbit knee joints, as indicated. Three days later 0–100 pg/knee hIL-1β was intraarticularly injected at the indicated doses. The following day, knee joints were lavaged and the leukocytic infiltrate analyzed by counting with a hemocytometer and by cytospinning. Means ±S.E. (n=3). (a) White blood cells (WBC) per knee. (b) Stained cytospin preparation of lavages from control knee injected with IL-1. Preparation was diluted 1:10 prior to cytospinning. (c) Stained cytospin preparation of lavages from IRAP secreting knee injected with IL-1. the preparation was not diluted.

An average of 2.5 ng human IRAP per knee was measured in joint lavages 4 days following transplant of MFG-IRAP/HIG 82 cells. Untreated, control knees receiving naive HIG-82 cells had no detectable human IRAP (FIG. 11). To determine whether the observed level of IRAP expression was sufficient to inhibit the effects of IL-1 in vivo, increasing concentrations of IL-1β (0–100 pg) were injected into both the control and IRAP knees. As is shown in FIG. 12a, injection of hrIL-1β into control knees provoked a marked leukocytosis which was strongly suppressed in the genetically modified knees. There was also a statistically significant reduction in the white blood cell count in knees containing MFG-IRAP/HIG 82 cells which had not been injected with IL-1. This may reflect the influence of IRAP upon the slight inflammatory effect of injecting cells into joints. The degree of suppression of IRAP decreased as the amount of injected hrIL-1β increased, in keeping with the competitive mode of inhibition existing between IRAP and IL-1. No dose-response for hrIL-1β alone is evident in these particular experiments because this specific batch of IL-1 was especially effective in eliciting maximal response even at the lowest dose used.

Figure 12B:
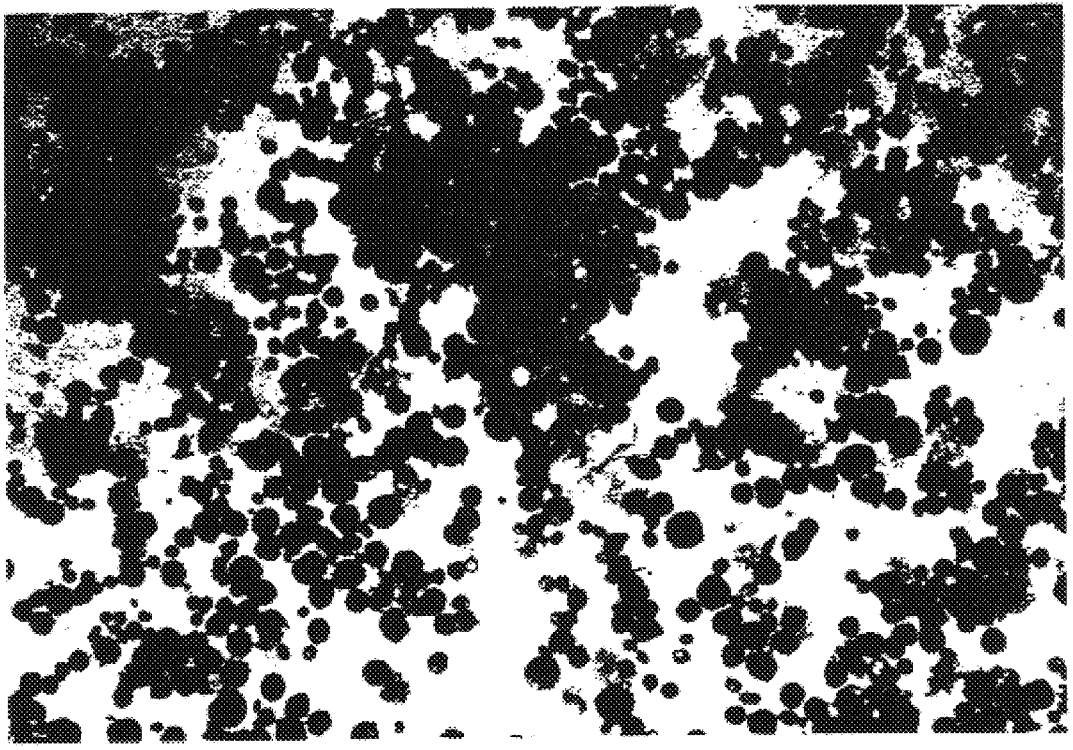
Figure 12C:
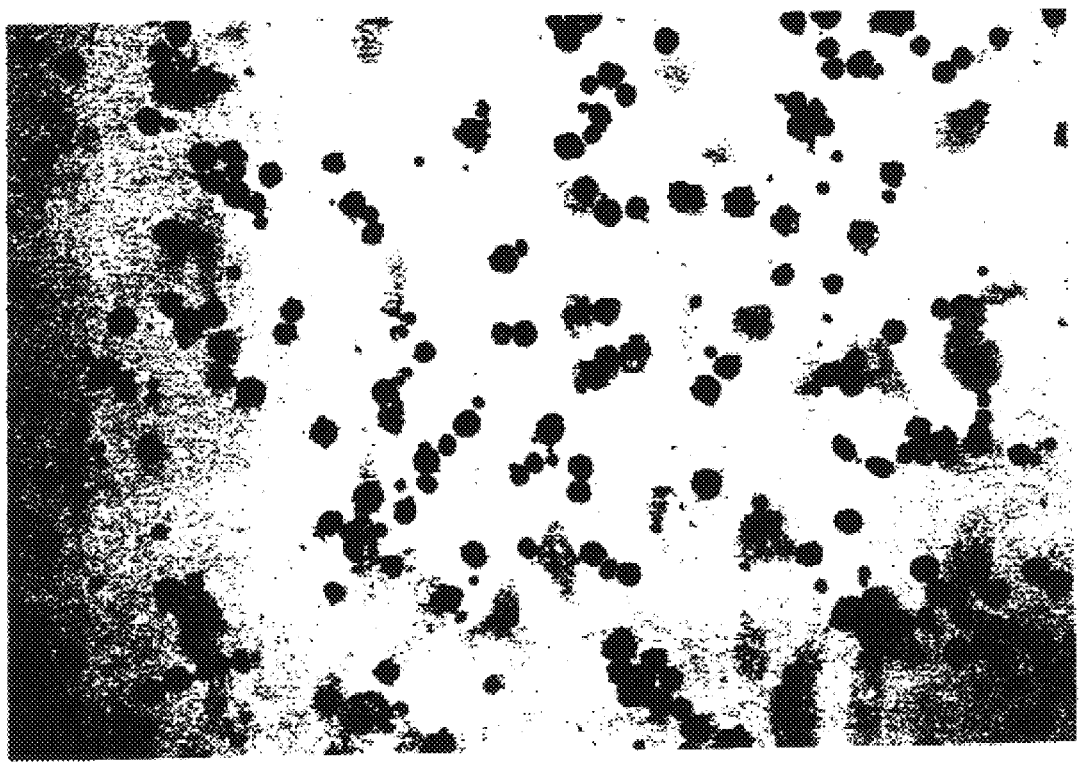

Examination of cytospins (FIG. 12b, 12c) revealed that most of the infiltrating leukocytes were neutrophils and monocytes. These preparations also serve to illustrate the efficiency with which leukocytosis was suppressed by the IRAP gene. Ten times the volume of lavage fluid is represented on the cytospin obtained from the IRAP-producing knees (FIG. 12c) compared to the non-IRAP knees (FIG. 12b).

Figure 13:
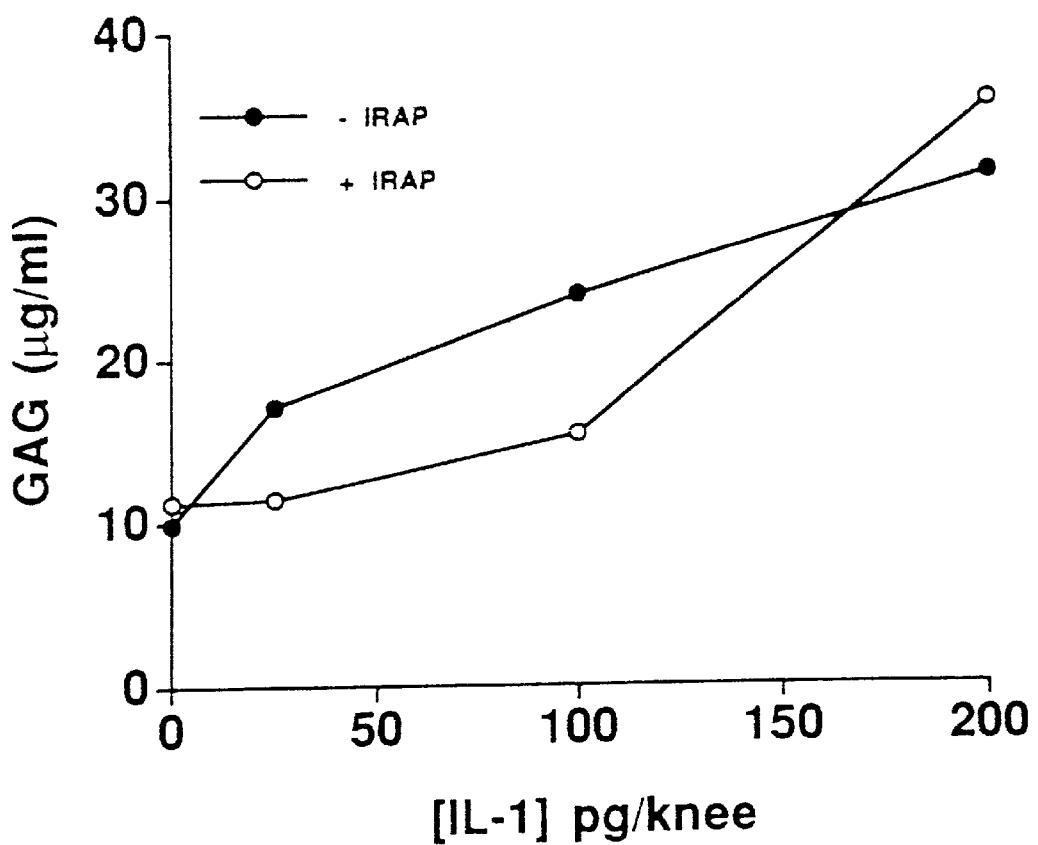
FIG. 13 shows suppression of IL-1induced loss of proteoglycans from articular cartilage. Either naive or IRAP-transduced HIG-82 cells were transplanted into rabbits knee joints. Three days later, 0–200 pg/knee hrIL-1 was intraarticularly injected at the indicated doses. The following day, knee joints were lavaged and the level of glycosaminoglycans (GAG) as an index of cartilage breakdown was determined.

To determine if intra-articularly expressed IRAP was able to block cartilage breakdown, the concentration of glycosaminoglycans (GAG) in joint lavages was determined. GAG analyses of the washings from the control and IRAP expressing knees (FIG. 13) confirmed that transfer of the IRAP gene partially inhibited breakdown of the cartilaginous matrix in response to IL-1. Again, inhibition was strongest at the lowest concentrations of IL-1 and was abolished at the highest dose of IL-1 (FIG. 13).

Figure 14A:
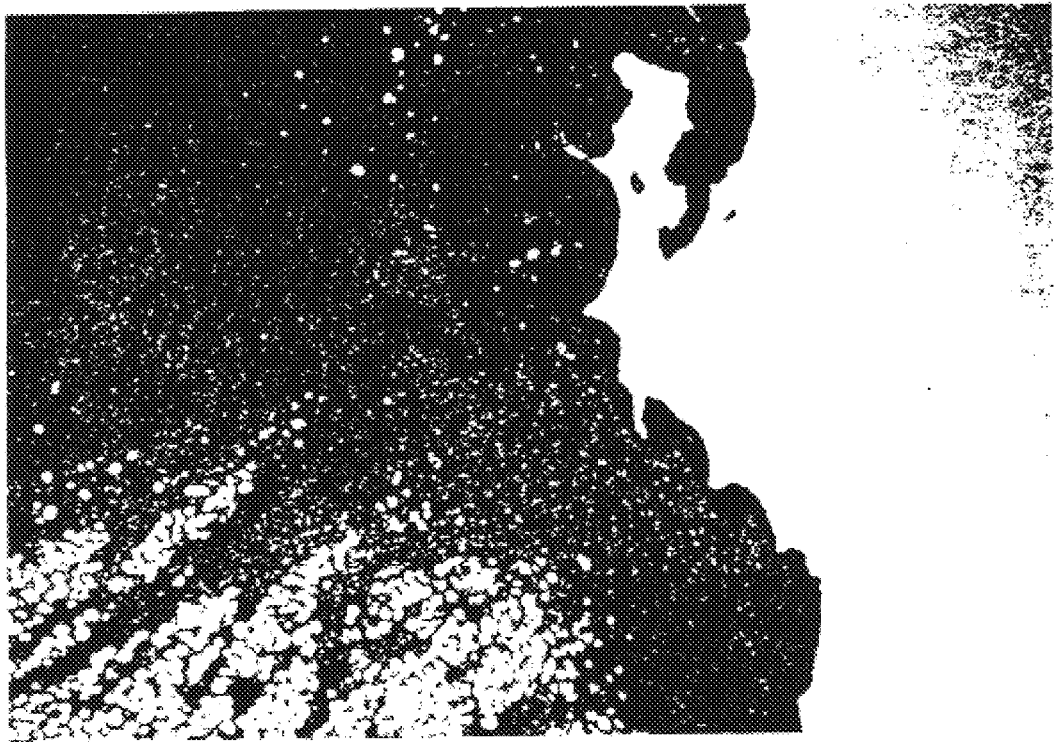
FIG. 14(A–D) shows suppression of IL-1 mediated synovial changes in knees expressing IRAP. Ten pg hrIL-1 B was injected intraarticularly in each case. Synovia were harvested 18 hours after injection of IL-1β, i.e. 4 days after transplantation of naive or IRAP-secreting HIG-82 cells. (a) Control synovium following injection of IL-1, magnification ×10. (b) IRAP-secreting synovium following injection of IL-1, magnification ×10. (c) Control synovium following injection of IL-1, magnification ×160. (d) IRAP-secreting synovium, magnification ×160.
Figure 14B:
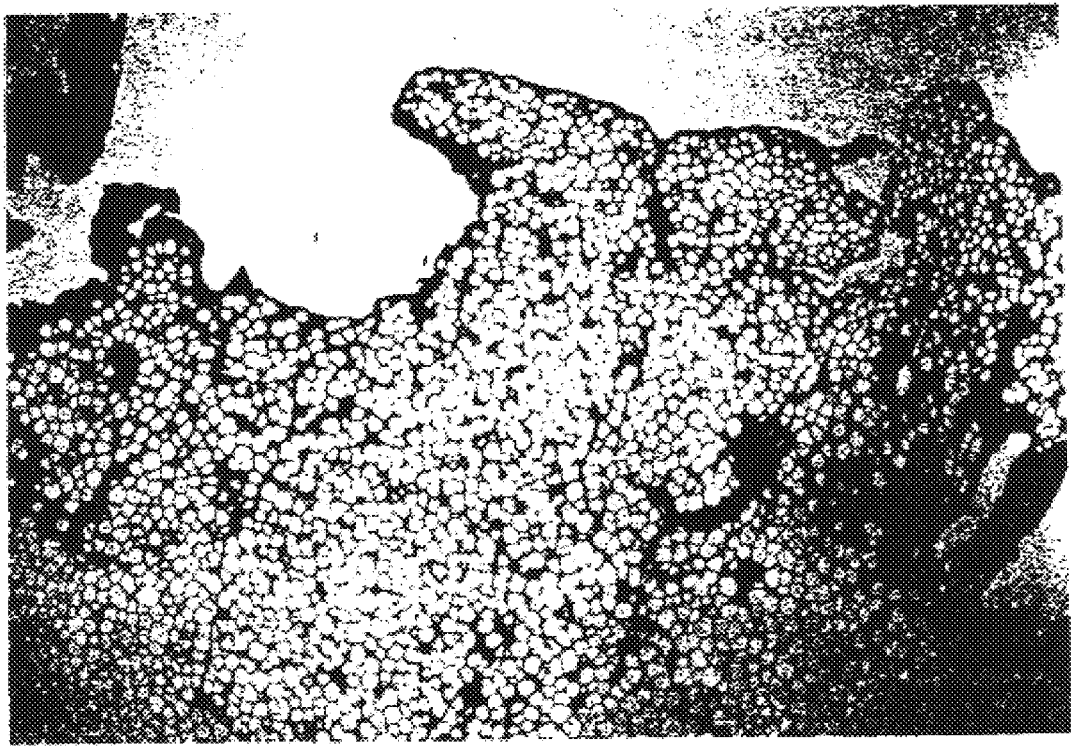
Figure 14C:
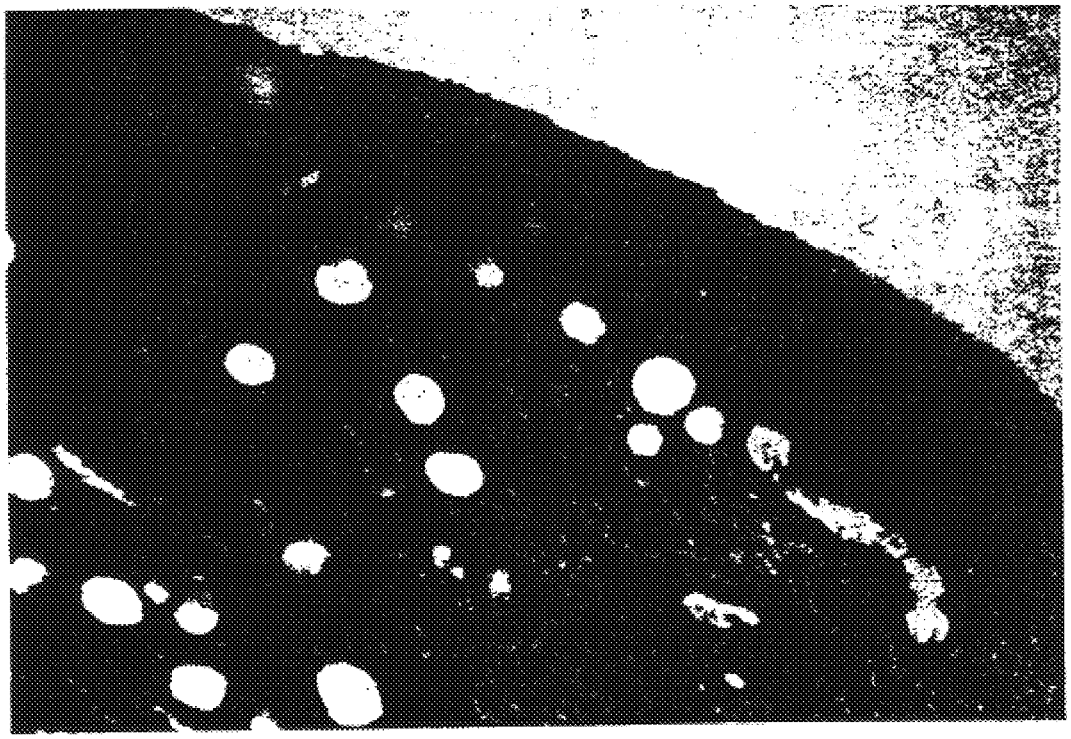
Figure 14D:
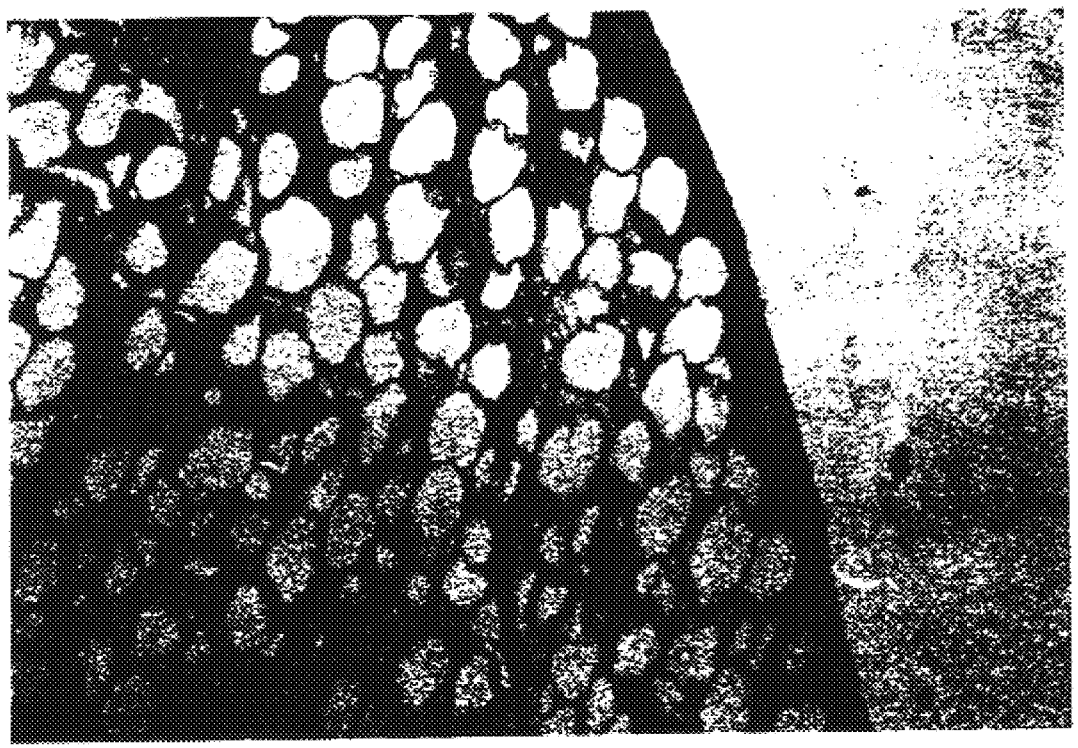

In response to 10 pg of injected hrIL-1β, control synovia became hypertrophic (FIG. 14a) and hypercellular (FIG. 14c). The increased cellularity of the synovia appeared to involve both increased numbers of synoviocytes and infiltration by leukocytes. In knees where MFG-IRAP/HIG 82 cells were present, these changes were completely suppressed and the synovia were nearly indistinguishable from control synovia (FIG. 14b, 14d).

The ex vivo transfer of the human IRAP gene to the synovial lining of rabbit knees clearly protects these joints from the pathophysiological sequelae of subsequent intra-articular challenge by hrIL-1β.

Measurements of the amounts of IL-1 present in human, recombinant synovial fluids provide values in the range of 0–500 pg/ml (Westacott, et al., 1990, Ann Rheum Dis. 49: 676–681; Malvak, et al., 1993, Arthritis Rheum 36: 781–789). Thus the amounts of IRAP expressed intra-articularly during the present, short-term experiments should be sufficient to block the biological activities of IL-1 at the concentrations present in human arthritic joints.

EXAMPLE XIII

This example shows that the level of intraarticular IRAP expressed subsequent to ex vivo transplantation of synoviocytes transduced with MFG-IRAP is sufficient to inhibit several pathophysiological changes associated with antigen-induced arthritis of the rabbit knee. Intraarticularly expressed IRAP has both a chondroprotective and anti-inflammatory effect during the acute phase of this disease. Data disclosed in Example XII support the contention that the invention as disclosed and claimed is a marked improvement for treating connective tissue disorders such as arthritis in comparison to delivery of proteins to the afflicted joint. Example XII shows that ex vivo transfer of MFG-IRAP to the rabbit knee as disclosed throughout this specification results in the intraarticular accumulation of nanogram quantities of glycosylated, biologically active IRAP. This present example shows that this same gene therapy based product inhibits joint pathologies in a rabbit model of human rheumatoid arthritis.

Young adult rabbits were subjected to a surgical, partial synovectomy of the left knee joint to provide autologous cells. These autologous cells were used to produce cultures of rabbit synovial fibroblasts (type B synoviocytes) from these biopsies as described in Example V and Example IX. Subconfluent cultures were then transduced by infection with MFG-IRAP. Expression of the transgene was confirmed by measuring the concentrations of human IRAP in the conditioned media; values typically range from 100–500 ng IRAP/$10^6$ cells/3 days. Sister cultures of synoviocytes from the same animal were infected with a BAG virus encoding the lac Z and $neo^r$ marker genes, and then selected for growth in the presence of G418 (1 mg/ml) to serve as controls. Untransduced synoviocytes were also used as additional controls.

During the period that the cells were being grown and transduced, the donor rabbits were sensitized to ovalbumin by a series of two intradermal injections of 5 mg ovalbumin emulsified in adjuvant, given two weeks apart. Two weeks after the second injection, an acute monarticular arthritis was initiated by the injection of 5 mg ovalbumin dissolved in 1 ml saline into the right knee joints. By this time the left, donor knees had regenerated their synovia, and were each injected with 1 ml saline as controls.

One day after the onset of arthritis, $10^7$ autologous cells, transduced with either the IRAP gene, or lac Z and neo genes, were injected into each arthritic knee, and each untreated, non-arthritic knee. In other control experiments, knees were injected with untransduced, autologous cells. Groups of rabbits were killed 3 and 7 days later, corresponding to the middle and end of the acute phase of this arthropathy. Knees were lavaged with 1 ml of saline, prior to the removal of synovial tissue and articular cartilage for analysis.

Intraarticular expression of the MFG-IRAP transgene was evaluated by ELISA measurements of human IRAP in the lavage fluids. IRAP concentrations in the control, non-arthritic knees is shown in FIG. 15. IRAP concentrations in the arthritic knees were always several-fold higher than in normal knees at both time points (FIG. 15). In both non-arthritic and arthritic knees transduced with MFG-IRAP, there was a slight decrease in IRAP expression with time. No human IRAP could be detected in sera obtained from normal or arthritic rabbits.

During the course of these experiments, the intraarticular concentration of rabbit IL-1 in arthritic knees was in the range of 100–200 pg/knee (FIG. 16). No IL-1α could be detected by RIA of the lavage fluids. Thus the concentration of IRAP within these knees exceeded the concentration of IL-1 by factors of approximately 10–50. Concentrations of IL-1 were lower in Day 7 arthritic knees receiving the IRAP gene (FIG. 16), suggesting that IRAP had inhibited an autocrine amplification loop.

Two major pathologies predominate in the rheumatoid joint: loss of articular cartilage and inflammation. The former occurs through a combination of reduced synthesis and enhanced degradation of the cartilaginous matrix. Whereas inflammation is manifest as a synovitis accompanied by influx of leukocytes into the joint space.

The onset of antigen-induced arthritis in this Example was accompanied by cartilage destruction, as reflected in the increased glycosaminoglycan (GAG) content of the lavage fluids (FIG. 17a), and reduced synthesis of cartilage proteoglycans, as reflected by lower uptake of $^{35}SO_4^{2-}$ (FIG. 17b). Knees expressing the MFG-IRAP transgene, but not control knees, were substantially protected from these changes. GAG release (FIG. 17a) was inhibited 55% on Day 4 and 32% on Day 7. Suppression of GAG synthesis (FIG. 17b) was inhibited by 68% on Day 4 and 100% on Day 7. The MFG-IRAP transgene also strongly reduced the influx of leukocytes into the joint space (FIG. 18), an effect that was stronger at Day 4 (65% inhibition) than at Day 7 (38% inhibition); indeed, the difference at Day 7 failed to reach statistical significance.

The MFG-IRAP construct is utilized to exemplify the presently claimed invention. In addition to this construct, the ex vivo based teachings of this specification have been utilized to transfer to synovial cells and express in vivo DNA sequences encoding human IL-1α, human TNF-α soluble receptor Types I and II, vIL-10, growth hormone, IL-6, and Lac Z and $neo^r$.

EXAMPLE XIV

The methods disclosed throughout this specification were utilized to express MFG-human IL-1 soluble receptor type I and type II constructs (with $neo^r$) within in vitro cultured synoviocytes. These transfected synoviocytes produce 1–2 ng/$10^6$ cells of IL-1 soluble receptor types I and II, following neo-selection. The additional methods disclosed throughout this specification may be utilized to procure in vivo expression data regarding these MFG-human IL-1 soluble receptor type I and type II constructs.

EXAMPLE XV

Rabbits were injected intraarticularly in one knee joint with a specific viral or non-viral vector disclosed in Table 2. Untreated knees were injected with a control, usually with the identical viral or non-viral vector with a different passenger gene. At intervals from 2 days to 2 weeks following intraarticular injection, rabbits were sacrificed and the knee joints harvested and stained with X-Gal to assay for LacZ expression. The results are depicted in Table 2. The recombinant adenovirus vector comprising a CMV-LacZ fusion and the recombinant HSV vector comprising a CMV-LacZ fusion generated the highest expression level subsequent to intraarticular injection. The recombinant retroviral vector, MFG-LacZ, was not expressed in vivo, lending credence to the concept that retroviral vectors require actively dividing cells during the infection process and the concomitant low mitotic activity of synoviocytes in the joint lining.

However, an intra-articular injection of MFG-IRAP to synovial cells of an inflamed joint space supported retroviral transduction. Injection of MFG-IRAP into an inflamed rabbit knee lead to the intraarticular accumulation of about 0.5 ng/knee at 7 days post injection. The untreated knee did not express human IRAP. The example shows a MoMLV based retrovirus can be used for in vivo gene delivery to inflamed joints.

TABLE 2

| VECTOR | PROMOTER | In Vitro LAC Z cells (%) | In Vivo LEVEL | In Vivo DURATION (Days) |
|---|---|---|---|---|
| Retrovirus (MFG) | LTR | 20–30 | 0 | 0 |
| HSV | CMV | 1 (toxic) | +++ | 5–7 |
| Adenovirus | CMV | 100 | +++ | 14 |
| Liposome (DC-chol) | CMV | 20–30 | + | 1–2 |
| None (naked DNA) | CMV | 0 | ± | 1–2 |

Level of in vivo expression was evaluated subjectively on a scale of 0–+++, based upon the degree of staining with X-Gal.
LTR = viral long terminal repeat
CMV = cytomegalovirus

EXAMPLE XVI

In the following example, a high titer retroviral vector carrying the gene for human IRAP was introduced by intraarticular injection to rabbit knees.

MFG vectors containing the DNA sequence for IRAP were prepared as described in EXAMPLE III. Human Kidney 293T cells ($1.5 \times 10^6$) were plated on 10 cm plates and transfected the following day with 20 μg pMFG-IRAP, 15 μg pMDg/p and 5 μg pCMV-VSV-G, plasmid expressing retroviral helper functions, by calcium phosphate DNA precipitation. Conditioned medium was harvested at 48 hr and 72 hr after transfection, cleared of debris by low sped centrifugation, and filtered through 0.45 μg filters. The supernatant was concentrated by ultracentrifugation. The control viral vector coded with LacZ gene was from the stable virus producing cell lines, 293GPG LacZ. Control knees received MFG LacZ in a concentration of $5 \times 10^8$/ml.

To determine the pMFG-LacZ viral titers, NIH 3T3 cells were placed at $2.5 \times 10^5$ per 6 cm plates 16 h before infection and incubated 24 h with the viral supernatants and concentrated viruses containing 8 μg/ml polybrene. Viral titers were determined as the average number of cells with blue nuclei, multiplied by a factor to account for plate size and dilution of viral stock. For pMFG-IRAP virus, the quantity of IRAP was measured by ELISA.

A rabbit was injected with HIG-IL-1 cells in both rear knees two days before the viral injection. 36 μl of IRAP expressing MFG vector was injected into the left knee and 300 μl of $1 \times 10^8$ cfu/ml pMFG-LacZ virus was injected into the right knee. Lavages were done at Day 0, Day 2 and Day 7 and the fluid used for an IRAP assay, WBC infiltration and pathological dissection. Results are shown in FIG. 19. IRAP expression in knees injected with MFG-IRAP increased over the seven days. IRAP expression in control knees was zero for all days tested.

EXAMPLE XVII

Adenoviral vectors were used to deliver genes encoding a soluble IL-1 receptor (sIL-1R) type I IgG fusion protein and/or a soluble TNF-α receptor (sTNF-αR) type I IgG fusion directly to the knees of rabbits with antigen-induced arthritis.

Adenoviral constructs were prepared by growing adenoviral vectors in 293 cells. To show expression of the soluble proteins in synovial cells, HIG-82 cells were grown to confluence in 10 cm dishes in Ham's F12 media supplemented with 10% FCS and 1% penicillin/streptomycin. The cells were washed, and $7 \times 10^7$ pfu of adenovirus suspended in 0.5 ml of saline was added. After incubation at 37° C. for 1 hr, the medium was replaced. After twenty-four hours the medium was replaced with Neuman & Tytell serumless media; forty-eight hours later the culture supernatant was removed and stored at −20° C.

Tissue culture supernatants were separated and resolved by SDS-PAGE. Proteins were then transferred to nitrocellulose at 100 V for 1 hr at 4° C. in 50 mM tris-HCl pH 8.3, 200 mM glycine, 1% SDS and 20% methanol. Membranes were blocked with 5% non-fat dried milk in 1×PBST (140 mM NaCl, 2 mM KCl, 10 mM $Na_2HPO_4$, 2 mM $KH_2PO_4$, pH 7.2 and 0.025% Tween®20) for 1 hr at room temperature. Peroxidase labeled goat anti-mouse IgG whole molecule (Sigma) diluted 1:20,000 in 5% milk/1×PBST was used to probe the membranes for 1 hr at room temperature. After extensive washing with 1×PBST, proteins of interest were detected by enhanced chemiluminescence and exposure to film.

Rabbits were sensitized to ovalbumin by a series of two intradermal injections of 5 mg ovalbumin emulsified in the first injection in Freund's complete adjuvant and Freund's incomplete adjuvant in the second. Two weeks following the second injections an acute articular arthritis was initiated in both hind knees of rabbits by the intraarticular injection of 5 mg ovalbumin dissolved in 1 ml saline. Twenty-four hours after induction of antigen- induced arthritis (a.i.a), $7 \times 10^7$ pfu of adenovirus encoding either the soluble TNFα and/or IL-1 receptors or lacZ was suspended in 0.2 ml of saline and injected into the joint space of the knee through the patellar tendon.

To lavage rabbit knee joints, 1 ml of GBSS plus 10 mM EDTA was injected into the joint space through the patellar tendon. After manipulation of the joint, the needle was reinserted and the fluid aspirated. Leukocytes in recovered lavage fluids were counted using a hemocytometer. Human TNFα receptor type I concentrations in conditioned media, lavage fluids and blood sera were measured as directed using ELISA kits from R & D Systems.

To measure proteoglycan synthesis rates, articular cartilage was first shaved from the femoral condyles and weighed. Approximately 30 mg of cartilage was then incubated in 500 μl of Neuman Tytell serumless medium with 40 uCi of $^{35}SO_4^{-2}$ for 24 hrs at 37° C. Afterward, the media were recovered and stored at −20° C. Proteoglycans were extracted from the cartilage shavings by incubation for 24 hrs in 0.5 ml of 0.5 M NaOH at 4° C. with gentle shaking. Following chromatographic separation of unincorporated $^{35}SO_4^{-2}$ using PD-10 columns (Pharmacia), radiolabeled GAGs released into the culture media or recovered by alkaline extraction were quantitated using scintillation counting.

To quantitate glycosaminoglycans (GAGs) released into the joint space as a result of cartilage proteoglycan degradation, recovered lavage fluids were first centrifuged at 12,000 g for 10 min to remove debris, and the supernatants recovered. Aliquots of 100 ul were treated with papain. Papain suspension (type III, 20 μl, 19 units.mg protein:Sigma) was added to 1 ml of buffer containing 10 mM sodium EDTA and 0.4 M sodium acetate, pH 5.2. The papain solution (100 μl) was added to lavage fluid (100 μl) and incubated overnight at 60° C. Papain was inactivated by the addition of iodoacetic acid to a final concentration of 4 mm. The samples were then centrifuged at 12,000 g for 10 min. Afterward, 2 units of hyaluronate lyase was added and the samples incubated at 37° C. overnight. Determination of sulfated GAG levels was performed in a colometric dye-binding assay using 1,9 dimethylene blue as previously described. See, for example, Farndale et al., *Biochim. Biophys. Acta.* 883: 173–177 (1986).

For histological analyses, tissues harvested from dissected knees were first fixed in 10% formalin for 24 hrs. Tissues containing bone and cartilage were subsequently decalcified by incubation in EDTA. The fixed tissues were imbedded in paraffin, sectioned at 5 um and stained with hematoxylin and eosin.

To determine luciferase content in rabbit tissues, following sacrifice tissues were dissected, immediately placed on dry ice, and later stored at −80° C. At the time of assay, tissues were thawed on ice, and approximately 0.65 g of each was finely chopped using a scalpel. The minced tissue was mixed with 2 mls 0.25 Tris-HCl, pH 7.5, and the mixture homogenized by hand with a tightly fitting dounce homogenizer. The homogenate was then collected, put through 3 freeze thaw cycles and centrifuged 15 min at low speed in a table-top clinical centrifuge. The supernatant was collected and luciferase activity in 100 ul was measured in a luminometer as directed using a luciferase assay system from Promega. To measure luciferase activity in leukocytes, cells recovered from lavage fluid or blood were counted using a hemocytometer. About $5 \times 10^6$ cells were then pelleted by centrifugation at 10,000×g for 2 min. Leukocytes were resuspended in 200 $\mu$l of 0.25 M Tris-HCl, pH 7.5 and put through 3 freeze-thaw cycles. Debris from the cell lysate was pelleted by centrifugation at 10,000×g for 2 min. Luciferase activity in 100 $\mu$l was then quantitated as above.

To determine levels of expression of the soluble TNFα and IL-1 receptor-IgG fusion constructs following adenoviral delivery to synoviocytes, approximately $3 \times 10^6$ cells of a lapine synovial fibroblast line, HIG-82, were first infected in vitro with $7 \times 10^7$ pfu of either the sTNF-αR or sIL-1R adenoviral construct (Ad.sTNF-RI-Ig and Ad.sIL-1RI-Ig, respectively). After 48 hrs culture in serumless media, culture supernatants were collected and analyzed. As shown in FIG. 20, ELISA measurements of the sTNF-αR detected greater than 300 ng per ml of medium per $10^6$ cells. Western-blot analyses using antibody specific for the murine IgG1 portion of the receptor fusion molecule demonstrated that protein of the approximate predicted size of the IL-1 receptor-Ig fusion protein (IL-1 inhibitor) was produced by the infected synovial cells and secreted at a level about 50% of that of the TNFα receptor-Ig fusion (TNFα inhibitor). Furthermore, the biological activity of the soluble IL-1 and TNFα receptors was demonstrated by their ability to partially block the effects of constitutively expressed human IL-1β in the rabbit knee and TNFα induction of NF-kB.

To test the ability of the respective receptors to inhibit the acute inflammatory effects of a.i.a. in the rabbit knee joint, a.i.a. was induced in both knees of 32 rabbits. Twenty-four hours post induction, approximately $7 \times 10^7$ pfu of either Ad.sIL-1RI-Ig, Ad.sTNF-RI-Ig, or both adenoviral vectors were injected intraarticularly into the left knee of three sets of eight rabbits. $7 \times 10^7$ pfu of adenovirus encoding lacZ was injected into the right knee of all 32 rabbits. A control group of 8 rabbits received an equal volume injection of saline in the left knee. Three days after injection of the adenovirus, both knees of each rabbit were lavaged with 1 ml of saline solution. At seven days post infection, the rabbits were sacrificed, the knees lavaged, dissected and analyzed for effects of transgene expression. It should be noted that injections of adenovirus exceeding $1 \times 10^9$ pfu proved inflammatory in naive rabbit joints, and exacerbated the pathology in knees with a.i.a., greatly increasing leukocytic infiltration into the synovial fluid and overt pathology of the joint. This was also accompanied by a loss of transgene expression in 3 to 7 days. Adenoviral doses of $7 \times 10^7$ pfu or less, however, produced no detectable leukocytic infiltrate into synovial fluid for up to 14 days post injection and maintained high levels of gene expression (data not shown).

ELISA measurements of TNFα receptor levels in recovered lavage fluids detected approximately 20 ng/ml at days 3 and 7 in knees receiving Ad.sTNF-RI-Ig alone. Significant levels of the receptor were not detected in untreated joints receiving Ad.LacZ (FIG. 21). Similarly, in knees receiving a mixture of adenovirus encoding the TNFα and IL-1 receptors together TNFα receptor expression of greater than 15 ng/ml was observed at both Day 3 and 7. Again, the TNF receptor was not detected in knees not receiving the Ad.sTNF-R virus or in blood sera.

As a quantitative index of inflammation in the rabbit knees, leukocytes in recovered lavage fluids from each group of rabbits were counted and compared. As shown in FIG. 22a, in the control group of rabbits which were injected with Ad.LacZ in the right knee and saline in the left knee, both knees were similarly inflamed with mean levels of infiltrating leukocytes exceeding $2 \times 10^7$ per ml of recovered fluid at both Day 3 and 7 post-adenoviral infection. In the group of rabbits injected with Ad.sTNF-RI-Ig in the left knee and Ad.LacZ in the right, equally high numbers of infiltrating leukocytes were seen in both knees at Day 3. By Day 7, a modest decline in the mean leukocytic infiltration was observed in knees receiving the Ad.sTNF-RI-Ig receptor. Rabbit knees injected with Ad.sIL-IRI-Ig showed a mean 65% reduction in infiltration over the control group of rabbits at Day 3 which increased to about 80% by Day 7. Interestingly, in this group of rabbits, the untreated knees which were injected with Ad.LacZ also showed a reduction in infiltration at both Day 3 and 7 relative to the control group of rabbits. Rabbits injected in the left knee with both Ad.sIL-IRI-Ig and Ad.sTNF-RI-Ig viruses showed a nearly 85–90% reduction in mean leukocytic infiltration at both Day 3 and 7 over the control group of rabbits, which was accompanied by an 80% reduction in the untreated Ad.LacZ+ knee.

To determine relative cartilage matrix degradation in the rabbit knees, glycosaminoglycans (GAG) released into synovial fluid as a result of proteoglycan breakdown were measured in recovered lavage fluids. The results of these assays, shown in FIG. 22b, correspond closely with the relative levels of leukocytic infiltration from FIG. 22a. The control group rabbits receiving injections of Ad.LacZ and saline in opposing knee joints, had similarly high levels of GAGs in the lavage fluids of both knees at both Day 3 and 7. Rabbits injected with Ad.sTNF-RI-Ig and Ad.LacZ in opposite knees likewise had elevated GAGs in both knees at both time points. However, rabbits injected in one knee with Ad.IL-1 receptor showed a greater than 50% reduction in mean GAG levels at both Day 3 and 7 over the control group rabbits. By Day 7, the untreated knees, which had been injected with Ad.lacZ also showed nearly a 40% reduction in GAG release. Rabbit knees which were injected with virus encoding both viruses had a 65% reduction in mean GAG level, while GAGs in opposing Ad.LacZ+ knees were reduced over 50%.

To test the possibility that the observed contralateral joint effect is that adenoviral particles or virally transduced cells were migrating from the joint of injection to the opposite knee or other organs thereby causing a systemic anti-inflammatory effect, an adenoviral vector encoding the firefly luciferase reporter gene (Ad.luciferase) was utilized. This reporter gene is described by deWet, et al., *Mol. Cell. Biol.* 7:725:737 (1987) and Ow, et al., *Science,* 234:856–859 (1986). Similar to experiments described above, a.i.a. was induced in both knees of two rabbits. Twenty-four hours post induction, $1.5 \times 10^9$ pfu of the Ad.luciferase virus was injected into one knee of each rabbit, while the untreated knee received $7 \times 10^7$ pfu of Ad.lacZ. At 7 days post injection, the rabbits were bled and sacrificed, the joints lavaged, and the joint capsules of both knees harvested along with regional lymphoid tissue, heart, liver, lung, spleen and kidney. Recovered tissues and leukocytes were then analyzed for the presence of intracellular luciferase activity. As shown in FIG. 24, a low level of luciferase activity was observable in lymphoid tissued obtained near the site of injection and in synovial tissue of the untreated knee joint relative to knees receiving the Ad.luciferase vector. Analysis of similar numbers of leukocytes obtained from both knee joints and peripheral blood showed luciferase activity in leukocytes obtained from the injected knee and a lower level in the untreated knee. No appreciable activity was detected in circulating leukocytes. These results demonstrate that a population of transduced leukocytes can migrate to the opposing inflamed knee joint suggesting a possible mechanism for the observed contralateral effect.

The results of this example show that direct intraarticular delivery of adenoviral vectors encoding IL-1 and TNF inhibitors has an anti-inflammatory effect that is not limited to the injected joint.

The results of this example further demonstrate that intraarticular adenoviral gene delivery of soluble receptor molecules for IL-1 and TNFα can partially block an acute inflammatory response in a.i.a. in the rabbit knee. Delivery of the IL-1 soluble receptor gene alone was found to be considerably more effective at inhibiting synovial fluid leukocytosis and cartilage matrix degradation than the TNFα inhibitor. However, simultaneous gene delivery of both inhibitors was the most effective, resulting in a net reduction in leukocytosis, cartilage matrix degradation and synovitis. The enhanced therapeutic effects observed following injection of both Ad.sIL-1RI-Ig and Ad.sTNF-RI-Ig demonstrates that the strategies of the present invention directed at blocking the activity of both TNFα and IL-1 are considerably more effective in the treatment of RA than targeting either cytokine individually. The coinjection of both cytokines into the joints of rabbits was found to stimulate significantly greater leukocytic infiltration into the synovial fluid than when either was administered alone. This observation is consistent with RA being a disorder driven by the imbalance of a cytokine network and that therapies which target the activities of multiple inflammatory effectors would be the most beneficial.

Surprisingly, these anti-inflammatory responses were also apparent in untreated knees which received adenovirus encoding the lacZ gene, suggesting that local intraarticular gene therapy may have distal or systemic anti-inflammatory effects. This example, therefore, further demonstrates that intraarticular gene delivery of the IL-1 and TNFα inhibitors has systemic anti-inflammatory effects, or at least therapeutic effects which extend to the untreated knee joint. If this observed untreated joint effect was due to therapeutic levels of inhibitor molecules leaking from the joint space to the circulation, it would seem that they should be detectable in the serum or in lavage fluids recovered from the untreated joint. However, sTNFα receptor was not detected outside the injected joint. In contrast, cell trafficking studies conducted using the Ad.luciferase vector indicate that a percentage of leukocytes transduced by adenovirus in one joint migrate to the opposing inflamed joint. This indicates that even though significant levels soluble TNFα receptor were not detected in animal fluids by ELISA, a population of leukocytes capable of expressing the inhibitor genes does not indeed migrate from the site of transduction, and travel either via the circulatory or lymphatic system.

Histological analyses of tissue recovered from the knees of each group of rabbits is shown in FIG. 23. When compared to tissue recovered from normal, naive rabbits (FIG. 23*a*), sections from the Ad.lacZ/saline group showed a severe synovitis typical of that seen with a.i.a. (FIG. 23*b*), as reported, for example, by Edwards, et al., *Br. J. Exp. Path.* 69:739–748 (1988). The synovium was dramatically thickened, highly fibrous, and hypercellular with increased numbers of synovial cells and infiltrating mononuclear leukocytes. A small population of polymorphonuclear leukocytes was also present. Treatment of joints with Ad.sTNF-RI-Ig alone had little observable effect on the severity of synovitis in either the treated (FIG. 23*c*) or untreated joint (FIG. 23*d*). Synovial sections from this group of rabbits were largely indistinguishable from that of the a.i.a. knees from the Ad.lacZ/saline group. Although somewhat variable among the rabbits within the group, knees receiving intraarticular injection of Ad.sIL-1RI-Ig (FIG. 23*e*) showed a limited but distinct reduction in synovitis. The general pathology was the same as the Ad.lacZ/saline group, but the severity was observably reduced. Opposing contralateral joints also had a detectable reduction in synovitis (FIG. 23*f*). Knees of rabbits receiving both the Ad.sIL-1RI-Ig and Ad.sTNF-RI-Ig vectors together showed a marked reduction in synovial pathology (FIG. 23*g*). As with the IL-1 inhibitor, the extent of the response varied somewhat between rabbits within the group. In general, the synovium was considerably less hypertrophied, and fibrous; infiltrating mononuclear leukocytes were clearly apparent, but in much lower numbers than the Ad.lacZ/saline a.i.a. knees. Contralateral knees within this group also showed a significant reduction in synovitis (FIG. 23*h*).

The results of these experiments clearly demonstrate that adenoviral vectors can be used to efficiently deliver potentially therapeutic genes directly to intraarticular tissues and that subsequent expression of these genes can occur at levels sufficient to observe beneficial effects, both in the treated joint and distal joints, in an animal model of arthritis.

EXAMPLE XVIII

Female DBA/1 lacJ mice were obtained from Jackson Laboratories, Bar Harbor, Me. An adenovirus vector was prepared according to the methods of Example XVII, only using a DNA sequence encoding for vIL-10, vIL-10 is a variation of interleukin-10 produced by the Epstein Barr Virus. Mice were injected with Bovine type II Collagen (CII) on Day 0 to product a collagen induced arthritis p Type II collagen-induced arthritis (CIA) in mice is an experimental model of arthritis with a number of pathological, immunological and genetic features in common with rheumatoid arthritis. This disease is induced by immunization of susceptible strains of mice with type II collagen, the major component of joint cartilage and leads to progressive, inflammatory arthritis in the majority of immunized animals. Collagen-induced arthritis is characterized clinically by erythema and edema, with affected paw width increases of typically 100%. Histopathology of effected joints reveals synovitis, pannus formation, and cartilage and bone erosion. Clinically, paw swelling is followed by distortion and eventually ankylosis as seen in human RA. This model is now well established for testing of immunotherapeutic approaches to treating joint diseases, and has been successfully employed for the study of both biological and pharmacological agents for treatment of rheumatoid arthritis.

The arthritis develops gradually, and vectors were administered on Day 24 before swelling begins. The Ad.vIL-10 vectors were injected into left front and left rear mouse paws at concentrations of $10^7$, $10^6$ or $10^5$ pfu, as indicated in FIG. 30 at Day 24 after collagen injection. Right front and rear paws were uninjected. Results shown in FIG. 25 illustrate that on Day 29 following onset of arthritis paws injected with Ad.vIL-10 had no incidence of arthritis, while over 60% of control paws had arthritis. On days 33 and 42, the number of Ad.vIL-10 paws that had arthritis was about half the number of control paws that had arthritis. Similar results were obtained when Ad.vIL-10 was injected into rear paws, while front paws were uninjected. These results are shown in FIG. 26. Similar results were also seen with diagonal injection of Ad.vIL-10 into the front right and left rear paws while the opposite paws were uninjected. As shown in FIG. 27, over 50% of control paws had arthritis after Day 29; after days 33 and 42, about three times as many control paws had arthritis than paws injected with Ad.vIL-10. The amount of vIL-10 expressed by a paw injected with Ad.vIL-10 and protected from arthritis and a control paw was determined by ex vivo production following euthanasia and removal of the paw. Paws were incubated in a culture media; the level of vIL-10 in the culture media was determined by ELISA. Results are shown in FIG. 28; Ad.vIL-10 injected paws had almost five times the expression of vIL-10 when compared to control paws. A similar determination was made comparing an injected paw not protected from arthritis and a control paw. As shown in FIG. 29, the level of expression of vIL-10 in both paws was about the same.

In a further investigation, footpads of mice were injected in vivo with Ad.vIL-10, prepared as described above. Forty-eight hours after injection, the mice were sacrificed and draining lymph nodes were surgically removed. Lymph node cells were cultured for 48 hours in vitro. More specifically, the lymph nodes cut out of the mice were put in 24 well plate with culture medium and allowed to sit. The supernatant was tested for the presence of vIL-10 by ELISA. As shown in FIG. 30, the higher the concentration of Ad.vIL-10 injected, the greater the amount of vIL-10 was expressed.

This example demonstrates that in vivo injection of adenovirus carrying the DNA sequence for vIL-10 results in expression of vIL-10 in mouse paws. This expression provides a protective effect against an arthritis challenge. Mouse paws which withstood the arthritis challenge were shown to have vIL-10 expression almost five times as high as that in control paws, thereby linking the vIL-10 expression to the protective effect.

EXAMPLE XIX

An adenovirus vector was prepared according to the methods of Example XVII, only using a DNA sequence encoding for iNOS instead of sTNF-αR or sIL-1R. Either $10^7$, $10^6$ or $10^5$ pfu of Ad.iNOS vector, as indicated in FIG. 31, were injected by intraarticular injection to the left knees of rabbits. Right knees, which served as the control, received an injection of the Ad.LacZ vector. FIG. 31a shows WBC count in left and right knees for Days 2 through 7. FIG. 31b shows the GAG release for both the Ad.iNOS and control knees. FIG. 32 shows a measure of NOS activity expressed as CMP/mg protein for days 2 through 7. These results suggest that in knees expressing iNOS, elevated NO, elevated inflammation and elevated GAG release were observed. Thus, the iNOS caused joint inflammation and cartilage matrix breakdown. The example also shows in vivo expression of a gene.

EXAMPLE XX

Figure 37A:
Figure 37B:
Figure 37C:
Figure 37D:

Ad.vIL-10 vectors were prepared as described in Example XVIII. An antigen induced arthritis was induced in the knees. Following the initiation, half of the rabbit knees were injected with Ad.vIL-10 in concentration of $5 \times 10^7$ pfu by a single injection into the joint. Control knees received Ad.LacZ. As shown in FIG. 33, leukocyte infiltration was measured 3 and 7 days after injection. Knees receiving the vIL-10 injection had a marked decrease in leukocyte infiltration when compared to control knees. Untreated knees, which did not receive an injection of either Ad.vIL-10 or Ad.LacZ, also showed a marked reduction in leukocyte infiltration. Levels of GAG released was also markedly lower in vIL-10 and untreated knees as compared with control knees. (FIG. 34). GAG synthesis rate in vIL-10 knees and untreated knees was higher than that of control knees (FIG. 35). As shown in FIG. 36, vIL-10 expression increased from Day 3 to day 7, demonstrating that the methods of the present invention were effective in introducing a vector containing a gene into a host joint. FIG. 37 provides pictures of the histological analysis of both the Ad.vIL-10 injected knee (FIG. 37c) and the untreated knee (FIG. 37d), which shows a significant reduction in synovitis compared to the Ad.LaZ control knees (FIG. 37b). The synovium in the Ad.vIL-10 treated joint resembles that of the normal, untreated joint (FIG. 37a). This example further illustrates that the methods of this invention can be used to introduce a therapeutic gene to a host, and subsequent expression of the gene will yield a therapeutic benefit in the host. vIL-10 is shown to block inflammatory cell infiltration into the joint of a.i.a. induced rabbits, and may also be chondroprotective and able to block synovial cell hyperplasia. This therapeutic benefit is seen both in the joint injected with the vector containing the gene and the untreated joint.

EXAMPLE XXI

C.I.A. was induced in mice as described in Example XVIII. About 24 days after collagen injection, rear paws were injected with either Ad.vIL-10 or Ad.luciferase. Injections were done either intraperitoneally (IP) or intravenously (IV). At 4–5 week post treatment, the treated animals develop swollen paws which upon histological analysis resemble human disease. Moreover, the animals have elevated levels of antibodies to type II collagen. The mice were then scored for the percentage of swollen paws. As shown in FIG. 38, delivery of Ad.vIL-10 to the rear paws of the arthritic mice completely blocks paw swelling. In contrast, injection of Ad.luciferase had no appreciable effect on the percent of paws which became swollen. While there was an effect of injection of vIL-10 in the rear paws on swelling in the front untreated paw, there was no therapeutic effect of Ad.vIL-10 when delivered systemically by IV or IP injection (FIG. 39). This result suggests that local delivery and expression of vIL-10 has a stronger therapeutic effect than general systemic administration.

It will be appreciated by those skilled in the art that this invention provides a method for introducing into a target cell of a mammalian host in vitro, or in the alternative in vivo, at least one gene that encodes for at least one protein or peptide with therapeutic properties. This method includes employing genes having DNA that is capable of maintenance and expression.

It will be appreciated by those skilled in the art that this invention provides a method for introducing at least one gene encoding a product into at least one target cell of a mammalian host for treating an arthritic condition of the mammalian host.

It will be understood by those skilled in the art that this invention provides a method to repair and regenerate the connective tissue of a mammalian host.

It will be further understood that this invention provides a method to produce an animal model for the study of connective tissue pathology.

It will be appreciated by those persons skilled in the art that this invention provides a method of using and a method of preparing numerous genes including a gene encoding a soluble interleukin-1 receptor that is capable of binding to and neutralizing substantially all isoforms of interleukin-1, and thus substantially protect cartilage of a mammalian host from pathological degradation. In addition, it will be understood by those persons skilled in the art that the method of using the gene of this invention will reduce inflammation, protect soft tissues of the joint and suppress the loss of bone that occurs in patients suffering with joint pathologies.

It will be appreciated by those persons skilled in the art that the viral vectors employed in this invention may be employed to transfect target cells in vivo, or in culture, such as by direct intraarticular injection or transplantation of autologous target cells from the patient transduced with the retroviral vector carrying a gene or genes of interest.

The present invention provides a method for preparing various vectors, both viral and non-viral, that contain DNA sequences encoding for numerous genes of interest. These genes are known by those skilled in the art to be useful in the therapeutic treatment of various cartilage defects and connective tissue disorders. The present invention demonstrates that in vivo infection of target cells in the joint of a host results in in vivo expression of the protein encoded by the DNA sequence. Such expression then leads to the prevention and/or alleviation of symptoms common to numerous connective tissue disorders. Thus, the methods of the present invention provide a means for treating a patient by in vivo infection of the joints of the patient with a vector containing a DNA sequence encoding a therapeutic product.

The present invention also provides a method for treating a patient for a cartilage defect or connective tissue disorder by introducing two or more DNA sequences encoding two different products of interest. Introduction can be simultaneous or in succession. Multiple genes can all be placed on one vector or on separate vectors. Expression of two or more different genes has an enhanced therapeutic benefit.

The present invention also provides a method for treating a host in which one joint is treated and a therapeutic benefit is realized both in the treated joint and in other joints of the host as well.

Whereas particular embodiments of this invention have been described above for purposes of illustration, it will be evident to those persons skilled in the art that numerous variations of the details of the present invention may be made without departing from the invention as defined in the appended claims.

What is claimed is:

1. A method for inhibiting leukocyte infiltration or cartilage degradation in a joint of a mammal, the method comprising directly administering to said joint a viral vector comprising a nucleic acid sequence, operably linked to a promoter, encoding a protein of interest, wherein said protein is selected from the group consisting of IRAP, soluble IL-1 receptor, soluble TNF-α receptor, IL-10, and biologically active fragments and biologically active derivatives of these proteins, and wherein expression of said protein within said joint results in an inhibition of leukocyte infiltration or cartilage degradation in said joint.

2. The method of claim 1, wherein said IL-10 is vIL-10.

3. The method of claim 1, wherein said soluble IL-1 receptor is selected from the group consisting of soluble IL-1 receptor type I, soluble IL-1 receptor type II, and soluble IL-1 receptor-Ig fusion protein.

4. The method of claim 1, wherein said soluble TNF-α receptor is a TNF-α receptor type I, soluble TNF-α receptor type II, or a TNF-α receptor-Ig fusion protein.

5. The method of claim 1, wherein said method comprises directly administering to said joint one or more viral vectors comprising a nucleotide sequence encoding a soluble IL-1 receptor and a nucleotide sequence encoding a soluble TNF-α receptor.

6. The method of claim 1, wherein said viral vector is an adenoviral vector, a herpes simplex viral vector, or a retroviral vector.

7. The method of claim 1, wherein said viral vector is directly administered to said joint by intra-articular injection.

* * * * *